US010639349B2

(12) United States Patent
Chen et al.

(10) Patent No.: US 10,639,349 B2
(45) Date of Patent: May 5, 2020

(54) H3T3A MUTANT PROTEIN EFFICIENTLY REDUCES H3T3P AND CAUSES INCREASED CELL DEATH OF RAPIDLY DIVIDING CELLS

(71) Applicant: THE JOHNS HOPKINS UNIVERSITY, Baltimore, MD (US)

(72) Inventors: Xin Chen, Baltimore, MD (US); Jing Xie, Ellicott City, MD (US)

(73) Assignee: The Johns Hopkins University, Baltimore, MD (US)

(*) Notice: Subject to any disclaimer, the term of this patent is extended or adjusted under 35 U.S.C. 154(b) by 0 days.

(21) Appl. No.: 15/565,120

(22) PCT Filed: Apr. 6, 2016

(86) PCT No.: PCT/US2016/026114
§ 371 (c)(1),
(2) Date: Oct. 6, 2017

(87) PCT Pub. No.: WO2016/164392
PCT Pub. Date: Oct. 13, 2016

(65) Prior Publication Data
US 2018/0256680 A1    Sep. 13, 2018

Related U.S. Application Data

(60) Provisional application No. 62/143,546, filed on Apr. 6, 2015.

(51) Int. Cl.
| A61K 38/17 | (2006.01) |
| A61P 35/00 | (2006.01) |
| A61K 39/395 | (2006.01) |
| A61K 45/06 | (2006.01) |
| C07K 14/47 | (2006.01) |
| C07K 16/30 | (2006.01) |
| G01N 33/574 | (2006.01) |
| A61K 38/00 | (2006.01) |

(52) U.S. Cl.
CPC .... *A61K 38/1709* (2013.01); *A61K 39/39558* (2013.01); *A61K 45/06* (2013.01); *A61P 35/00* (2018.01); *C07K 14/47* (2013.01); *C07K 16/3053* (2013.01); *G01N 33/5743* (2013.01); *A61K 38/00* (2013.01); *C07K 2317/21* (2013.01); *C07K 2317/565* (2013.01); *C07K 2317/622* (2013.01); *C07K 2317/73* (2013.01); *G01N 2333/4722* (2013.01); *G01N 2800/50* (2013.01)

(58) Field of Classification Search
None
See application file for complete search history.

(56) References Cited

U.S. PATENT DOCUMENTS

| 7,399,787 B2 | 7/2008 | Chiao et al. |
| 2013/0267579 A1 | 10/2013 | Croce |
| 2013/0323198 A1 | 12/2013 | Friberg et al. |

FOREIGN PATENT DOCUMENTS

| WO | 2005/028620 A2 | 3/2005 |
| WO | 2010/120942 A2 | 10/2010 |
| WO | 2013/049093 A1 | 4/2013 |

OTHER PUBLICATIONS

Huertas et al. Oncogene (2012) 31, 1408-1418.*
Venken, et al., MiMIC: a highly versatile transposon insertion resource for engineering *Drosophila melanogaster* genes. Nat Methods. Sep. 2011;8(9):737-43.
De Antoni, et al., A small-molecule inhibitor of Haspin alters the kinetochore functions of Aurora B. J Cell Biol. Oct. 15, 2012;199(2):269-84.
Vagnarelli, et al., Repo-Man coordinates chromosomal reorganization with nuclear envelope reassembly during mitotic exit. Dev Cell. Aug. 16, 2011;21(2):328-42.
Xie, et al., Histone H3 Threonine Phosphorylation Regulates Asymmetric Histone Inheritance in the *Drosophila* Male Germline. Cell. Nov. 5, 2015;163(4):920-933.
Maiolica, et al., Modulation of the chromatin phosphoproteome by the Haspin protein kinase. Mol Cell Proteomics. Jul. 2014;13(7):1724-40.
Probst, et al., Epigenetic inheritance during the cell cycle. Nat Rev Mol Cell Biol. Mar. 2009;10(3):192-206.
Nguyen, et al., Phosphorylation of threonine 3 on histone H3 by haspin kinase is required for meiosis I in mouse oocytes. J Cell Sci. Dec. 1, 2014;127(Pt 23):5066-78.
Qian, et al., PP1/Repo-man dephosphorylates mitotic histone H3 at T3 and regulates chromosomal aurora B targeting. Curr Biol. May 10, 2011;21(9):766-73.
El-Osta, Review on epigenetics in cancer gene therapy: series I. Nature. 2005; 12:663-664.
Cherblanc, et al., Current limitations and future opportunities for epigenetic therapies. Future Med Chem. Mar. 2012;4(4):425-46.
Tan, et al., Pharmacologic disruption of Polycomb-repressive complex 2-mediated gene repression selectively induces apoptosis in cancer cells. Genes Dev. May 1, 2007;21(9):1050-63.

(Continued)

*Primary Examiner* — Oluwatosin A Ogunbiyi
(74) *Attorney, Agent, or Firm* — Mintz Levin Cohn Ferris Glovsky and Popeo, P.C.; Peter F. Corless

(57) ABSTRACT

The invention features compositions comprising an H3T3A mutant protein. Described herein are methods of inducing cell death in a rapidly dividing cell comprising contacting a rapidly dividing cell with an agent that reduces phosphorylation at threonine 3 of histone 3 (H3T3P), thereby inducing cell cycle arrest followed by cell death. In some cases, the rapidly dividing cell is a tumor cell, e.g., a cancer cell. The agent that reduces phosphorylation of H3T3P comprises an H3T3A mutant protein, e.g., a mutant transgenic protein. Described herein is a kit for arresting cell cycle comprising an agent that reduces phosphorylation H3T3P.

12 Claims, 42 Drawing Sheets
(15 of 42 Drawing Sheet(s) Filed in Color)
Specification includes a Sequence Listing.

(56) References Cited

OTHER PUBLICATIONS

Chen, et al., Smac mimetics as new cancer therapeutics. Anticancer Drugs. Sep. 2009;20(8):646-58.
Lee, et al., PEA-15 unphosphorylated at both serine 104 and serine 116 inhibits ovarian cancer cell tumorigenicity and progression through blocking ?-catenin. Oncogenesis. Jul. 2012; 1(7): e22.
Wahl, et al., Molecular hybridization of immobilized nucleic acids: theoretical concepts and practical considerations. Methods Enzymol. 1987;152:399-407.
Kimmel, et al., Identification and characterization of specific clones: strategy for confirming the validity of presumptive clones. Methods Enzymol. 1987;152:507-11.
Benton, et al., Screening lambdagt recombinant clones by hybridization to single plaques in situ. Science. Apr. 8, 1977;196(4286):180-2.
Grunstein, et al., Colony hybridization: a method for the isolation of cloned DNAs that contain a specific gene. Proc Natl Acad Sci U S A. Oct. 1975; 72(10): 3961-3965.
Tran, et al., Asymmetric Division of *Drosophila* Male Germline Stem Cell Shows Asymmetric Histone Distribution. Science. Nov. 2, 2012;338(6107):679-82.
Tran, et al., Asymmetric distribution of histones during *Drosophila* male germline stem cell asymmetric divisions. Chromosome Res. May 2013;21(3):255-69.
Kiger, et al., Stem cell self-renewal specified by JAK-STAT activation in response to a support cell cue. Science. Dec. 21, 2001;294(5551):2542-5.
Tulina, et al., Control of stem cell self-renewal in *Drosophila* spermatogenesis by JAK-STAT signaling. Science. Dec. 21, 2001;294(5551):2546-9.
Eliazer, et al., Loss of lysine-specific demethylase 1 nonautonomously causes stem cell tumors in the *Drosophila* ovary. Proc Natl Acad Sci U S A. Apr. 26, 2011;108(17):7064-9.
Eun, et al., A Non-Cell Autonomous Role of E(z) to Prevent Germ Cells from Turning on a Somatic Cell Marker. Science. Mar. 28, 2014; 343(6178): 1513-1516.
Tran, et al., Somatic control over the germline stem cell lineage during *Drosophila* spermatogenesis. Nature. Oct. 2000;407:754-757.
Chen, et al., The nuclear lamina regulates germline stem cell niche organization via modulation of EGFR signaling. Cell Stem Cell. Jul. 3, 2013;13(1):73-86.
Yadlapalli, et al., *Drosophila* male germline stem cells do not asymmetrically segregate chromosome strands. J Cell Sci. Mar. 15, 2011;124(Pt 6):933-9.
Yuan, et al., Regulation of cyclin A localization downstream of Par-1 function is critical for the centrosome orientation checkpoint in *Drosophila* male germline stem cells. Dev Biol. Jan. 1, 2012;361(1):57-67.
Siegel, et al., Cancer statistics, 2012. CA Cancer J Clin. Jan.-Feb. 2012;62(1):10-29.
Morrison, et al., Asymmetric and symmetric stem-cell divisions in development and cancer. Nature. Jun. 29, 2006;441(7097):1068-74.
Betschinger, et al., Dare to be different: asymmetric cell division in *Drosophila*, C. elegans and vertebrates. Curr Biol. Aug. 24, 2004;14(16):R674-85.
Clevers, Stem cells, asymmetric division and cancer. Nat Genet. Oct. 2005;37(10):1027-8.
Inaba, et al., Asymmetric stem cell division: precision for robustness. Cell Stem Cell. Oct. 5, 2012;11(4):461-9.
Terry, et al., Novel regulators revealed by profiling *Drosophila* testis stem cells within their niche. Dev Biol. Jun. 1, 2006;294(1):246-57.
Van Doren, et al., Regulation of zygotic gene expression in *Drosophila* primordial germ cells. Curr Biol. Feb. 12, 1998;8(4):243-6.
Ahmad, et al., The histone variant H3.3 marks active chromatin by replication-independent nucleosome assembly. Mol Cell. Jun. 2002;9(6):1191-200.
Ahmad, et al., Centromeres are specialized replication domains in heterochromatin. J Cell Biol. Apr. 2, 2001;153 (1)101-10.

Hime, et al., Assembly of ring canals in the male germ line from structural components of the contractile ring. J Cell Sci. Dec. 1996;109 ( Pt 12):2779-88.
Gao, et al., 3D live fluorescence imaging of cellular dynamics using Bessel beam plane illumination microscopy. Nat Protoc. May 2014;9(5):1083-101.
Chen, et al., Lattice light-sheet microscopy: Imaging molecules to embryos at high spatiotemporal resolution. Science. Oct. 24, 2014;346(6208):1257998.
Gan, et al., Dynamic regulation of alternative splicing and chromatin structure in *Drosophila* gonads revealed by RNA-seq. Cell Res. Jul. 2010;20(7):763-83.
Langmead, et al., Ultrafast and memory-efficient alignment of short DNA sequences to the human genome. Genome Biol. 2009; 10(3): R25.
Robinson, et al., edgeR: a Bioconductor package for differential expression analysis of digital gene expression data. Bioinformatics. Jan. 1, 2010;26(1)139-40.
Wang, et al., Histone H3 Thr-3 phosphorylation by Haspin positions Aurora B at centromeres in mitosis. Science. Oct. 8, 2010;330(6001):231-5.
Kelly, et al., Survivin reads phosphorylated histone H3 threonine 3 to activate the mitotic kinase Aurora B. Science. Oct. 8, 2010;330(6001):235-9.
Yamagishi, et al., Two histone marks establish the inner centromere and chromosome bi-orientation. Science. Oct. 8, 2010;330(6001):239-43.
Dai, et al., The kinase haspin is required for mitotic histone H3 Thr 3 phosphorylation and normal metaphase chromosome alignment. Genes Dev. Feb. 15, 2005;19(4):472-88.
Escriba, et al., Histone H3 phosphorylation and elimination of paternal X chromosomes at early cleavages in sciarid flies. J Cell Sci. Jul. 15, 2013;126(Pt 14):3214-22.
Lewis, et al., Inhibition of PRC2 activity by a gain-of-function H3 mutation found in pediatric glioblastoma. Science. May 17, 2013;340(6134):857-61.
Herz, et al., Histone H3 lysine-to-methionine mutants as a paradigm to study chromatin signaling. Science. Aug. 29, 2014;345(6200):1065-70.
Sheng, et al., Live imaging of the *Drosophila* spermatogonial stem cell niche reveals novel mechanisms regulating germline stem cell output. Development. Aug. 2011;138(16):3367-76.
Yadlapalli, et al., Chromosome-specific nonrandom sister chromatid segregation during stem-cell division. Nature. Jun. 13, 2013;498(7453)251-4.
Lin, et al., The *Drosophila* fusome, a germline-specific organelle, contains membrane skeletal proteins and functions in cyst formation. Development. Apr. 1994;120(4):947-56.
De Cuevas, et al., Morphogenesis of the *Drosophila* fusome and its implications for oocyte specification. Development. Aug. 1998;125(15):2781-9.
Schulz, et al., A misexpression screen reveals effects of bag-of-marbles and TGF beta class signaling on the *Drosophila* male germ-line stem cell lineage. Genetics. Jun. 2004;167(2):707-23.
Tazuke, et al., A germline-specific gap junction protein required for survival of differentiating early germ cells. Development. May 2002;129(10):2529-39.
Monk, et al., HOW is required for stem cell maintenance in the *Drosophila* testis and for the onset of transit-amplifying divisions. Cell Stem Cell. Apr. 2, 2010;6(4):348-60.
Gonczy, et al., The germ line regulates somatic cyst cell proliferation and fate during *Drosophila* spermatogenesis. Development. Aug. 1996;122(8):2437-47.
Dinardo, et al., lines and bowl affect the specification of cyst stem cells and niche cells in the *Drosophila* testis. Development. May 2011;138(9):1687-96.
Issigonis, et al., JAK-STAT signal inhibition regulates competition in the *Drosophila* testis stem cell niche. Science. Oct. 2, 2009;326(5949)153-6.
Leatherman, et al., Zfh-1 controls somatic stem cell self-renewal in the *Drosophila* testis and nonautonomously influences germline stem cell self-renewal. Cell Stem Cell. Jul. 3, 2008;3(1):44-54.

(56) References Cited

OTHER PUBLICATIONS

Cheng, et al., Centrosome misorientation reduces stem cell division during ageing. Nature. Dec. 4, 2008; 456(7222):599-604.
Ni, et al., A genome-scale shRNA resource for transgenic RNAi in *Drosophila*. Nat Methods. May 2011;8(5):405-7.
Panigada, et al., Yeast haspin kinase regulates polarity cues necessary for mitotic spindle positioning and is required to tolerate mitotic arrest. Dev Cell. Sep. 16, 2013;26(5):483-95.

* cited by examiner

FIG. 28

| | H3 | |
|---|---|---|
| Pair # | GFP: GSC/GB | mKO: GB/GSC |
| 1 | 2.70 | |
| 2 | 3.39 | |
| 3 | 2.54 | |
| 4 | 1.31 | |
| 5 | 2.45 | |
| 6 | 1.71 | |
| 7 | 1.60 | |
| 8 | 1.30 | |
| 9 | 1.40 | |
| 10 | 3.99 | |
| 11 | 1.41 | |
| 12 | 1.79 | |
| 13 | 1.18 | |
| 14 | 2.15 | |
| 15 | 9.26 | |
| 16 | 5.96 | |
| 17 | 7.79 | |
| 18 | 16.38 | |
| 19 | 3.46 | |
| 20 | 2.94 | |
| 21 | 2.02 | |
| 22 | 4.32 | |
| 23 | 1.68 | |
| 24 | 4.58 | |
| 25 | 11.89 | |
| 26 | 26.19 | |
| 27 | 15.68 | |
| 28 | 27.46 | |
| 29 | 1.00 | |
| 30 | 9.74 | |
| 31 | 5.36 | |
| 32 | 4.74 | |

| | H3T3A | |
|---|---|---|
| Pair # | GFP: GSC/GB | mKO: GB/GSC |
| 1 | 9.33 | |
| 2 | 0.83 | |
| 3 | 1.10 | |
| 4 | 0.94 | |
| 5 | 0.85 | |
| 6 | 0.99 | |
| 7 | 0.90 | |
| 8 | 0.82 | |
| 9 | 1.40 | |
| 10 | 0.76 | |
| 11 | 1.00 | |
| 12 | 1.25 | |
| 13 | 0.86 | |
| 14 | 0.88 | |
| 15 | 0.69 | |
| 16 | 0.99 | |
| 17 | 0.69 | |
| 18 | 0.88 | |
| 19 | 0.58 | |
| 20 | 0.94 | |
| 21 | 1.10 | |
| 22 | 0.92 | |
| 23 | 0.93 | |
| 24 | 1.48 | |
| 25 | 0.75 | |
| 26 | 0.91 | |
| 27 | 0.91 | |
| 28 | 0.65 | |
| 29 | 0.82 | |
| 30 | 0.74 | |
| 31 | 0.94 | |
| 32 | 0.80 | |

| | H3T3D | |
|---|---|---|
| Pair # | GFP: GSC/GB | mKO: GB/GSC |
| 1 | 1.29 | |
| 2 | 0.88 | |
| 3 | 0.88 | |
| 4 | 0.80 | |
| 5 | 1.24 | |
| 6 | 0.90 | |
| 7 | 0.75 | |
| 8 | 0.92 | |
| 9 | 0.92 | |
| 10 | 0.93 | |
| 11 | 1.10 | |
| 12 | 0.85 | |
| 13 | 0.67 | |
| 14 | 0.55 | |
| 15 | 0.08 | |
| 16 | 0.06 | |
| 17 | 1.08 | |
| 18 | 0.78 | |
| 19 | 0.91 | |
| 20 | 0.86 | |
| 21 | 0.81 | |
| 22 | 0.93 | |
| 23 | 0.96 | |
| 24 | 0.80 | |
| 25 | 0.56 | |
| 26 | 0.96 | |
| 27 | 0.94 | |
| 28 | 0.77 | |
| 29 | 0.95 | |
| 30 | 0.63 | |
| 31 | 0.89 | |

FIG. 28 (continued)

| | | | | | |
|---|---|---|---|---|---|
| 33 | 2.46 | | 33 | 0.58 | |
| 34 | 1.56 | | 34 | 1.08 | |
| 35 | 21.84 | | 35 | 0.71 | |
| 36 | 9.93 | | 36 | 1.35 | |
| 37 | 10.00 | | 37 | 0.56 | |
| 38 | 36.56 | | 38 | 0.07 | |
| 39 | 43.31 | | | | |
| 40 | 4.94 | | | | |
| 41 | 4.55 | | | | |
| 42 | 10.48 | | | | |
| 43 | 18.73 | | | | |
| 44 | 66.01 | | | | |
| 45 | 21.52 | | | | |
| 46 | 18.16 | | | | |
| 47 | 28.13 | | | | |
| 48 | 6.82 | | | | |
| 49 | 10.44 | | | | |
| 50 | 10.44 | | | | |
| 51 | 1.05 | | | | |
| 52 | 2.60 | | | | |
| 53 | 1.82 | | | | |
| 54 | 14.30 | | | | |
| 55 | 10.70 | | | | |

FIG. 29A

|   |     | Mbps | X<br>22 | Y<br>40 | II<br>44 | III<br>52 | Sum GFP | >1.5<br><0.66<br>GFP: GSC/GB |
|---|-----|------|----|----|----|-----|-----|------|
| 1 | GSC |      | 22 | 40 | 88 | 104 | 254 | NA |
|   | GB  |      | 22 | 40 | 88 | 104 | 0   |    |
| 2 | GSC |      | 22 | 40 | 88 | 104 | 214 | 5.35 |
|   | GB  |      | 22 | 40 | 88 | 104 | 40  |    |
| 3 | GSC |      | 22 | 40 | 88 | 104 | 232 | 10.55 |
|   | GB  |      | 22 | 40 | 88 | 104 | 22  |    |
| 4 | GSC |      | 22 | 40 | 88 | 104 | 192 | 3.10 |
|   | GB  |      | 22 | 40 | 88 | 104 | 62  |    |
| 5 | GSC |      | 22 | 40 | 88 | 104 | 166 | 1.89 |
|   | GB  |      | 22 | 40 | 88 | 104 | 88  |    |
| 6 | GSC |      | 22 | 40 | 88 | 104 | 126 | 0.98 |
|   | GB  |      | 22 | 40 | 88 | 104 | 128 |    |
| 7 | GSC |      | 22 | 40 | 88 | 104 | 144 | 1.31 |
|   | GB  |      | 22 | 40 | 88 | 104 | 110 |    |
| 8 | GSC |      | 22 | 40 | 88 | 104 | 104 | 0.69 |
|   | GB  |      | 22 | 40 | 88 | 104 | 150 |    |
| 9 | GSC |      | 22 | 40 | 88 | 104 | 150 | 1.44 |
|   | GB  |      | 22 | 40 | 88 | 104 | 104 |    |
| 10 | GSC |     | 22 | 40 | 88 | 104 | 110 | 0.76 |
|    | GB  |     | 22 | 40 | 88 | 104 | 144 |    |
| 11 | GSC |     | 22 | 40 | 88 | 104 | 128 | 1.02 |
|    | GB  |     | 22 | 40 | 88 | 104 | 126 |    |
| 12 | GSC |     | 22 | 40 | 88 | 104 | 88  | 0.53 |
|    | GB  |     | 22 | 40 | 88 | 104 | 166 |    |

FIG. 29A (continued)

| | | | | | | | |
|---|---|---|---|---|---|---|---|
| 13 | GSC | 22 | 40 | 88 | 104 | 62 | 0.32 |
| | GB | 22 | 40 | 88 | 104 | 192 | |
| 14 | GSC | 22 | 40 | 88 | 104 | 22 | 0.09 |
| | GB | 22 | 40 | 88 | 104 | 232 | |
| 15 | GSC | 22 | 40 | 88 | 104 | 40 | 0.19 |
| | GB | 22 | 40 | 88 | 104 | 214 | |
| 16 | GSC | 22 | 40 | 88 | 104 | 0 | NA |
| | GB | 22 | 40 | 88 | 104 | 254 | |
| 17 | GSC | 22 | 40 | 44/44 | 104 | 210 | 4.77 |
| | GB | 22 | 40 | 44/44 | 104 | 44 | |
| 18 | GSC | 22 | 40 | 44/44 | 104 | 170 | 2.02 |
| | GB | 22 | 40 | 44/44 | 104 | 84 | |
| 19 | GSC | 22 | 40 | 44/44 | 104 | 188 | 2.85 |
| | GB | 22 | 40 | 44/44 | 104 | 66 | |
| 20 | GSC | 22 | 40 | 44/44 | 104 | 148 | 1.40 |
| | GB | 22 | 40 | 44/44 | 104 | 106 | |
| 21 | GSC | 22 | 40 | 44/44 | 104 | 106 | 0.72 |
| | GB | 22 | 40 | 44/44 | 104 | 148 | |
| 22 | GSC | 22 | 40 | 44/44 | 104 | 66 | 0.35 |
| | GB | 22 | 40 | 44/44 | 104 | 188 | |
| 23 | GSC | 22 | 40 | 44/44 | 104 | 84 | 0.49 |
| | GB | 22 | 40 | 44/44 | 104 | 170 | |
| 24 | GSC | 22 | 40 | 44/44 | 104 | 44 | 0.21 |
| | GB | 22 | 40 | 44/44 | 104 | 210 | |
| 25 | GSC | 22 | 40 | 44/44 | 104 | 210 | 4.77 |
| | GB | 22 | 40 | 44/44 | 104 | 44 | |
| 26 | GSC | 22 | 40 | 44/44 | 104 | 170 | 2.02 |
| | GB | 22 | 40 | 44/44 | 104 | 84 | |
| 27 | GSC | 22 | 40 | 44/44 | 104 | 188 | 2.85 |

FIG. 29A (continued)

|    |     |    |    |       |       |     |      |
|----|-----|----|----|-------|-------|-----|------|
|    | GB  | 22 | 40 | 44/44 | 104   | 66  |      |
| 28 | GSC | 22 | 40 | 44/44 | 104   | 148 | 1.40 |
|    | GB  | 22 | 40 | 44/44 | 104   | 106 |      |
| 29 | GSC | 22 | 40 | 44/44 | 104   | 106 | 0.72 |
|    | GB  | 22 | 40 | 44/44 | 104   | 148 |      |
| 30 | GSC | 22 | 40 | 44/44 | 104   | 66  | 0.35 |
|    | GB  | 22 | 40 | 44/44 | 104   | 188 |      |
| 31 | GSC | 22 | 40 | 44/44 | 104   | 84  | 0.49 |
|    | GB  | 22 | 40 | 44/44 | 104   | 170 |      |
| 32 | GSC | 22 | 40 | 44/44 | 104   | 44  | 0.21 |
|    | GB  | 22 | 40 | 44/44 | 104   | 210 |      |
| 33 | GSC | 22 | 40 | 88    | 52/52 | 202 | 3.88 |
|    | GB  | 22 | 40 | 88    | 52/52 | 52  |      |
| 34 | GSC | 22 | 40 | 88    | 52/52 | 162 | 1.76 |
|    | GB  | 22 | 40 | 88    | 52/52 | 92  |      |
| 35 | GSC | 22 | 40 | 88    | 52/52 | 180 | 2.43 |
|    | GB  | 22 | 40 | 88    | 52/52 | 74  |      |
| 36 | GSC | 22 | 40 | 88    | 52/52 | 140 | 1.23 |
|    | GB  | 22 | 40 | 88    | 52/52 | 114 |      |
| 37 | GSC | 22 | 40 | 88    | 52/52 | 114 | 0.81 |
|    | GB  | 22 | 40 | 88    | 52/52 | 140 |      |
| 38 | GSC | 22 | 40 | 88    | 52/52 | 74  | 0.41 |
|    | GB  | 22 | 40 | 88    | 52/52 | 180 |      |
| 39 | GSC | 22 | 40 | 88    | 52/52 | 92  | 0.57 |
|    | GB  | 22 | 40 | 88    | 52/52 | 162 |      |
| 40 | GSC | 22 | 40 | 88    | 52/52 | 52  | 0.26 |
|    | GB  | 22 | 40 | 88    | 52/52 | 202 |      |
| 41 | GSC | 22 | 40 | 88    | 52/52 | 202 | 3.88 |
|    | GB  | 22 | 40 | 88    | 52/52 | 52  |      |

FIG. 29A (continued)

| | | | | | | | |
|---|---|---|---|---|---|---|---|
| 42 | GSC | 22 | 40 | 88 | 52/52 | 162 | 1.76 |
| | GB | 22 | 40 | 88 | 52/52 | 92 | |
| 43 | GSC | 22 | 40 | 88 | 52/52 | 180 | 2.43 |
| | GB | 22 | 40 | 88 | 52/52 | 74 | |
| 44 | GSC | 22 | 40 | 88 | 52/52 | 140 | 1.23 |
| | GB | 22 | 40 | 88 | 52/52 | 114 | |
| 45 | GSC | 22 | 40 | 88 | 52/52 | 114 | 0.81 |
| | GB | 22 | 40 | 88 | 52/52 | 140 | |
| 46 | GSC | 22 | 40 | 88 | 52/52 | 74 | 0.41 |
| | GB | 22 | 40 | 88 | 52/52 | 180 | |
| 47 | GSC | 22 | 40 | 88 | 52/52 | 94 | 0.59 |
| | GB | 22 | 40 | 88 | 52/52 | 160 | |
| 48 | GSC | 22 | 40 | 88 | 52/52 | 52 | 0.26 |
| | GB | 22 | 40 | 88 | 52/52 | 202 | |
| 49 | GSC | 22 | 40 | 44/44 | 52/52 | 158 | 1.65 |
| | GB | 22 | 40 | 44/44 | 52/52 | 96 | |
| 50 | GSC | 22 | 40 | 44/44 | 52/52 | 118 | 0.87 |
| | GB | 22 | 40 | 44/44 | 52/52 | 136 | |
| 51 | GSC | 22 | 40 | 44/44 | 52/52 | 136 | 1.15 |
| | GB | 22 | 40 | 44/44 | 52/52 | 118 | |
| 52 | GSC | 22 | 40 | 44/44 | 52/52 | 96 | 0.61 |
| | GB | 22 | 40 | 44/44 | 52/52 | 158 | |
| 53 | GSC | 22 | 40 | 44/44 | 52/52 | 158 | 1.65 |
| | GB | 22 | 40 | 44/44 | 52/52 | 96 | |
| 54 | GSC | 22 | 40 | 44/44 | 52/52 | 118 | 0.87 |
| | GB | 22 | 40 | 44/44 | 52/52 | 136 | |
| 55 | GSC | 22 | 40 | 44/44 | 52/52 | 136 | 1.15 |
| | GB | 22 | 40 | 44/44 | 52/52 | 118 | |

FIG. 29A

| | | | | | | | |
|---|---|---|---|---|---|---|---|
| 56 | GSC | 22 | 40 | 44/44 | 52/52 | 96 | 0.61 |
| | GB | 22 | 40 | 44/44 | 52/52 | 158 | |
| 57 | GSC | 22 | 40 | 44/44 | 52/52 | 158 | 1.65 |
| | GB | 22 | 40 | 44/44 | 52/52 | 96 | |
| 58 | GSC | 22 | 40 | 44/44 | 52/52 | 118 | 0.87 |
| | GB | 22 | 40 | 44/44 | 52/52 | 136 | |
| 59 | GSC | 22 | 40 | 44/44 | 52/52 | 136 | 1.15 |
| | GB | 22 | 40 | 44/44 | 52/52 | 118 | |
| 60 | GSC | 22 | 40 | 44/44 | 52/52 | 96 | 0.61 |
| | GB | 22 | 40 | 44/44 | 52/52 | 158 | |
| 61 | GSC | 22 | 40 | 44/44 | 52/52 | 158 | 1.65 |
| | GB | 22 | 40 | 44/44 | 52/52 | 96 | |
| 62 | GSC | 22 | 40 | 44/44 | 52/52 | 118 | 0.87 |
| | GB | 22 | 40 | 44/44 | 52/52 | 136 | |
| 63 | GSC | 22 | 40 | 44/44 | 52/52 | 136 | 1.15 |
| | GB | 22 | 40 | 44/44 | 52/52 | 118 | |
| 64 | GSC | 22 | 40 | 44/44 | 52/52 | 96 | 0.61 |
| | GB | 22 | 40 | 44/44 | 52/52 | 158 | |

| Cut-off | Asymmetry | Symmetry | Asymmetry (opposite) |
|---|---|---|---|
| 1.5 | 21 (32.8%) | 22 (34.4%) | 21 (32.8%) |
| 2 | 14 (21.9%) | 36 (56.2%) | 14 (21.9%) |
| 2.5 | 10 (15.6%) | 44 (68.8) | 10 (15.6%) |
| 3 | 8 (12.5%) | 48 (75%) | 8 (12.5%) |

FIG. 29B

| | | | X | Y | II | III | | X | Y | II | III | Sum G FP | GFP: GSC/GB |
|---|---|---|---|---|---|---|---|---|---|---|---|---|---|
| | | Mbps | 22 | 40 | 44 | 52 | Mbps | 22 | 40 | 44 | 52 | | |
| 1 | GSC | 80% GSC | 17.6 | 32 | 70.4 | 83.2 | 20% GSC | 4.4 | 8 | 17.6 | 20.8 | 208.2 | 4.00 |
| | GB | 80% GB | 17.6 | 32 | 70.4 | 83.2 | 20% GB | 4.4 | 8 | 17.6 | 20.8 | 50.8 | |
| 2 | GSC | 80% GSC | 17.6 | 32 | 70.4 | 83.2 | 20% GSC | 4.4 | 8 | 17.6 | 20.8 | 179.2 | 3.40 |
| | GB | 80% GB | 17.6 | 32 | 70.4 | 83.2 | 20% GB | 4.4 | 8 | 17.6 | 20.8 | 74.8 | |
| 3 | GSC | 80% GSC | 17.6 | 32 | 70.4 | 83.2 | 20% GSC | 4.4 | 8 | 17.6 | 20.8 | 190 | 2.97 |
| | GB | 80% GB | 17.6 | 32 | 70.4 | 83.2 | 20% GB | 4.4 | 8 | 17.6 | 20.8 | 64 | |
| 4 | GSC | 80% GSC | 17.6 | 32 | 70.4 | 83.2 | 20% GSC | 4.4 | 8 | 17.6 | 20.8 | 166 | 1.89 |
| | GB | 80% GB | 17.6 | 32 | 70.4 | 83.2 | 20% GB | 4.4 | 8 | 17.6 | 20.8 | 88 | |
| 5 | GSC | 80% GSC | 17.6 | 32 | 70.4 | 83.2 | 20% GSC | 4.4 | 8 | 17.6 | 20.8 | 150.4 | 1.45 |
| | GB | 80% GB | 17.6 | 32 | 70.4 | 83.2 | 20% GB | 4.4 | 8 | 17.6 | 20.8 | 103.6 | |
| 6 | GSC | 80% GSC | 17.6 | 32 | 70.4 | 83.2 | 20% GSC | 4.4 | 8 | 17.6 | 20.8 | 126.4 | 0.99 |
| | GB | 80% GB | 17.6 | 32 | 70.4 | 83.2 | 20% GB | 4.4 | 8 | 17.6 | 20.8 | 127.6 | |
| 7 | GSC | 80% GSC | 17.6 | 32 | 70.4 | 83.2 | 20% GSC | 4.4 | 8 | 17.6 | 20.8 | 137.2 | 1.17 |
| | GB | 80% GB | 17.6 | 32 | 70.4 | 83.2 | 20% GB | 4.4 | 8 | 17.6 | 20.8 | 116.8 | |

80% asymmetric deposition

FIG. 29B (continued)

| | | | | | | | | | | | | | |
|---|---|---|---|---|---|---|---|---|---|---|---|---|---|
| 8 | GSC | 80% GSC | 17.6 | 3 2 | 70.4 | 83.2 | 20% GSC | 4.4 | 8 | 17.6 | 20.8 | 113.2 | 0.80 |
| | GB | 80% GB | 17.6 | 3 2 | 70.4 | 83.2 | 20% GB | 4.4 | 8 | 17.6 | 20.8 | 140.8 | |
| 9 | GSC | 80% GSC | 17.6 | 3 2 | 70.4 | 83.2 | 20% GSC | 4.4 | 8 | 17.6 | 20.8 | 140.8 | 1.24 |
| | GB | 80% GB | 17.6 | 3 2 | 70.4 | 83.2 | 20% GB | 4.4 | 8 | 17.6 | 20.8 | 113.2 | |
| 10 | GSC | 80% GSC | 17.6 | 3 2 | 70.4 | 83.2 | 20% GSC | 4.4 | 8 | 17.6 | 20.8 | 116.8 | 0.85 |
| | GB | 80% GB | 17.6 | 3 2 | 70.4 | 83.2 | 20% GB | 4.4 | 8 | 17.6 | 20.8 | 137.2 | |
| 11 | GSC | 80% GSC | 17.6 | 3 2 | 70.4 | 83.2 | 20% GSC | 4.4 | 8 | 17.6 | 20.8 | 127.6 | 1.01 |
| | GB | 80% GB | 17.6 | 3 2 | 70.4 | 83.2 | 20% GB | 4.4 | 8 | 17.6 | 20.8 | 126.4 | |
| 12 | GSC | 80% GSC | 17.6 | 3 2 | 70.4 | 83.2 | 20% GSC | 4.4 | 8 | 17.6 | 20.8 | 103.6 | 0.69 |
| | GB | 80% GB | 17.6 | 3 2 | 70.4 | 83.2 | 20% GB | 4.4 | 8 | 17.6 | 20.8 | 150.4 | |
| 13 | GSC | 80% GSC | 17.6 | 3 2 | 70.4 | 83.2 | 20% GSC | 4.4 | 8 | 17.6 | 20.8 | 88 | |
| | GB | 80% GB | 17.6 | 3 2 | 70.4 | 83.2 | 20% GB | 4.4 | 8 | 17.6 | 20.8 | 166 | |
| 14 | GSC | 80% GSC | 17.6 | 3 2 | 70.4 | 83.2 | 20% GSC | 4.4 | 8 | 17.6 | 20.8 | 64 | |
| | GB | 80% GB | 17.6 | 3 2 | 70.4 | 83.2 | 20% GB | 4.4 | 8 | 17.6 | 20.8 | 190 | |
| 15 | GSC | 80% GSC | 17.6 | 3 2 | 70.4 | 83.2 | 20% GSC | 4.4 | 8 | 17.6 | 20.8 | 74.8 | |
| | GB | 80% GB | 17.6 | 3 2 | 70.4 | 83.2 | 20% GB | 4.4 | 8 | 17.6 | 20.8 | 179.2 | |
| 16 | GSC | 80% GSC | 17.6 | 3 2 | 70.4 | 83.2 | 20% GSC | 4.4 | 8 | 17.6 | 20.8 | 50.8 | |
| | GB | 80% GB | 17.6 | 3 2 | 70.4 | 83.2 | 20% GB | 4.4 | 8 | 17.6 | 20.8 | 203.2 | |

FIG. 29B (continued)

| | | | | | | | | | | | | | |
|---|---|---|---|---|---|---|---|---|---|---|---|---|---|
| 1 7 | GS C | 80% GSC | 17. 6 | 3 2 | 35.2/3 5.2 | 83.2 | 20% GSC | 4. 4 | 8 | 8.8/8 .8 | 20.8 | 176.8 | 2.29 |
| | GB | 80% GB | 17. 6 | 3 2 | 35.2/3 5.2 | 83.2 | 20% GB | 4. 4 | 8 | 8.8/8 .8 | 20.8 | 77.2 | |
| 1 8 | GS C | 80% GSC | 17. 6 | 3 2 | 35.2/3 5.2 | 83.2 | 20% GSC | 4. 4 | 8 | 8.8/8 .8 | 20.8 | 152.8 | 1.51 |
| | GB | 80% GB | 17. 6 | 3 2 | 35.2/3 5.2 | 83.2 | 20% GB | 4. 4 | 8 | 8.8/8 .8 | 20.8 | 101.2 | |
| 1 9 | GS C | 80% GSC | 17. 6 | 3 2 | 35.2/3 5.2 | 83.2 | 20% GSC | 4. 4 | 8 | 8.8/8 .8 | 20.8 | 163.6 | 1.81 |
| | GB | 80% GB | 17. 6 | 3 2 | 35.2/3 5.2 | 83.2 | 20% GB | 4. 4 | 8 | 8.8/8 .8 | 20.8 | 90.4 | |
| 2 0 | GS C | 80% GSC | 17. 6 | 3 2 | 35.2/3 5.2 | 83.2 | 20% GSC | 4. 4 | 8 | 8.8/8 .8 | 20.8 | 139.6 | 1.22 |
| | GB | 80% GB | 17. 6 | 3 2 | 35.2/3 5.2 | 83.2 | 20% GB | 4. 4 | 8 | 8.8/8 .8 | 20.8 | 114.4 | |
| 2 1 | GS C | 80% GSC | 17. 6 | 3 2 | 35.2/3 5.2 | 83.2 | 20% GSC | 4. 4 | 8 | 8.8/8 .8 | 20.8 | 114.4 | 0.82 |
| | GB | 80% GB | 17. 6 | 3 2 | 35.2/3 5.2 | 83.2 | 20% GB | 4. 4 | 8 | 8.8/8 .8 | 20.8 | 139.6 | |
| 2 2 | GS C | 80% GSC | 17. 6 | 3 2 | 35.2/3 5.2 | 83.2 | 20% GSC | 4. 4 | 8 | 8.8/8 .8 | 20.8 | 90.4 | 0.55 |
| | GB | 80% GB | 17. 6 | 3 2 | 35.2/3 5.2 | 83.2 | 20% GB | 4. 4 | 8 | 8.8/8 .8 | 20.8 | 163.6 | |
| 2 3 | GS C | 80% GSC | 17. 6 | 3 2 | 35.2/3 5.2 | 83.2 | 20% GSC | 4. 4 | 8 | 8.8/8 .8 | 20.8 | 101.2 | 0.66 |
| | GB | 80% GB | 17. 6 | 3 2 | 35.2/3 5.2 | 83.2 | 20% GB | 4. 4 | 8 | 8.8/8 .8 | 20.8 | 152.8 | |
| 2 4 | GS C | 80% GSC | 17. 6 | 3 2 | 35.2/3 5.2 | 83.2 | 20% GSC | 4. 4 | 8 | 8.8/8 .8 | 20.8 | 77.2 | 0.44 |
| | GB | 80% GB | 17. 6 | 3 2 | 35.2/3 5.2 | 83.2 | 20% GB | 4. 4 | 8 | 8.8/8 .8 | 20.8 | 176.8 | |
| 2 5 | GS C | 80% GSC | 17. 6 | 3 2 | 35.2/3 5.2 | 83.2 | 20% GSC | 4. 4 | 8 | 8.8/8 .8 | 20.8 | 176.8 | 2.29 |
| | GB | 80% GB | 17. 6 | 3 2 | 35.2/3 5.2 | 83.2 | 20% GB | 4. 4 | 8 | 8.8/8 .8 | 20.8 | 77.2 | |

FIG. 29B (continued)

| | | | | | | | | | | | | | |
|---|---|---|---|---|---|---|---|---|---|---|---|---|---|
| 2 6 | GS C | 80% GSC | 17.6 | 3 2 | 35.2/3 5.2 | 83.2 | 20% GSC | 4.4 | 8 | 8.8/8 .8 | 20.8 | 152.8 | 1.51 |
| | GB | 80% GB | 17.6 | 3 2 | 35.2/3 5.2 | 83.2 | 20% GB | 4.4 | 8 | 8.8/8 .8 | 20.8 | 101.2 | |
| 2 7 | GS C | 80% GSC | 17.6 | 3 2 | 35.2/3 5.2 | 83.2 | 20% GSC | 4.4 | 8 | 8.8/8 .8 | 20.8 | 163.6 | 1.81 |
| | GB | 80% GB | 17.6 | 3 2 | 35.2/3 5.2 | 83.2 | 20% GB | 4.4 | 8 | 8.8/8 .8 | 20.8 | 90.4 | |
| 2 8 | GS C | 80% GSC | 17.6 | 3 2 | 35.2/3 5.2 | 83.2 | 20% GSC | 4.4 | 8 | 8.8/8 .8 | 20.8 | 139.6 | 1.22 |
| | GB | 80% GB | 17.6 | 3 2 | 35.2/3 5.2 | 83.2 | 20% GB | 4.4 | 8 | 8.8/8 .8 | 20.8 | 114.4 | |
| 2 9 | GS C | 80% GSC | 17.6 | 3 2 | 35.2/3 5.2 | 83.2 | 20% GSC | 4.4 | 8 | 8.8/8 .8 | 20.8 | 114.4 | 0.82 |
| | GB | 80% GB | 17.6 | 3 2 | 35.2/3 5.2 | 83.2 | 20% GB | 4.4 | 8 | 8.8/8 .8 | 20.8 | 139.6 | |
| 3 0 | GS C | 80% GSC | 17.6 | 3 2 | 35.2/3 5.2 | 83.2 | 20% GSC | 4.4 | 8 | 8.8/8 .8 | 20.8 | 90.4 | 0.55 |
| | GB | 80% GB | 17.6 | 3 2 | 35.2/3 5.2 | 83.2 | 20% GB | 4.4 | 8 | 8.8/8 .8 | 20.8 | 163.6 | |
| 3 1 | GS C | 80% GSC | 17.6 | 3 2 | 35.2/3 5.2 | 83.2 | 20% GSC | 4.4 | 8 | 8.8/8 .8 | 20.8 | 101.2 | 0.66 |
| | GB | 80% GB | 17.6 | 3 2 | 35.2/3 5.2 | 83.2 | 20% GB | 4.4 | 8 | 8.8/8 .8 | 20.8 | 152.8 | |
| 3 2 | GS C | 80% GSC | 17.6 | 3 2 | 35.2/3 5.2 | 83.2 | 20% GSC | 4.4 | 8 | 8.8/8 .8 | 20.8 | 77.2 | 0.44 |
| | GB | 80% GB | 17.6 | 3 2 | 35.2/3 5.2 | 83.2 | 20% GB | 4.4 | 8 | 8.8/8 .8 | 20.8 | 176.8 | |
| 3 3 | GS C | 80% GSC | 17.6 | 3 2 | 70.4 | 41.6/4 1.6 | 20% GSC | 4.4 | 8 | 17.6 | 10.4/1 0.4 | 172 | 2.10 |
| | GB | 80% GB | 17.6 | 3 2 | 70.4 | 41.6/4 1.6 | 20% GB | 4.4 | 8 | 17.6 | 10.4/1 0.4 | 82 | |
| 3 4 | GS C | 80% GSC | 17.6 | 3 2 | 70.4 | 41.6/4 1.6 | 20% GSC | 4.4 | 8 | 17.6 | 10.4/1 0.4 | 148 | 1.40 |
| | GB | 80% GB | 17.6 | 3 2 | 70.4 | 41.6/4 1.6 | 20% GB | 4.4 | 8 | 17.6 | 10.4/1 0.4 | 106 | |

FIG. 29B (continued)

| | | | | | | | | | | | | | |
|---|---|---|---|---|---|---|---|---|---|---|---|---|---|
| 3 5 | GS C | 80% GSC | 17.6 | 3 2 | 70.4 | 41.6/4 1.6 | 20% GSC | 4.4 | 8 | 17.6 | 10.4/1 0.4 | 158.8 | 1.67 |
| | GB | 80% GB | 17.6 | 3 2 | 70.4 | 41.6/4 1.6 | 20% GB | 4.4 | 8 | 17.6 | 10.4/1 0.4 | 95.2 | |
| 3 6 | GS C | 80% GSC | 17.6 | 3 2 | 70.4 | 41.6/4 1.6 | 20% GSC | 4.4 | 8 | 17.6 | 10.4/1 0.4 | 134.8 | 1.13 |
| | GB | 80% GB | 17.6 | 3 2 | 70.4 | 41.6/4 1.6 | 20% GB | 4.4 | 8 | 17.6 | 10.4/1 0.4 | 119.2 | |
| 3 7 | GS C | 80% GSC | 17.6 | 3 2 | 70.4 | 41.6/4 1.6 | 20% GSC | 4.4 | 8 | 17.6 | 10.4/1 0.4 | 119.2 | 0.88 |
| | GB | 80% GB | 17.6 | 3 2 | 70.4 | 41.6/4 1.6 | 20% GB | 4.4 | 8 | 17.6 | 10.4/1 0.4 | 134.8 | |
| 3 8 | GS C | 80% GSC | 17.6 | 3 2 | 70.4 | 41.6/4 1.6 | 20% GSC | 4.4 | 8 | 17.6 | 10.4/1 0.4 | 95.2 | |
| | GB | 80% GB | 17.6 | 3 2 | 70.4 | 41.6/4 1.6 | 20% GB | 4.4 | 8 | 17.6 | 10.4/1 0.4 | 158.8 | |
| 3 9 | GS C | 80% GSC | 17.6 | 3 2 | 70.4 | 41.6/4 1.6 | 20% GSC | 4.4 | 8 | 17.6 | 10.4/1 0.4 | 106 | 0.72 |
| | GB | 80% GB | 17.6 | 3 2 | 70.4 | 41.6/4 1.6 | 20% GB | 4.4 | 8 | 17.6 | 10.4/1 0.4 | 148 | |
| 4 0 | GS C | 80% GSC | 17.6 | 3 2 | 70.4 | 41.6/4 1.6 | 20% GSC | 4.4 | 8 | 17.6 | 10.4/1 0.4 | 82 | |
| | GB | 80% GB | 17.6 | 3 2 | 70.4 | 41.6/4 1.6 | 20% GB | 4.4 | 8 | 17.6 | 10.4/1 0.4 | 172 | |
| 4 1 | GS C | 80% GSC | 17.6 | 3 2 | 70.4 | 41.6/4 1.6 | 20% GSC | 4.4 | 8 | 17.6 | 10.4/1 0.4 | 172 | 2.10 |
| | GB | 80% GB | 17.6 | 3 2 | 70.4 | 41.6/4 1.6 | 20% GB | 4.4 | 8 | 17.6 | 10.4/1 0.4 | 82 | |
| 4 2 | GS C | 80% GSC | 17.6 | 3 2 | 70.4 | 41.6/4 1.6 | 20% GSC | 4.4 | 8 | 17.6 | 10.4/1 0.4 | 148 | 1.40 |
| | GB | 80% GB | 17.6 | 3 2 | 70.4 | 41.6/4 1.6 | 20% GB | 4.4 | 8 | 17.6 | 10.4/1 0.4 | 106 | |
| 4 3 | GS C | 80% GSC | 17.6 | 3 2 | 70.4 | 41.6/4 1.6 | 20% GSC | 4.4 | 8 | 17.6 | 10.4/1 0.4 | 158.8 | 1.67 |
| | GB | 80% GB | 17.6 | 3 2 | 70.4 | 41.6/4 1.6 | 20% GB | 4.4 | 8 | 17.6 | 10.4/1 0.4 | 95.2 | |

FIG. 29B (continued)

| | | | | | | | | | | | | | |
|---|---|---|---|---|---|---|---|---|---|---|---|---|---|
| 4 4 | GS C | 80% GSC | 17.6 | 3 2 | 70.4 | 41.6/4 1.6 | 20% GSC | 4.4 | 8 | 17.6 | 10.4/1 0.4 | 134.8 | 1.13 |
| | GB | 80% GB | 17.6 | 3 2 | 70.4 | 41.6/4 1.6 | 20% GB | 4.4 | 8 | 17.6 | 10.4/1 0.4 | 119.2 | |
| 4 5 | GS C | 80% GSC | 17.6 | 3 2 | 70.4 | 41.6/4 1.6 | 20% GSC | 4.4 | 8 | 17.6 | 10.4/1 0.4 | 119.2 | 0.88 |
| | GB | 80% GB | 17.6 | 3 2 | 70.4 | 41.6/4 1.6 | 20% GB | 4.4 | 8 | 17.6 | 10.4/1 0.4 | 134.8 | |
| 4 6 | GS C | 80% GSC | 17.6 | 3 2 | 70.4 | 41.6/4 1.6 | 20% GSC | 4.4 | 8 | 17.6 | 10.4/1 0.4 | 95.2 | * |
| | GB | 80% GB | 17.6 | 3 2 | 70.4 | 41.6/4 1.6 | 20% GB | 4.4 | 8 | 17.6 | 10.4/1 0.4 | 158.8 | |
| 4 7 | GS C | 80% GSC | 17.6 | 3 2 | 70.4 | 41.6/4 1.6 | 20% GSC | 4.4 | 8 | 17.6 | 10.4/1 0.4 | 106 | 0.72 |
| | GB | 80% GB | 17.6 | 3 2 | 70.4 | 41.6/4 1.6 | 20% GB | 4.4 | 8 | 17.6 | 10.4/1 0.4 | 148 | |
| 4 8 | GS C | 80% GSC | 17.6 | 3 2 | 70.4 | 41.6/4 1.6 | 20% GSC | 4.4 | 8 | 17.6 | 10.4/1 0.4 | 82 | * |
| | GB | 80% GB | 17.6 | 3 2 | 70.4 | 41.6/4 1.6 | 20% GB | 4.4 | 8 | 17.6 | 10.4/1 0.4 | 172 | |
| 4 9 | GS C | 80% GSC | 17.6 | 3 2 | 35.2/3 5.2 | 41.6/4 1.6 | 20% GSC | 4.4 | 8 | 8.8/8 .8 | 10.4/1 0.4 | 145.6 | 1.34 |
| | GB | 80% GB | 17.6 | 3 2 | 35.2/3 5.2 | 41.6/4 1.6 | 20% GB | 4.4 | 8 | 8.8/8 .8 | 10.4/1 0.4 | 108.4 | |
| 5 0 | GS C | 80% GSC | 17.6 | 3 2 | 35.2/3 5.2 | 41.6/4 1.6 | 20% GSC | 4.4 | 8 | 8.8/8 .8 | 10.4/1 0.4 | 121.6 | 0.92 |
| | GB | 80% GB | 17.6 | 3 2 | 35.2/3 5.2 | 41.6/4 1.6 | 20% GB | 4.4 | 8 | 8.8/8 .8 | 10.4/1 0.4 | 132.4 | |
| 5 1 | GS C | 80% GSC | 17.6 | 3 2 | 35.2/3 5.2 | 41.6/4 1.6 | 20% GSC | 4.4 | 8 | 8.8/8 .8 | 10.4/1 0.4 | 132.4 | 1.09 |
| | GB | 80% GB | 17.6 | 3 2 | 35.2/3 5.2 | 41.6/4 1.6 | 20% GB | 4.4 | 8 | 8.8/8 .8 | 10.4/1 0.4 | 121.6 | |
| 5 2 | GS C | 80% GSC | 17.6 | 3 2 | 35.2/3 5.2 | 41.6/4 1.6 | 20% GSC | 4.4 | 8 | 8.8/8 .8 | 10.4/1 0.4 | 108.4 | 0.74 |
| | GB | 80% GB | 17.6 | 3 2 | 35.2/3 5.2 | 41.6/4 1.6 | 20% GB | 4.4 | 8 | 8.8/8 .8 | 10.4/1 0.4 | 145.6 | |

FIG. 29B (continued)

| | | | | | | | | | | | | | |
|---|---|---|---|---|---|---|---|---|---|---|---|---|---|
| 5 3 | GS C | 80% GSC | 17.6 | 3 2 | 35.2/3 5.2 | 41.6/4 1.6 | 20% GSC | 4.4 | 8 | 8.8/8 .8 | 10.4/1 0.4 | 145.6 | 1.34 |
| | GB | 80% GB | 17.6 | 3 2 | 35.2/3 5.2 | 41.6/4 1.6 | 20% GB | 4.4 | 8 | 8.8/8 .8 | 10.4/1 0.4 | 108.4 | |
| 5 4 | GS C | 80% GSC | 17.6 | 3 2 | 35.2/3 5.2 | 41.6/4 1.6 | 20% GSC | 4.4 | 8 | 8.8/8 .8 | 10.4/1 0.4 | 121.6 | 0.92 |
| | GB | 80% GB | 17.6 | 3 2 | 35.2/3 5.2 | 41.6/4 1.6 | 20% GB | 4.4 | 8 | 8.8/8 .8 | 10.4/1 0.4 | 132.4 | |
| 5 5 | GS C | 80% GSC | 17.6 | 3 2 | 35.2/3 5.2 | 41.6/4 1.6 | 20% GSC | 4.4 | 8 | 8.8/8 .8 | 10.4/1 0.4 | 132.4 | 1.09 |
| | GB | 80% GB | 17.6 | 3 2 | 35.2/3 5.2 | 41.6/4 1.6 | 20% GB | 4.4 | 8 | 8.8/8 .8 | 10.4/1 0.4 | 121.6 | |
| 5 6 | GS C | 80% GSC | 17.6 | 3 2 | 35.2/3 5.2 | 41.6/4 1.6 | 20% GSC | 4.4 | 8 | 8.8/8 .8 | 10.4/1 0.4 | 108.4 | 0.74 |
| | GB | 80% GB | 17.6 | 3 2 | 35.2/3 5.2 | 41.6/4 1.6 | 20% GB | 4.4 | 8 | 8.8/8 .8 | 10.4/1 0.4 | 145.6 | |
| 5 7 | GS C | 80% GSC | 17.6 | 3 2 | 35.2/3 5.2 | 41.6/4 1.6 | 20% GSC | 4.4 | 8 | 8.8/8 .8 | 10.4/1 0.4 | 145.6 | 1.34 |
| | GB | 80% GB | 17.6 | 3 2 | 35.2/3 5.2 | 41.6/4 1.6 | 20% GB | 4.4 | 8 | 8.8/8 .8 | 10.4/1 0.4 | 108.4 | |
| 5 8 | GS C | 80% GSC | 17.6 | 3 2 | 35.2/3 5.2 | 41.6/4 1.6 | 20% GSC | 4.4 | 8 | 8.8/8 .8 | 10.4/1 0.4 | 121.6 | 0.92 |
| | GB | 80% GB | 17.6 | 3 2 | 35.2/3 5.2 | 41.6/4 1.6 | 20% GB | 4.4 | 8 | 8.8/8 .8 | 10.4/1 0.4 | 132.4 | |
| 5 9 | GS C | 80% GSC | 17.6 | 3 2 | 35.2/3 5.2 | 41.6/4 1.6 | 20% GSC | 4.4 | 8 | 8.8/8 .8 | 10.4/1 0.4 | 132.4 | 1.09 |
| | GB | 80% GB | 17.6 | 3 2 | 35.2/3 5.2 | 41.6/4 1.6 | 20% GB | 4.4 | 8 | 8.8/8 .8 | 10.4/1 0.4 | 121.6 | |
| 6 0 | GS C | 80% GSC | 17.6 | 3 2 | 35.2/3 5.2 | 41.6/4 1.6 | 20% GSC | 4.4 | 8 | 8.8/8 .8 | 10.4/1 0.4 | 108.4 | 0.74 |
| | GB | 80% GB | 17.6 | 3 2 | 35.2/3 5.2 | 41.6/4 1.6 | 20% GB | 4.4 | 8 | 8.8/8 .8 | 10.4/1 0.4 | 145.6 | |
| 6 1 | GS C | 80% GSC | 17.6 | 3 2 | 35.2/3 5.2 | 41.6/4 1.6 | 20% GSC | 4.4 | 8 | 8.8/8 .8 | 10.4/1 0.4 | 145.6 | 1.34 |
| | GB | 80% GB | 17.6 | 3 2 | 35.2/3 5.2 | 41.6/4 1.6 | 20% GB | 4.4 | 8 | 8.8/8 .8 | 10.4/1 0.4 | 108.4 | |

FIG. 29B (continued)

H3T3A MUTANT PROTEIN EFFICIENTLY REDUCES H3T3P AND CAUSES INCREASED CELL DEATH OF RAPIDLY DIVIDING CELLS

CROSS-REFERENCE TO RELATED APPLICATIONS

This application is a National Phase of PCT Application No. PCT/US2016/026114, filed Apr. 6, 2016 and claims priority to and the benefit of U.S. Provisional Application No. 62/143,546, filed Apr. 6, 2015, the entire contents of which applications are incorporated by reference herein in its entirety.

STATEMENT OF RIGHTS TO INVENTIONS MADE UNDER FEDERALLY SPONSORED RESEARCH

This work was supported by the National Institute of Child Health and Human Development under grant number R21HD065089 and by the National Institutes of Health under grant numbers R01HD065816 and R01GM112008. The Government has certain rights in this invention.

SEQUENCE LISTING

The instant application contains a Sequence Listing in electronic format. The Sequence Listing is entitled "048317_469001WO_Seq_Listing_2016_04_06", was created on Apr. 6, 2016 and is 20 KB in size. The information in the electronic format of the Sequence Listing is part of the present application and is incorporated herein by reference in its entirety.

FIELD OF THE INVENTION

This invention relates generally to the field of cell cycle arrest.

BACKGROUND OF THE INVENTION

Cancer is one of the most prevalent diseases, accounting for 25% of all deaths in the United States. As such, prior to the invention described herein, there was a pressing need to develop new strategies to inhibit rapidly dividing cancer cells.

SUMMARY OF THE INVENTION

The invention is based, at least in part, on the surprising discovery that histone H3 threonine 3 phosphorylation regulates asymmetric H3 inheritance and male germline activity in Drosophila and that an H3T3A mutant protein efficiently reduces H3T3P and causes increased cell death of rapidly-dividing cells. The methods described herein introduce a point mutation of the Thr3 residue of the transgenic histone H3 protein to reduce the post-translational modification of H3 (i.e., to reduce the H3T3 phosphorylation in rapidly dividing cells) to cause cell cycle arrest followed by cell death. Specifically, a transgene that carries a mutation that converts threonine 3 (Thr3 or T3) to the unphosphorylatable alanine (Ala or A) greatly reduces the phosphorylation at T3 of histone 3 (H3T3P) mark. Furthermore, converting T3 to the unphosphorylatable residue alanine (H3T3A) or to the phosphomimetic aspartate (H3T3D) disrupts assymetric H3 inheritance. The H3T3P mark is important for mitosis, and the reduction of which leads to increased cell death in rapidly-divising cells including cancer cells.

As such, the compositions and methods described herein antagonize growth in rapidly dividing cells. For example, the compositions described herein are anti-cancer agents, e.g., H3T3A and/or H3T3D, that are utilized in methods to reduce tumor cell growth.

Described herein are methods of inducing cell death in a rapidly dividing cell comprising contacting a rapidly dividing cell with an agent that reduces phosphorylation at threonine 3 of histone 3 (H3T3P), thereby inducing cell cycle arrest followed by cell death. In some cases, the rapidly dividing cell is a tumor cell, e.g., a cancer cell. Preferably, the rapidly dividing cell is not a germline stem cell. Similarly, methods of inhibiting tumor growth are carried out by contacting a tumor cell with an agent that reduces phosphorylation at threonine 3 of histone 3 (H3T3P), thereby inhibiting tumor growth.

The agent that reduces phosphorylation of H3T3P comprises an H3T3A mutant protein, e.g., a mutant transgenic protein. For example, the H3T3A mutant protein comprises a point mutation of threonine 3 of H3 such as a substitution of threonine 3 with alanine (H3T3A). In other embodiments, the agent that reduces phosphorylation of H3T3P comprises an H3T3D mutant protein, e.g., a mutant transgenic protein. For example, the H3T3D mutant protein comprises a point mutation of threonine 3 of H3 such as a substitution of threonine 3 with aspartic acid (H3T3D). In some cases, the method further comprises administering a chemotherapeutic agent such as radiotherapy or a cell death-inducing agent.

Also described herein are isolated transgenes encoding H3T3A and isolated peptides comprising H3T3A. Additionally, described herein are isolated transgenes encoding H3T3D and isolated peptides comprising H3T3D.

The nucleic acid sequence of wild type Drosophila melanogaster histone H3 is set forth below (SEQ ID NO: 1).

```
ATGGCTCGTACCAAGCAAACTGCTCGCAAATCGACTGGTGGAAAGGCGCC
ACGCAAACAACTGGCTACTAAGGCCGCTCGCAAGAGTGCTCCAGCCACCG
GAGGTGTGAAGAAGCCCCACCGCTATCGCCCTGGAACCGTGGCCTTGCGT
GAAATTCGTCGCTACCAAAAGAGCACCGAGCTTCTAATCCGCAAGCTGCC
TTTCCAGCGTCTGGTGCGTGAAATCGCTCAGGACTTTAAGACGGACTTGC
GATTCCAGAGCTCGGCGGTTATGGCTCTGCAGGAAGCTAGCGAAGCCTAC
CTGGTTGGTCTCTTCGAAGATACCAACTTGTGTGCCATTCATGCCAAGCG
TATCACCATAATGCCCAAAGACATCCAGTTAGCGCGACGCATTCGCGGCG
AGCGTGCTTAA
```

The nucleic acid sequence of Drosophila melanogaster H3T3A mutant is set forth below (SEQ ID NO: 2).

```
ATGGCTCGTGCCAAGCAAACTGCTCGCAAATCGACTGGTGGAAAGGCGCC
ACGCAAACAACTGGCTACTAAGGCCGCTCGCAAGAGTGCTCCAGCCACCG
GAGGTGTGAAGAAGCCCCACCGCTATCGCCCTGGAACCGTGGCCTTGCGT
GAAATTCGTCGCTACCAAAAGAGCACCGAGCTTCTAATCCGCAAGCTGCC
TTTCCAGCGTCTGGTGCGTGAAATCGCTCAGGACTTTAAGACGGACTTGC
```

GATTCCAGAGCTCGGCGGTTATGGCTCTGCAGGAAGCTAGCGAAGCCTAC

CTGGTTGGTCTCTTCGAAGATACCAACTTGTGTGCCATTCATGCCAAGCG

TATCACCATAATGCCCAAAGACATCCAGTTAGCGCGACGCATTCGCGGCG

AGCGTGCTTAA

The nucleic acid sequence of *Drosophila melanogaster* H3T3D mutant is set forth below (SEQ ID NO: 13).

ATGGCTCGTGACAAGCAAACTGCTCGCAAATCGACTGGTGGAAAGGCGCC

ACGCAAACAACTGGCTACTAAGGCCGCTCGCAAGAGTGCTCCAGCCACCG

GAGGTGTGAAGAAGCCCCACCGCTATCGCCCTGGAACCTGGCCTTGCGT

GAAATTCGTCGCTACCAAAAGAGCACCGAGCTTCTAATCCGCAAGCTGCC

TTTCCAGCGTCTGGTGCGTGAAATCGCTCAGGACTTTAAGACGGACTTGC

GATTCCAGAGCTCGGCGGTTATGGCTCTGCAGGAAGCTAGCGAAGCCTAC

CTGGTTGGTCTCTTCGAAGATACCAACTTGTGTGCCATTCATGCCAAGCG

TATCACCATAATGCCCAAAGACATCCAGTTAGCGCGACGCATTCGCGGCG

AGCGTGCTTAA

The nucleic acid sequence of wild type human histone H3 is set forth below (SEQ ID NO: 3).

ATGGCCCGAACCAAGCAGACTGCGCGCAAGTCAACGGGTGGCAAGGCGCC

GCGCAAGCAGCTGGCCACCAAGGTGGCTCGCAAGAGCGCACCTGCCACTG

GCGGCGTGAAGAAGCCGCACCGCTACCGGCCCGGCACGGTGGCGCTTCGC

GAGATCCGCCGCTACCAGAAGTCCACTGAGCTGCTAATCCGCAAGTTGCC

CTTCCAGCGGCTGATGCGCGAGATCGCTCAGGACTTTAAGACCGACCTGC

GCTTCCAGAGCTCGGCCGTGATGGCGCTGCAGGAGGCGTGCGAGTCTTAC

CTGGTGGGCTGTTTGAGGACACCAACCTGTGTGTCATCCATGCCAAACG

GGTCACCATCATGCCTAAGGACATCCAGCTGGCACGCCGTATCCGCGGGG

AGCGGGCCTAG

The nucleic acid sequence of human H3T3A mutant is set forth below (SEQ ID NO: 4).

ATGGCCCGAGCCAAGCAGACTGCGCGCAAGTCAACGGGTGGCAAGGCGCC

GCGCAAGCAGCTGGCCACCAAGGTGGCTCGCAAGAGCGCACCTGCCACTG

GCGGCGTGAAGAAGCCGCACCGCTACCGGCCCGGCACGGTGGCGCTTCGC

GAGATCCGCCGCTACCAGAAGTCCACTGAGCTGCTAATCCGCAAGTTGCC

CTTCCAGCGGCTGATGCGCGAGATCGCTCAGGACTTTAAGACCGACCTGC

GCTTCCAGAGCTCGGCCGTGATGGCGCTGCAGGAGGCGTGCGAGTCTTAC

CTGGTGGGCTGTTTGAGGACACCAACCTGTGTGTCATCCATGCCAAACG

GGTCACCATCATGCCTAAGGACATCCAGCTGGCACGCCGTATCCGCGGGG

AGCGGGCCTAG

The nucleic acid sequence of human H3T3D mutant is set forth below (SEQ ID NO: 14).

ATGGCCCGAGACCAAGCAGACTGCGCGCAAGTCAACGGGTGGCAAGGCGC

CGCGCAAGCAGCTGGCCACCAAGGTGGCTCGCAAGAGCGCACCTGCCACT

GGCGGCGTGAAGAAGCCGCACCGCTACCGGCCCGGCACGGTGGCGCTTCG

CGAGATCCGCCGCTACCAGAAGTCCACTGAGCTGCTAATCCGCAAGTTGC

CCTTCCAGCGGCTGATGCGCGAGATCGCTCAGGACTTTAAGACCGACCTG

CGCTTCCAGAGCTCGGCCGTGATGGCGCTGCAGGAGGCGTGCGAGTCTTA

CCTGGTGGGCTGTTTGAGGACACCAACCTGTGTGTCATCCATGCCAAAC

GGGTCACCATCATGCCTAAGGACATCCAGCTGGCACGCCGTATCCGCGGG

GAGCGGGCCTAG

The nucleic acid sequence of wild type *Mus Musculus* H3 is set forth below (SEQ ID NO: 5).

ATGGCTCGTACTAAGCAGACCGCTCGCAAGTCTACCGGCGGCAAGGCCCC

GCGCAAGCAGCTGGCCACCAAGGCCGCCCGCAAGAGCGCCCCGGCCACCG

GCGGCGTGAAGAAGCCTCACCGCTACCGTCCCGGCACTGTGGCACTGCGC

GAGATCCGGCGCTACCAGAAGTCGACCGAGCTGCTGATCCGCAAGCTGCC

GTTCCAGCGCCTGGTGCGCGAGATCGCGCAGGACTTCAAGACCGACCTGC

GCTTCCAGAGCTCGGCCGTCATGGCTCTGCAGGAGGCCTGTGAGGCCTAC

CTCGTGGGTCTGTTTGAGGACACCAACCTGTGCGCCATCCACGCCAAGCG

TGTCACCATCATGCCCAAGGACATCCAGCTGGCCCGTCGCATCCGCGGGG

AGAGGGCTTAA

The nucleic acid sequence of *Mus Musculus* H3T3A mutant is set forth below (SEQ ID NO: 6).

ATGGCTCGTGCTTAAGCAGACCGCTCGCAAGTCTACCGGCGGCAAGGCCC

CGCGCAAGCAGCTGGCCACCAAGGCCGCCCGCAAGAGCGCCCCGGCCACC

GGCGGCGTGAAGAAGCCTCACCGCTACCGTCCCGGCACTGTGGCACTGCG

CGAGATCCGGCGCTACCAGAAGTCGACCGAGCTGCTGATCCGCAAGCTGC

CGTTCCAGCGCCTGGTGCGCGAGATCGCGCAGGACTTCAAGACCGACCTG

CGCTTCCAGAGCTCGGCCGTCATGGCTCTGCAGGAGGCCTGTGAGGCCTA

CCTCGTGGGTCTGTTTGAGGACACCAACCTGTGCGCCATCCACGCCAAGC

GTGTCACCATCATGCCCAAGGACATCCAGCTGGCCCGTCGCATCCGCGGG

GAGAGGGCTTAA

The nucleic acid sequence of *Mus Musculus* H3T3D mutant is set forth below (SEQ ID NO: 15).

ATGGCTCGTGACCAAGCAGACCGCTCGCAAGTCTACCGGCGGCAAGGCCC

CGCGCAAGCAGCTGGCCACCAAGGCCGCCCGCAAGAGCGCCCCGGCCACC

GGCGGCGTGAAGAAGCCTCACCGCTACCGTCCCGGCACTGTGGCACTGCG

CGAGATCCGGCGCTACCAGAAGTCGACCGAGCTGCTGATCCGCAAGCTGC

CGTTCCAGCGCCTGGTGCGCGAGATCGCGCAGGACTTCAAGACCGACCTG

CGCTTCCAGAGCTCGGCCGTCATGGCTCTGCAGGAGGCCTGTGAGGCCTA

CCTCGTGGGTCTGTTTGAGGACACCAACCTGTGCGCCATCCACGCCAAGC

-continued

GTGTCACCATCATGCCCAAGGACATCCAGCTGGCCCGTCGCATCCGCGGG

GAGAGGGCTTAA

The amino acid sequence of wild type *Drosophila melanogaster* histone H3 is set forth below (SEQ ID NO: 7).

MARTKQTARKSTGGKAPRKQLATKAARKSAPATGGVKKPHRYRPGTVALR

EIRRYQKSTELLIRKLPFQRLVREIAQDFKTDLRFQSSAVMALQEASEAY

LVGLFEDTNLCAIHAKRVTIMPKDIQLARRIRGERA

The amino acid sequence of *Drosophila melanogaster* H3T3A mutant is set forth below (SEQ ID NO: 8).

MARAKQTARKSTGGKAPRKQLATKAARKSAPATGGVKKPHRYRPGTVALR

EIRRYQKSTELLIRKLPFQRLVREIAQDFKTDLRFQSSAVMALQEASEAY

LVGLFEDTNLCAIHAKRVTIMPKDIQLARRIRGERA

The amino acid sequence of *Drosophila melanogaster* H3T3D mutant is set forth below (SEQ ID NO: 16).

MARDKQTARKSTGGKAPRKQLATKAARKSAPATGGVKKPHRYRPGTVALR

EIRRYQKSTELLIRKLPFQRLVREIAQDFKTDLRFQSSAVMALQEASEAY

LVGLFEDTNLCAIHAKRVTIMPKDIQLARRIRGERA

The amino acid sequence of wild type human histone H3 is set forth below (SEQ ID NO: 9).

MARTKQTARKSTGGKAPRKQLATKAARKSAPATGGVKKPHRYRPGTVALR

EIRRYQKSTELLIRKLPFQRLVREIAQDFKTDLRFQSSAVMALQEACEAY

LVGLFEDTNLCAIHAKRVTIMPKDIQLARRIRGERA

The amino acid sequence of human H3T3A mutant is set forth below (SEQ ID NO: 10).

MARAKQTARKSTGGKAPRKQLATKAARKSAPATGGVKKPHRYRPGTVALR

EIRRYQKSTELLIRKLPFQRLVREIAQDFKTDLRFQSSAVMALQEACEAY

LVGLFEDTNLCAIHAKRVTIMPKDIQLARRIRGERA

The amino acid sequence of human H3T3D mutant is set forth below (SEQ ID NO: 17).

MARDKQTARKSTGGKAPRKQLATKAARKSAPATGGVKKPHRYRPGTVALR

EIRRYQKSTELLIRKLPFQRLVREIAQDFKTDLRFQSSAVMALQEACEAY

LVGLFEDTNLCAIHAKRVTIMPKDIQLARRIRGERA

The amino acid sequence of wild type *Mus Musculus* histone H3 is set forth below (SEQ ID NO: 11).

MARTKQTARKSTGGKAPRKQLATKAARKSAPATGGVKKPHRYRPGTVALR

EIRRYQKSTELLIRKLPFQRLVREIAQDFKTDLRFQSSAVMALQEACEAY

LVGLFEDTNLCAIHAKRVTIMPKDIQLARRIRGERA

The amino acid sequence of *Mus Musculus* H3T3A mutant is set forth below (SEQ ID NO: 12).

MARAKQTARKSTGGKAPRKQLATKAARKSAPATGGVKKPHRYRPGTVALR

EIRRYQKSTELLIRKLPFQRLVREIAQDFKTDLRFQSSAVMALQEACEAY

LVGLFEDTNLCAIHAKRVTIMPKDIQLARRIRGERA

The amino acid sequence of *Mus Musculus* H3T3D mutant is set forth below (SEQ ID NO: 18).

MARDKQTARKSTGGKAPRKQLATKAARKSAPATGGVKKPHRYRPGTVALR

EIRRYQKSTELLIRKLPFQRLVREIAQDFKTDLRFQSSAVMALQEACEAY

LVGLFEDTNLCAIHAKRVTIMPKDIQLARRIRGERA

Also provided are kits for arresting cell cycle comprising an agent that reduces phosphorylation H3T3P. Suitable agents that reduce phosphorylation H3T3P comprises an H3T3A mutant protein comprising a substitution of threonine 3 with alanine (H3T3A). In other embodiments, suitable agents that reduce phosphorylation H3T3P comprise an H3T3D mutant protein comprising a substitution of threonine 3 with aspartic acid (H3T3D).

The methods described herein are useful as anti-cancer agents to inhibit tumor growth in a subject. The subject is preferably a mammal in need of such treatment, e.g., a subject that has been diagnosed with cancer or a predisposition thereto. The mammal is any mammal, e.g., a human, a primate, a mouse, a rat, a dog, a cat, a horse, as well as livestock or animals grown for food consumption, e.g., cattle, sheep, pigs, chickens, and goats. In a preferred embodiment, the mammal is a human.

The methods described herein are useful in treating, delaying the progression of, preventing relapse of or alleviating a symptom of a cancer or other neoplastic or pre-neoplastic condition. For example, the methods described herein are useful in treating hematological malignancies and/or tumors. The methods described herein are also useful in treating non-Hodgkin's lymphoma (NHL), acute lymphocytic leukemia (ALL), acute myeloid leukemia (AML), chronic lymphocytic leukemia (CLL), chronic myelogenous leukemia (CML), multiple myeloma (MM), breast cancer, ovarian cancer, head and neck cancer, bladder cancer, melanoma, colorectal cancer, pancreatic cancer, lung cancer, leiomyoma, leiomyosarcoma, glioma, glioblastoma, and so on. Solid tumors include, e.g., breast tumors, ovarian tumors, lung tumors, pancreatic tumors, prostate tumors, melanoma tumors, colorectal tumors, lung tumors, head and neck tumors, bladder tumors, esophageal tumors, liver tumors, and kidney tumors.

In some cases, the methods described herein are used in conjunction with one or more agents or a combination of additional agents, e.g., an anti-cancer agent. Suitable agents include current pharmaceutical and/or surgical therapies for an intended application, such as, for example, cancer. For example, the methods described herein can be used in conjunction with one or more chemotherapeutic or antineoplastic agents. In some cases, the additional chemotherapeutic agent is radiotherapy. In some cases, the chemotherapeutic agent is a cell death-inducing agent.

The term "antineoplastic agent" is used herein to refer to agents that have the functional property of inhibiting a development or progression of a neoplasm in a human, particularly a malignant (cancerous) lesion, such as a carcinoma, sarcoma, lymphoma, or leukemia. Inhibition of metastasis is frequently a property of antineoplastic agents.

In some cases, a composition of the invention is administered orally or systemically. Other modes of administration include rectal, topical, intraocular, buccal, intravaginal, intracisternal, intracerebroventricular, intratracheal, nasal, transdermal, within/on implants, or parenteral routes. The term "parenteral" includes subcutaneous, intrathecal, intravenous, intramuscular, intraperitoneal, or infusion. Intravenous or intramuscular routes are not particularly suitable for long-term therapy and prophylaxis. They could, however, be preferred in emergency situations. Compositions comprising a composition of the invention can be added to a physiological fluid, such as blood. Oral administration can be preferred for prophylactic treatment because of the convenience to the patient as well as the dosing schedule. Parenteral modalities (subcutaneous or intravenous) may be preferable for more acute illness, or for therapy in patients that are unable to tolerate enteral administration due to gastrointestinal intolerance, ileus, or other concomitants of critical illness. Inhaled therapy may be most appropriate for pulmonary vascular diseases (e.g., pulmonary hypertension).

Pharmaceutical compositions may be assembled into kits or pharmaceutical systems for use in arresting cell cycle in rapidly dividing cells, e.g., cancer cells. Kits or pharmaceutical systems according to this aspect of the invention comprise a carrier means, such as a box, carton, tube, having in close confinement therein one or more container means, such as vials, tubes, ampoules, bottles, syringes, or bags. The kits or pharmaceutical systems of the invention may also comprise associated instructions for using the kit.

By "analog" is meant a molecule that is not identical, but has analogous functional or structural features. For example, a polypeptide analog retains the biological activity of a corresponding naturally-occurring polypeptide, while having certain biochemical modifications that enhance the analog's function relative to a naturally occurring polypeptide. Such biochemical modifications could increase the analog's protease resistance, membrane permeability, or half-life, without altering, for example, ligand binding. An analog may include an unnatural amino acid.

By "binding to" a molecule is meant having a physicochemical affinity for that molecule.

"Detect" refers to identifying the presence, absence or amount of the analyte to be detected.

By "disease" is meant any condition or disorder that damages or interferes with the normal function of a cell, tissue, or organ. Examples of diseases include those associated with endothelial dysfunction.

By the terms "effective amount" and "therapeutically effective amount" of a formulation or formulation component is meant a sufficient amount of the formulation or component, alone or in a combination, to provide the desired effect. For example, by "an effective amount" is meant an amount of a compound, alone or in a combination, required to ameliorate the symptoms of a disease relative to an untreated patient. The effective amount of active compound(s) used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

By "fragment" is meant a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. For example, a fragment may contain 10, 20, 30, 40, 50, 60, 70, 80, 90, or 100, 200, 300, 400, 500, 600, 700, 800, 900, or 1000 nucleotides or amino acids. However, the invention also comprises polypeptides and nucleic acid fragments, so long as they exhibit the desired biological activity of the full length polypeptides and nucleic acid, respectively. A nucleic acid fragment of almost any length is employed. For example, illustrative polynucleotide segments with total lengths of about 10,000, about 5000, about 3000, about 2,000, about 1,000, about 500, about 200, about 100, about 50 base pairs in length (including all intermediate lengths) are included in many implementations of this invention. Similarly, a polypeptide fragment of almost any length is employed. For example, illustrative polypeptide segments with total lengths of about 10,000, about 5,000, about 3,000, about 2,000, about 1,000, about 5,000, about 1,000, about 500, about 200, about 100, or about 50 amino acids in length (including all intermediate lengths) are included in many implementations of this invention.

The terms "isolated," "purified," or "biologically pure" refer to material that is free to varying degrees from components which normally accompany it as found in its native state. "Isolate" denotes a degree of separation from original source or surroundings. "Purify" denotes a degree of separation that is higher than isolation.

A "purified" or "biologically pure" protein is sufficiently free of other materials such that any impurities do not materially affect the biological properties of the protein or cause other adverse consequences. That is, a nucleic acid or peptide of this invention is purified if it is substantially free of cellular material, viral material, or culture medium when produced by recombinant DNA techniques, or chemical precursors or other chemicals when chemically synthesized. Purity and homogeneity are typically determined using analytical chemistry techniques, for example, polyacrylamide gel electrophoresis or high performance liquid chromatography. The term "purified" can denote that a nucleic acid or protein gives rise to essentially one band in an electrophoretic gel. For a protein that can be subjected to modifications, for example, phosphorylation or glycosylation, different modifications may give rise to different isolated proteins, which can be separately purified.

Similarly, by "substantially pure" is meant a nucleotide or polypeptide that has been separated from the components that naturally accompany it. Typically, the nucleotides and polypeptides are substantially pure when they are at least 60%, 70%, 80%, 90%, 95%, or even 99%, by weight, free from the proteins and naturally-occurring organic molecules with they are naturally associated.

By "isolated nucleic acid" is meant a nucleic acid that is free of the genes which flank it in the naturally-occurring genome of the organism from which the nucleic acid is derived. The term covers, for example: (a) a DNA which is part of a naturally occurring genomic DNA molecule, but is not flanked by both of the nucleic acid sequences that flank that part of the molecule in the genome of the organism in which it naturally occurs; (b) a nucleic acid incorporated into a vector or into the genomic DNA of a prokaryote or eukaryote in a manner, such that the resulting molecule is not identical to any naturally occurring vector or genomic DNA; (c) a separate molecule such as a synthetic cDNA, a genomic fragment, a fragment produced by polymerase chain reaction (PCR), or a restriction fragment; and (d) a recombinant nucleotide sequence that is part of a hybrid gene, i.e., a gene encoding a fusion protein. Isolated nucleic acid molecules according to the present invention further include molecules produced synthetically, as well as any nucleic acids that have been altered chemically and/or that have modified backbones. For example, the isolated nucleic acid is a purified cDNA or RNA polynucleotide. Isolated nucleic acid molecules also include messenger ribonucleic acid (mRNA) molecules.

By an "isolated polypeptide" is meant a polypeptide of the invention that has been separated from components that naturally accompany it. Typically, the polypeptide is isolated when it is at least 60%, by weight, free from the proteins and naturally-occurring organic molecules with which it is naturally associated. Preferably, the preparation is at least 75%, more preferably at least 90%, and most preferably at least 99%, by weight, a polypeptide of the invention. An isolated polypeptide of the invention may be obtained, for example, by extraction from a natural source, by expression of a recombinant nucleic acid encoding such a polypeptide; or by chemically synthesizing the protein. Purity can be measured by any appropriate method, for example, column chromatography, polyacrylamide gel electrophoresis, or by HPLC analysis.

By "reduces" is meant a negative alteration of at least 5%, 10%, 25%, 50%, 75%, or 100%.

By "specifically binds" is meant a compound or antibody that recognizes and binds a polypeptide of the invention, but which does not substantially recognize and bind other molecules in a sample, for example, a biological sample, which naturally includes a polypeptide of the invention.

Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. By "hybridize" is meant pair to form a double-stranded molecule between complementary polynucleotide sequences (e.g., a gene described herein), or portions thereof, under various conditions of stringency. (See, e.g., Wahl, G. M. and S. L. Berger (1987) Methods Enzymol. 152:399; Kimmel, A. R. (1987) Methods Enzymol. 152:507).

For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred: embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 .mu.g/ml denatured salmon sperm DNA (ssDNA). In a most preferred embodiment, hybridization will occur at 42° C. in 250 mM NaCl, 25 mM trisodium citrate, 1% SDS, 50% formamide, and 200 µg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42 C in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196: 180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and more preferably 90%, 95% or even 99% identical at the amino acid level or nucleic acid to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

The terms "treating" and "treatment" as used herein refer to the administration of an agent or formulation to a clinically symptomatic individual afflicted with an adverse condition, disorder, or disease, so as to effect a reduction in severity and/or frequency of symptoms, eliminate the symptoms and/or their underlying cause, and/or facilitate improvement or remediation of damage. It will be appreciated that, although not precluded, treating a disorder or condition does not require that the disorder, condition or symptoms associated therewith be completely eliminated.

The terms "preventing" and "prevention" refer to the administration of an agent or composition to a clinically asymptomatic individual who is susceptible or predisposed to a particular adverse condition, disorder, or disease, and thus relates to the prevention of the occurrence of symptoms and/or their underlying cause.

Unless specifically stated or obvious from context, as used herein, the term "or" is understood to be inclusive. Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

Any compositions or methods provided herein can be combined with one or more of any of the other compositions and methods provided herein.

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

Other features and advantages of the invention will be apparent from the following description of the preferred embodiments thereof, and from the claims. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All published foreign patents and patent applications cited herein are incorporated herein by reference. Genbank and NCBI submissions indicated by accession number cited herein are incorporated herein by reference. All other published references, documents, manuscripts and scientific literature cited herein are incorporated herein by reference. In the case of conflict, the present specification, including definitions, will control. In addition, the materials, methods, and examples are illustrative only and not intended to be limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 3J shows quantification of the ratio of GFP (X-axis: $\log_2$ scale) and mKO (Y-axis: $\log_2$ scale) fluorescence intensity in GSC-GB pairs: nos>H3 (opened circle, N=55) and nos>H3T3A (solid triangle, N=38), based on Table 1. Red dotted outline delineates symmetric distribution [the 1.5-fold cutoff line is based on the quantification range of symmetric H3 distribution in spermatogonial cells and H3.3 distribution in GSC-GB pairs (Tran et al., 2012, Science 338: 679; Tran et al., 2013 Chromosome Res, 21: 255). H3 (N=55): GSC/GB GFP ratio=10.11±1.66 ($P<10^{-4}$ for the ratio>1), GB/GSC mKO ratio=1.61±0.19 (P=0.001 for the ratio>1). H3T3A (N=38): GSC/GB GFP ratio=1.11±0.23 (P=0.65 therefore is insignificantly different from 1), GB/GSC mKO ratio=1.31±0.10 (P=0.001 for the ratio>1). Noticeably, the mKO ratio in GB/GSC in nos>H3T3A testes is significantly greater than 1:1 ratio. Previous data showed that a post-mitotic histone turn-over mechanism acts in the GB (Tran et al., 2012 Science 338, 679), which may be responsible for this significant enrichment of mKO signal in GB cells. All ratios=Avg±SE; P-value: one-sample t test.

FIG. 5A is a cartoon showing the asymmetric H3 inheritance during male GSC asymmetric cell division. FIG. 5B is a schematic diagram of a two-step model to explain how asymmetric epigenome is established during S phase (Step one) and recognized followed by asymmetric segregation in M phase (Step two) GSC, adapted from (Tran et al., 2013 Chromosome Res 21, 255).

FIG. 7A-FIG. 7X is a series of photomicrographs showing spatial and temporal specificity of the H3T3P signal. FIG. 7A-FIG. 7L show co-immunostaining using antibodies against H3T3P and a centromere-specific marker CID in germ cells from y,w control (FIG. 7A-FIG. 7D) and nos>H3-GFP (E-L) males. FIG. 7M-FIG. 7X show co-immunostaining using antibodies against H3T3P and H3S10P in a prophase GB (FIG. 7M-FIG. 7P), a metaphase GSC (FIG. 7Q-FIG. 7T), and an anaphase GSC (FIG. 7U-FIG. 7X) from nos>H3-GFP males. Asterisk: hub. Scale bars: 5 μm.

FIG. 8A-FIG. 8D show immunostaining using anti-Vasa in a nos>upd; H3T3A-GFP testis (outlined). Overexpression of the JAK-STAT pathway ligand Upd leads to overpopulation of early stage germ cells (Kiger et al., 2001 Science 294, 2542; Tulina et al., 2001 Science 294, 2546) labeled with GFP (FIG. 8B) and Vasa (FIG. 8C). Scale bar: 100 μm. FIG. 8E is a series of immunoblots using antibodies against GFP, H3, and H4, respectively, as well as Ponceau S staining to show load of total crude extract in each lane of SDS gel. All blots are duplicates using the same samples with the same amount, nos>upd testes were used as a negative control for the H3-GFP and H3T3A-GFP transgenes.

FIG. 9A is a schematic diagram showing the dual color-switch design that expresses preexisting H3T3A (or D)-GFP and newly synthesized H3T3A (or D)-mKO by heat shock treatment, as adapted from (Tran et al., 2012, Science 338: 679). FIG. 9B is a schematic showing Drosophila male has two sex chromosomes: X and Y chromosomes; as well as three autosomes: the second (II), the third (III), and the fourth chromosomes. But because the fourth chromosomes are very small, the prediction is focused on X, Y, II and III chromosomes. With each sex chromosome having two and each autosome having four potential segregation patterns, the total would be 64 different combinations. Among all 64, only four when the two autosomes "agree" to partition the H3-GFP-enriched chromatids to GSC show wild-type H3 asymmetric pattern (pattern 1-4); whereas the other four when the two autosomes "agree" to partition the H3-mKO-enriched chromatids to GSC show the opposite asymmetric pattern (pattern 5-8).

FIG. 10A-FIG. 10P is a series of photomicrographs showing the effects of temperature shift on the dominant negative activity of the H3T3A transgene. FIG. 10A-FIG. 10H show immunostaining using anti-H3T3P and anti-H3S10P in testes from hs-FLP; nos-Gal4; UAS-FRT-H3-GFP-PolyA-FRT-H3-mKO males. Flies were raised at 18° C. without heat shock (FIG. 10A-FIG. 10D) and heat shocked at 37° C. for two hours followed by 48 hour recovery at 29° C. (FIG. 10E-FIG. 10H). Before heat shock treatment, H3-GFP was expressed at a low, but detectable level (FIG. 10A) because nos-Gal4 has relatively low activity at 18° C. (Tran et al., 2012, Science 338: 679; Eliazer et al., 2011 Proc Natl Acad Sci USA, 108, 7064), while no H3-mKO signal was detectable (FIG. 10B). After heat shock and recovery, H3-GFP was negligible (FIG. 10E), but H3-mKO was robustly turned on (FIG. 10F). No effect on either H3T3P (FIG. 10C, FIG. 10G) or H3S10P (FIG. 10D, FIG. 10H) signals could be detected. FIG. 10I-FIG. 10P show immunostaining using anti-H3T3P and anti-H3S10P in testes from hs-FLP; nos-Gal4; UAS-FRT-H3T3A-GFP-PolyA-FRT-H3T3A-mKO males. Flies were raised at 18° C. without heat shock (FIG. 10I-FIG. 10L, inset in FIG. 10I and FIG. 10J are shown with higher magnification in FIG. 10K and FIG. 10L) and heat shocked at 37° C. for two hours followed by 48-hour recovery at 29° C. (FIG. 10M-FIG. 10P, inset in FIG. 10M and FIG. 10N are shown with higher magnification in FIG. 10O and FIG. 10P). Before heat shock treatment, H3T3A-GFP was expressed at a low, but detectable level (FIG. 10I), while no H3T3A-mKO signal was detectable (FIG. 10J). After heat shock and recovery, H3T3A-GFP was negligible (FIG. 10M), but H3T3A-mKO was robustly turned on (FIG. 10N). The H3T3P signal was reduced in males that are heat shocked and recovered (FIG. 10O) compared to those raised at 18° C. constantly (FIG. 10K), most likely due to higher H3T3A expression by the nos-Gal4 driver at 29° C. (Eun et al., 2014 Science, 343, 1513). By contrast, the temperature change had little effect on the H3S10P (FIG. 10L, FIG. 10P) signals. Scale bars: 10 μm.

FIG. 11A-FIG. 11O shows immunostaining using anti-FasIII, α-Spectrin and Vasa antibodies in testes from 15-day old nos>H3-GFP males (FIG. 11A-FIG. 11E), 1-day (FIG. 11F-FIG. 11J) and 15-day (FIG. 11K-FIG. 11O) nos>H3T3A-GFP males. Early germ cells judged by nuclear morphology (Tran et al., 2000 Nature 407, 754; Chen et al., 2013 Cell Stem Cell 13, 73) are delineated by the yellow dotted lines in (FIG. 11E, FIG. 11J), but is throughout the sample in (FIG. 11O).

FIG. 12A-FIG. 12H show immunostaining using anti-FasIII and α-Spectrin antibodies in testes from nos>H3T3A-GFP males. A testicular tumor developed (insets in FIG. 12A and FIG. 12B are shown at higher magnification in FIG. 12C and FIG. 12D) with over-proliferated very early stage germ cells with GFP expression (FIG. 12C) and spectrosome structure (FIG. 12D, arrowhead). A testicular tumor developed (insets in FIG. 12E and FIG. 12F are shown at higher magnification in FIG. 12G and FIG. 12H) with over-proliferated spermatogonial cells without GFP expression (FIG. 12G) and fusome structure (FIG. 12H, arrow). Asterisk: hub. Scale bars: 20 μm.

FIG. 13A is a Spearman correlation coefficient matrix between pairs of transcription level profiles of wild-type, nos>upd, nos>H3T3A and barn mutant testes plotted in a heatmap. The color bar indicates the high (red) to low (blue) correlation. The distance is defined as 1-Spearman correlation coefficient (see Materials and Methods). FIG. 13B is a dimension reduction representation of the pairwise distance matrix of wild-type (blue dot), nos>upd (green dots), nos>H3T3A (red dots) and barn mutant (yellow dot) testis samples. FIG. 13C is a Venn diagram of actively expressed genes in four genotypes. Individual samples were combined for each genotype.

FIG. 13D is a heatmap of the representative wild-type-specific genes. FIG. 13E is a heatmap of the representative nos>H3T3A-specific genes. Genes involved in DNA repair pathway (q value=1.4×10$^{-4}$) and RNA PolII-dependent transcription initiation (q value=0.167) are enriched in nos>H3T3A testis samples. Z score shown in heatmap index.

FIG. 14V shows the quantification of the percentage of testes with germline tumor and Vasa$^+$ germ cell loss in testes expressing nos>H3-GFP (n=19), nos>H3T3A-GFP (n=42), and nos>H3T3D-GFP (n=43).

FIG. 15A-FIG. 15Q is a schematic and a series of photomicrographs showing that the expression of H3T3A or H3T3D using the bam-Gal4 driver did not lead to phenotypes like those driven by the nos-Gal4 driver. FIG. 15A is a cartoon showing stage-specificity of nos-Gal4 and bam-Gal4 drivers: nos-Gal4 is turned on in early-stage germline, including GSCs, while bam-Gal4 expresses from 4-cell spermatogonial cells. FIG. 15B-FIG. 15I show expression of the H3T3A transgene using a later stage germline driver bam-Gal4 greatly reduces H3T3P in later stage mitotic spermatogonial cells, by anti-FasIII, H3T3P, H3S10P and Vasa immunostaining in testes from bam>H3T3A-GFP males. A two-cell stage mitotic spermatogonia cyst without H3T3A-GFP expression (FIG. 15B) had detectable H3T3P (FIG. 15C) and H3S10P (FIG. 15D), both H3T3P and H3S10P overlapped with DNA signal stained with Hoechst (FIG. 15E). By contrast, a four-cell stage mitotic spermatogonia with H3T3A-GFP expression (FIG. 15F) had undetectable H3T3P (FIG. 15G), but abundant H3S10P (FIG. 15H), the H3S10P signal overlapped with DNA signal stained with Hoechst (FIG. 15I). The diffusive signal in (FIG. 15C) and (FIG. 15G) came from anti-Vasa, which stained the entire cell undergoing mitosis (Yadlapalli et al., 2011 J Cell Sci 124, 933; Yuan et al., 2012 Dev Biol 361, 57). Scale bars: 10 μm. FIG. 15J-FIG. 15Q show immunostaining using anti-FasIII and α-Spectrin: tip of the testis expressing either bam>H3T3A-GFP (FIG. 15J-FIG. 15M) or bam>H3T3D-GFP (FIG. 15N-FIG. 15Q). Scale bars: 20 μm. Asterisk: hub.

FIG. 16A-FIG. 16H show immunostaining using anti-FasIII, α-Spectrin and Vasa antibodies in testes expressing the dual-color H3T3D (FIG. 9A-FIG. 9B): representative GSC-GB pair expressing H3T3D-GFP and H3T3D-mKO in a symmetric manner (FIG. 16B-FIG. 16C) or opposite asymmetric manner (FIG. 16F-FIG. 16G). Asterisk: hub. Scale bars: 5 μm. FIG. 16I shows quantification of the ratio of GFP (X-axis: log$_2$ scale) and mKO (Y-axis: log$_2$ scale) fluorescence intensity in GSC-GB pairs expressing H3T3D (opened square, N=31), most of which are in zone III and IV, based on Table 1. H3T3D (N=31): GSC/GB GFP ratio=0.83±0.05 (P=0.001 for the ratio<1), GB/GSC mKO ratio=1.08±0.04 (P=0.03 for the ratio>1). Noticeably, the mKO ratio in GB/GSC in H3T3D-expressing testes is significantly greater than 1:1 ratio. Previous data showed that a post-mitotic histone turn-over mechanism acts in the GB cell (Tran et al., 2012 Science 338, 679), which may be responsible for this significant enrichment of mKO signal in the GB cell in H3T3D-expressing testes. All ratios=Avg±SE; P-value: one-sample t test.

FIG. 17A-FIG. 17D show immunostaining using anti-Fas III, H3T3P, H3S10P and Vasa antibodies in testes from nos>haspin shRNA males. A mitotic GSC (arrow, FIG. 17B-FIG. 17D) had diffusive Vasa (FIG. 17B) (Yadlapalli et al., 2011 J Cell Sci 124, 933; Yuan et al., 2012 Dev Biol 361, 57), overlapping H3S10P (FIG. 17C) and Hoechst (FIG. 17D) staining signals, but undetectable H3T3P (FIG. 17B). A mitotic CySC (arrowhead, FIG. 17B-FIG. 17D) with normal Haspin level has detectable H3T3P (FIG. 17B) and H3S10P (FIG. 17C), both signals overlap with Hoechst (FIG. 17D) staining signal. FIG. 17E-FIG. 17L show lysotrack staining and immunostaining using anti-Vasa in testes from nos-Gal4 control males (FIG. 17E-FIG. 17H) and nos>haspin shRNA males (FIG. 17I-FIG. 17L). More germ cells are positive with lysotrack staining (yellow arrow) in testes from nos>haspin shRNA males (FIG. 17J-FIG. 17K) compared to the nos-Gal4 control males (FIG. 17F-FIG. 17G). Asterisk: hub. Scale bars: 10 μm. FIG. 17M shows the quantification of lysotrack-positive germline cysts in nos-Gal4 control testes (n=20) and nos>haspin shRNA testes (n=20). **: P<0.001. P-value calculated by unpaired t test.

FIG. 18A-FIG. 18W is a series of photomicrographs, bar charts, and a dot plot showing that mutations in the haspin gene enhance nos>H3T3A, but suppress nos>H3T3D germline phenotype. FIG. 18A-FIG. 18L show immunostaining using anti-FasIII, α-Spectrin and Vasa antibodies in testes from nos>H3T3A (FIG. 18A-FIG. 18D), Df (haspin)/+; nos>H3T3A (FIG. 18E-FIG. 18H) or haspin$^{mi09386/+}$; nos>H3T3A (FIG. 18I-FIG. 18L) males at constant 18° C. Larval testes were used for analysis because at this developmental stage and at 18° C., H3T3P is retained (FIG. 10K) and cellular defects in nos>H3T3A were minimal (FIG. 11F-FIG. 11J). Therefore, it was used as a permissive condition to test genetic enhancement. The germline tumor is detected in testes from Df (haspin)/+; nos>H3T3A (FIG. 18H) or haspin$^{mi09386/+}$; nos>H3T3A (FIG. 18L) males, but not in testes from nos>H3T3A (FIG. 18D) by itself. FIG. 18M shows the percentage of testes that are normal or have germline tumor(s) from males of the following genotypes: nos>H3T3A (n=18); Df (haspin)/+; nos>H3T3A (n=16); and haspin$^{mi09386/+}$; nos>H3T3A (n=19). FIG. 18N-FIG. 18U show immunostaining using anti-FasIII, α-Spectrin and Vasa antibodies in testes from nos>H3T3D (FIG. 18N-FIG. 18Q) or Df (haspin)/+; nos>H3T3D (FIG. 18R-FIG. 18U) males (siblings from the same crosses) grown at 18° C., shifted to 29° C. as newly enclosed flies and kept at 29° C. for seven days. Germline tumors were detected in testes from nos>H3T3D males (FIG. 18O, FIG. 18Q), but not in testes from Df (haspin)/+; nos>H3T3D males (FIG. 18S, FIG. 18U). Early germ cells, as determined by nuclear morphology (Tran et al., 2000 Nature 407, 754; Chen et al., 2013 Cell Stem Cell 13, 73), are delineated by the yellow dotted lines in (FIG. 18D, FIG. 18H, FIG. 18L, FIG. 18Q, FIG. 18U). FIG. 18V shows the percentage of testes that have germline tumor(s) or germ cell loss from males with the following genotypes: nos>H3T3D (n=17) and Df (haspin)/+; nos>H3T3D (n=12). FIG. 18W shows the quantification of hub size: 172.2±14.72 μm$^2$ in nos>H3T3D (n=17) testes vs. 115.0±9.802 μm$^2$ in Df (haspin)/+; nos>H3T3D (n=12) testes (*P<0.005, calculated by unpaired t test). Scale bars: 20 μm.

FIG. 21A shows a schematic diagram showing the dual color-switch design that expresses pre-existing H3T3A-GFP and newly synthesized H3T3A-mKO by heat-shock treatment, as adapted from Tran et al. (2012).

FIG. 22J shows quantification of the ratio of GFP (y axis: log 2 scale) fluorescence intensity in GSC-GB pairs (see FIGS. 3J, 16, and Table 1 for details): nos>H3 (open circle, n=55), nos>H3T3A (solid triangle, n=64), and nos>H3T3D (open square, n=57). Red dotted outline delineates symmetric distribution zone (see explanations below). H3 (n=55): GSC/GB GFP ratio=10.11±1.66 (p<10 4 for the ratio>1, one-tailed t test). H3T3A (n=64): GSC/GB GFP ratio=1.50±0.28 (p>0.05 therefore is insignificantly different from 1, two-tailed t test). H3T3D (n=57): GSC/GB GFP ratio=1.56±0.51 (p>0.05 therefore is insignificantly different from 1, two-tailed t test). All ratios=Avg±SE; p value, one sample t test. FIG. 22K shows percentage of GSC-GB pairs with conventional asymmetric (GFP in GSC/GB>1.55), symmetric (GSC/GB GFP ratio between 1-1.45 and GB/GSC GFP ratio between 1-1.45), inverted asymmetric (GFP in GB/GSC>1.55), and borderline (GSC/GB GFP ratio between 1.45-1.55 and GB/GSC GFP ratio between 1.45-1.55) patterns, respectively in nos>H3, nos>H3T3A, and nos>H3T3D testes, as well as the predicted patterns according to randomized segregation modeling (Table 2A, Table 2B, and FIG. 27). In nos>H3 testes, conventional asymmetric: 87.3% (48/55); symmetric: 12.7% (7/55); no inverted asymmetric or borderline pairs. In nos>H3T3A testes, conventional asymmetric: 9.4% (6/64); symmetric: 71.9% (46/64); inverted asymmetric: 12.5% (8/64); borderline: 6.3% (4/64). In nos>H3T3D testes, conventional asymmetric: 7.0% (4/57); symmetric: 79.0% (45/57); inverted asymmetric: 10.5% (6/57); borderline: 3.5% (2/57). Predicted patterns: conventional asymmetric: 18.7% (12/64); symmetric: 53.1% (34/64); inverted asymmetric: 18.7% (12/64); borderline: 9.4% (6/64). See also FIGS. 3J, 16, and Table 1.

FIG. 23A shows a prophase GSC expressing nos>FRT-H3.3-GFP-PolyA-FRT-H3.3-mKO-PolyA transgene during the second mitosis after heat-shock-induced genetic switch from H3.3-GFP-encoding to H3.3-mKO-encoding sequences. FIG. 23B and FIG. 23C show prophase GSC (FIG. 23B) and GB (FIG. 23C) expressing nos>FRT-H3T3A-GFP-PolyA-FRT-H3T3A-mKO-PolyA transgene during the second mitosis after heat-shock-induced genetic switch from H3T3A-GFP-encoding to H3T3A-mKO-encoding sequences.

FIG. 25A and FIG. 25B show immunostaining using antibodies against a hub marker FasIII and a spectrosome/fusome marker α-Spectrin in nos>H3-GFP (FIG. 25A) or nos>H3T3A-GFP (FIG. 25B) testes, inserts in the merged panel are shown at higher magnification in single-channel panels, respectively. Arrows in (FIG. 25A) point to dotted spectrosome, arrowheads in (FIG. 25B) point to branched fusomes. FIG. 25C shows quantification of the GSC number in nos>H3-GFP or nos>H3T3A-GFP testes. GSCs with branched fusome (black): 0.65±0.95 in nos>H3-GFP testes (n=30) versus 2.68±1.27 in nos>H3T3A-GFP testes (n=30); GSCs with dotted spectrosome: 9.45±1.65 in nos>H3-GFP testes versus 6.97±1.76 in nos>H3T3A-GFP testes (All ratios=Avg±SE; ***p<0.001). FIG. 25D-FIG. 25F shows immunostaining using antibodies against a hub marker FasIII and a spectrosome/fusome marker α-Spectrin in testes from nos>H3-GFP (FIG. 25D), nos>H3T3A-GFP (FIG. 25E), or nos>H3T3D-GFP (FIG. 25F) males. Early-stage germ cells expressing GFP expand, hub size increases (FIG.

25E) and (FIG. 25F), in comparison with (FIG. 25D), insets in the merged panel (the first column) are shown at higher magnification in single-channel panels, respectively). Scale bars: 20 uM.

Figure 26:
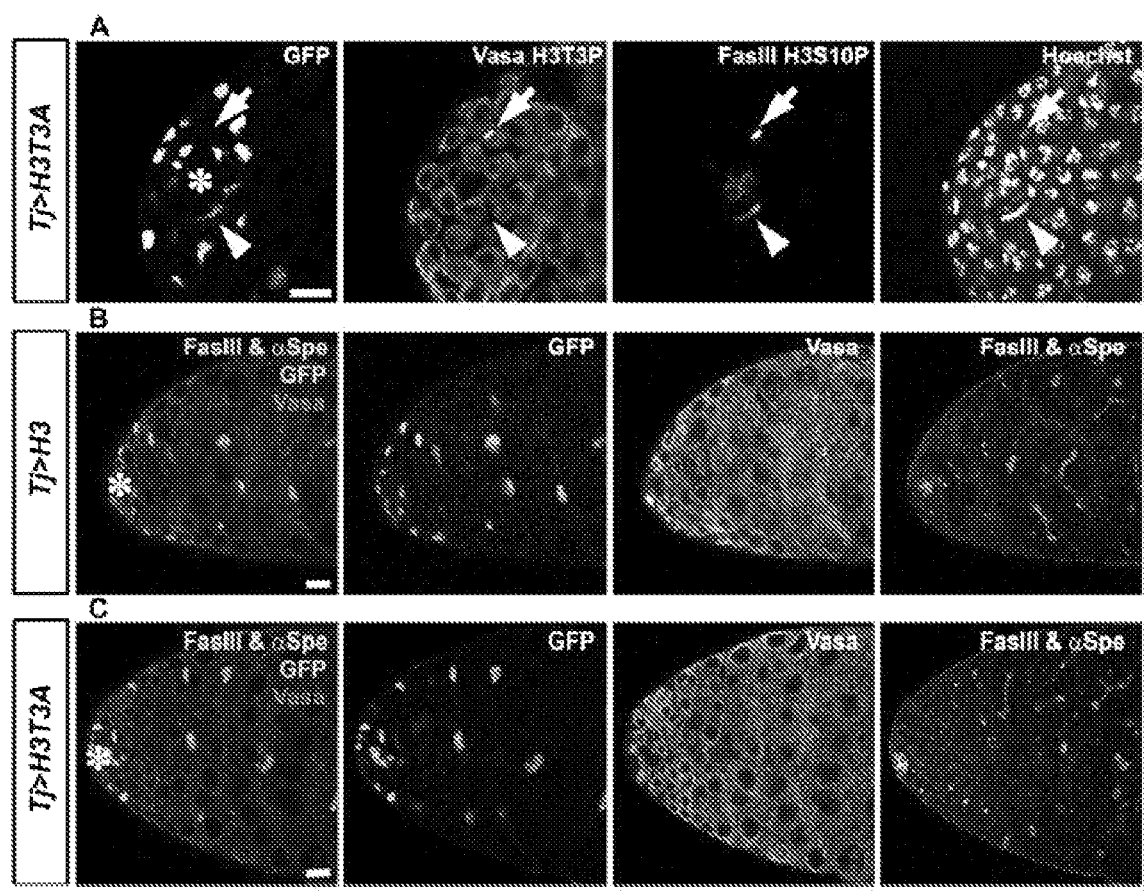

FIG. 26A-FIG. 26C shows a series of photographs demonstrating that expression of H3T3A in somatic gonadal cells does not lead to obvious cellular defects. FIG. 26A shows immunostaining using antibodies against a hub marker FasIII, a germ cell-specific marker Vasa, H3T3P, and H3S10P in Tj>H3T3A-GFP testes. A metaphase GB cell with Vasa staining but without H3T3A-GFP expression (arrow in FIG. 26A) is positive with both H3T3P and H3S10P (arrow) signals. By contrast, a metaphase cyst stem cell (CySC) without Vasa staining but with H3T3A-GFP expression is negative with H3T3P signal) but positive with H3S10P signal (arrowhead). FIG. 26B and FIG. 26C show immunostaining using antibodies against FasIII, α-Spectrin, and Vasa in Tj>H3-GFP (FIG. 26B) or Tj>H3T3A-GFP (FIG. 26C) testes. Scale bars: 20 μm.

Figure 27:
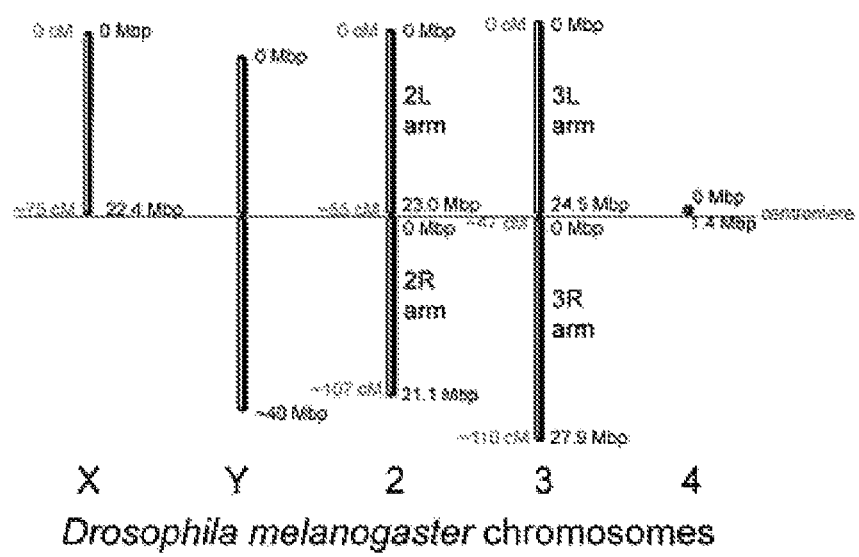

FIG. 27 is a diagram depicting *Drosphila melanogaster* chromosomes X, Y, 2, 3, and 4. Mbps values correspond with similar values in Table 2A and Table 2B.

Figure 3:
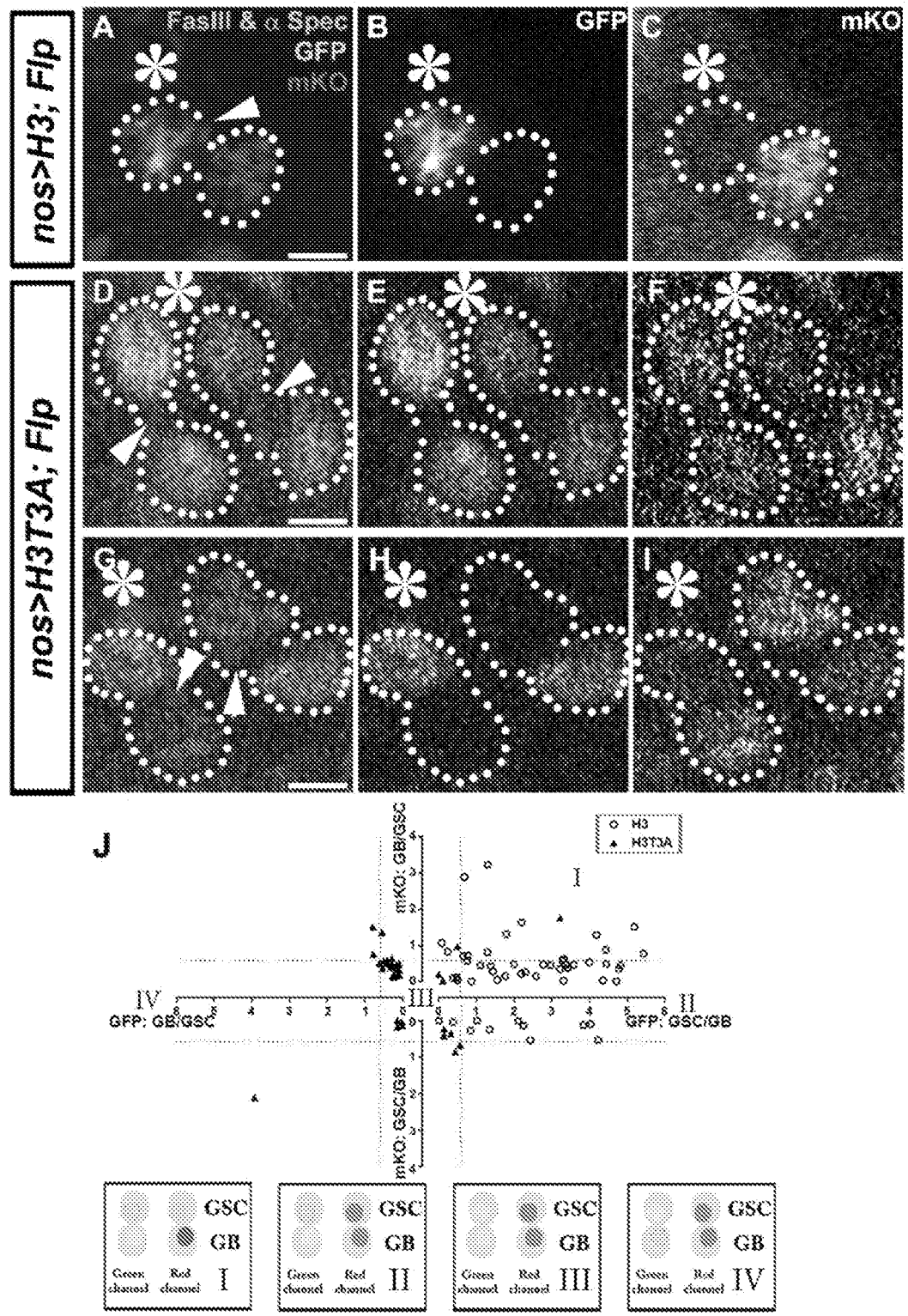
FIG. 3A-FIG. 3J is a series of photomicrographs showing that expression of H3T3A randomizes H3 inheritance pattern. Specifically, the panels show immunostaining signals using anti-FasIII and anti-α-Spectrin at the tip of nos>H3 (FIG. 3A-FIG. 3C) or nos>H3T3A (FIG. 3D-FIG. 3I) testes. Scale bars: 5 µm.
Figure 16:
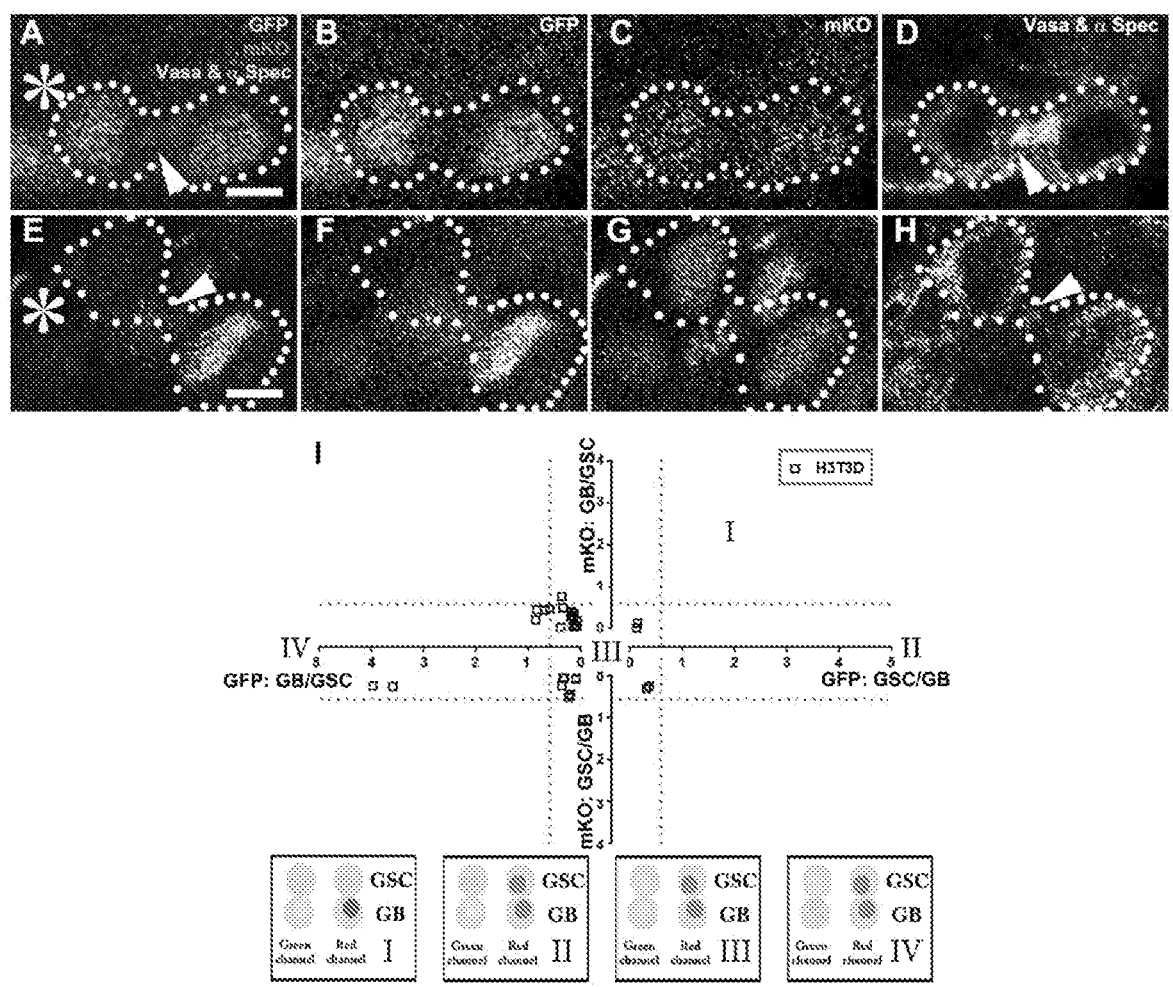
FIG. 16A-FIG. 16I is a series of photomicrographs and a dot plot showing that the expression of H3T3D randomizes preexisting vs. newly synthesized H3 inheritance during GSC asymmetric division.

FIG. 28 is a table showing the quantification of preexisting vs. newly synthesized H3, H3T3A and H3T3D in GSC-GB pairs for FIG. 3K and FIG. 16I.

FIG. 29A is a table showing the results for a 100% Asymmetric Deposition.

Figure 29B:
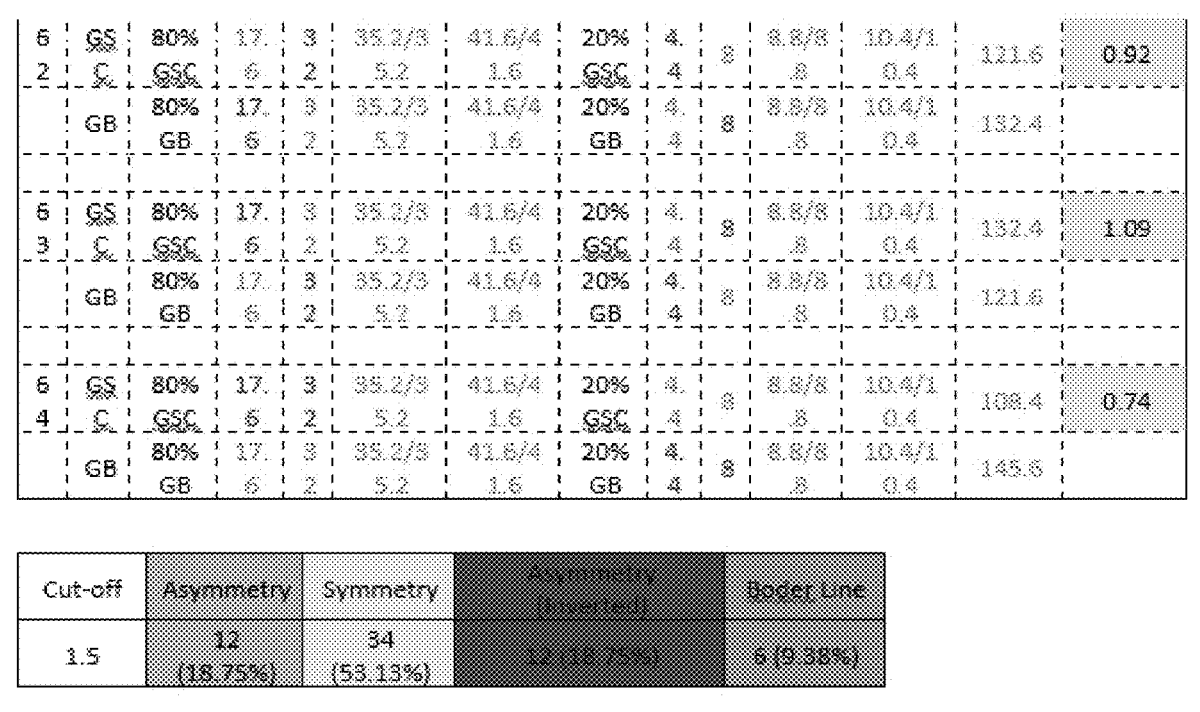

FIG. 29B is a table showing the results for a 80% Asymmetric Deposition.

DETAILED DESCRIPTION

The invention is based, at least in part, on the surprising discovery that histone H3 Thr 3 phosphorylation regulates asymmetric H3 inheritance and male germline activity in *Drosophila* and that an H3T3A mutant protein efficiently reduces H3T3P and causes increased cell death of rapidly-dividing cells. The methods described herein introduce a point mutation of the Thr3 residue of the transgenic histone H3 protein to produce a mutant transgenic protein to reduce the post-translational modification of H3 (i.e., to reduce the H3T3 phosphorylation in rapidly dividing cells) to cause cell cycle arrest followed by cell death. Because the mutant transgenic protein effectively reduces Thr3 phosphorylation including endogenous H3, this mutant form acts dominant negatively. Specifically, as described in detail below, a transgene that carries a mutation that converts threonine 3 (Thr3 or T3) to the unphosphorylatable alanine (Ala or A) greatly reduces the phosphorylation at T3 of histone 3 (H3T3P) mark. As described herein, during male germline stem cell asymmetric division, H3T3P regulates asymmetric H3 inheritance and affects germ cell function.

Cancer is one of the most prevalent diseases, accounting for 25% of all deaths in the United States (Siege et al., 2012 Cancer statistics, 2:10-29). Prior to the invention described herein, there was a pressing need to develop new strategies to inhibit rapidly dividing cancer cells. As described herein, the H3T3P mark is important for mitosis and the reduction of which leads to increased cell death in rapidly-dividing cells including cancer cells. As such, the methods described herein antagonize growth in rapidly dividing cells. For example, the compositions described herein are anti-cancer agents that are utilized in methods to reduce tumor cell growth.

As described in detail below, histone H3 shows asymmetric distribution during *Drosophila* male germline stem cell (GSC) asymmetric division. Prior to the invention described herein, the molecular mechanism and the biological relevance underlying this phenomenon were unclear. Described herein are experiments that demonstrate that phosphorylation at threonine 3 of H3 (H3T3P) distinguishes preexisting versus newly synthesized H3 in mitotic GSCs. A mutation that converts T3 to the unphosphorylatable alanine reduces H3T3P and results in randomized H3 inheritance patterns. Reduction of H3T3P causes GSC maintenance and germline differentiation defects including germ cell loss and tumors. Expression of H3 with T3 changed to phosphor-mimic aspartic acid results in similar phenotypes, indicating tight temporal control of H3T3P. The results presented herein indicate that mitosis-specific H3T3P distinguishes sister chromatids enriched with distinct H3 proteins and coordinates their proper inheritance, which is important for proper activity of both daughter cells derived from GSC asymmetric division.

Many types of adult stem cells undergo asymmetric cell division to generate a self-renewed stem cell and a daughter cell which will subsequently differentiate (Morrison et al., 2006 Nature 441, 1068; Betschinger et al., 2004 Curr Biol 14, R674; H. Clevers, 2005 Nat Genet 37, 1027; M. Inaba and Y. M. Yamashita, 2012 Cell Stem Cell 11, 461). During the asymmetric division of *Drosophila* male germline stem cell (GSC), the preexisting histone H3 is selectively segregated to the GSC, whereas the newly synthesized H3 is enriched in the differentiating daughter cell known as a gonialblast (GB) (FIG. 5A; Tran et al., 2012 Science 338, 679). Described herein is a two-step model to explain this asymmetric H3 inheritance. First, prior to mitosis, preexisting and newly synthesized H3 are differentially distributed at the two sets of sister chromatids. Second, during mitosis, the set of sister chromatids containing preexisting H3 is segregated to GSCs, while the set of sister chromatids enriched with newly synthesized H3 is segregated to the GB that differentiates (FIG. 5B; Tran et al., 2012 Science 338, 679; Tran et al., Chromosome Res 21, 255).

Figure 5:
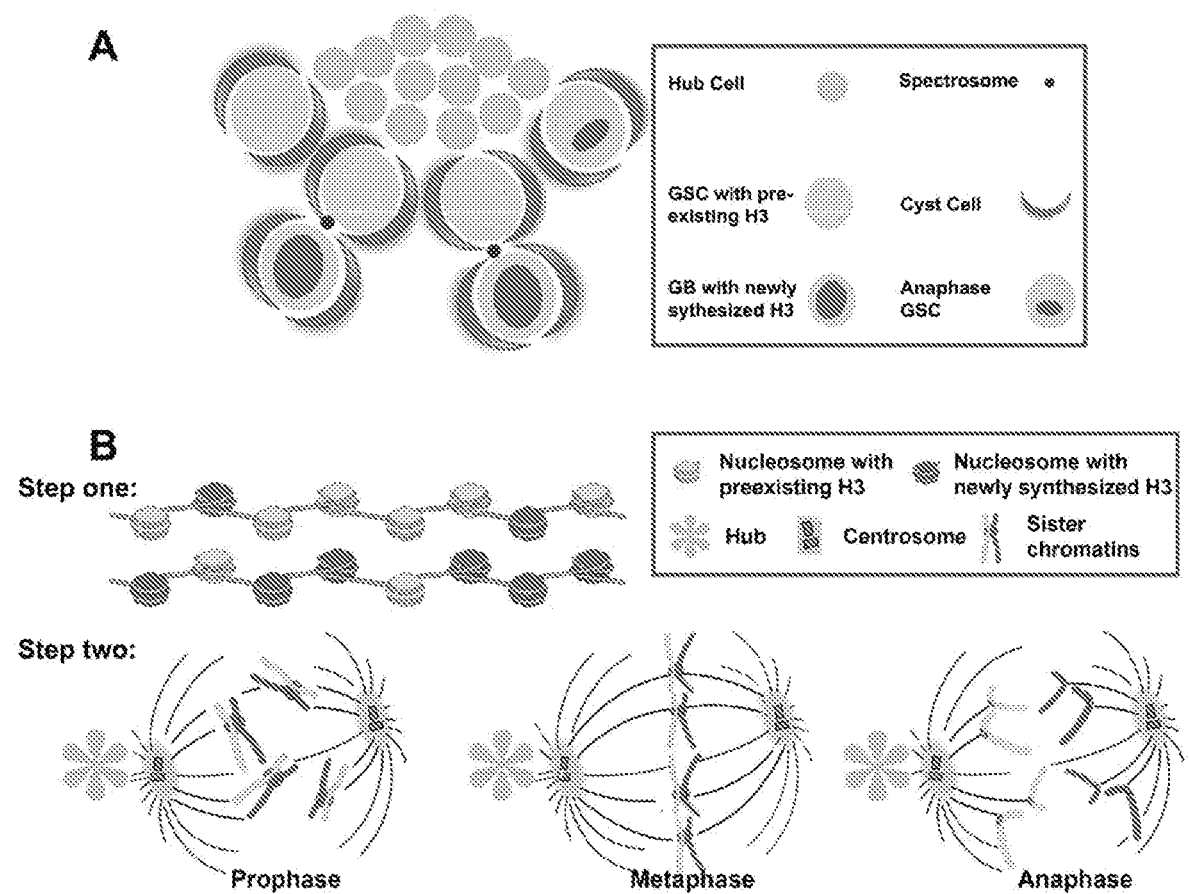
FIG. 5A-FIG. 5B is a cartoon showing Drosophila testis tip and a model for asymmetric H3 inheritance during GSC asymmetric division. Specifically.

During the asymmetric division of the *Drosophila* male germline stem cell (GSC), the pre-existing his-tone 3 (H3) is selectively segregated to the self-renewed GSC daughter cell whereas newly synthesized H3 is enriched in the differentiating daughter cell known as a gonialblast (GB) (Tran et al., 2012) (FIG. 5A). In contrast, the histone variant H3.3, which is incorporated in a replication-independent manner, does not exhibit such an asymmetric pattern. Furthermore, asymmetric H3 inheritance occurs specifically in asymmetrically dividing GSCs, but not in the symmetrically dividing progenitor cells. These findings demonstrate that global asymmetric H3 histone inheritance possesses both molecular and cellular specificity. The following model was proposed to explain these findings.

First, the cellular specificity exhibited by the H3 histone suggests that global asymmetric histone inheritance occurs uniquely in a cell-type (GSC) where the mother cell must divide to produce two daughter cells each with a unique cell fate. Because this asymmetry is not observed in symmetrically dividing GB cells, asymmetric histone inheritance was proposed to be a phenomenon specifically employed by GSCs to establish unique epigenetic identities in each of the two daughter cells. Second, a major difference between H3 and H3.3 is that H3 is incorporated to chromatin during DNA replication, while H3.3 variant is incorporated in a replication-independent manner. Because this asymmetric inheritance mode is specific to H3, a two-step model was proposed to explain asymmetric H3 inheritance: (1) prior to mitosis, pre-existing and newly synthesized H3 are differentially distributed on the two sets of sister chromatids, and (2) during mitosis, the set of sister chromatids containing pre-existing H3 is segregated to GSCs, while the set of sister chromatids enriched with newly synthesized H3 is segregated to the GB that differentiates (Tran et al., 2012, 2013) (FIG. 5B).

As described herein, a mitosis-enriched H3T3P mark acts as a transient landmark that distinguishes sister chromatids with identical genetic code but different epigenetic information, shown as pre-existing H3-GFP and newly synthesized H3-mKO. By distinguishing sister chromatids containing different epigenetic information, H3T3P functions to allow these molecularly distinct sisters to be segregated and inherited differentially to the two daughter cells derived from one asymmetric cell division. The selective segregation of different populations of histones likely allows these two cells to assume distinct fates: self-renewal versus differentiation. Consequently, loss of proper epigenetic inheritance might lead to defects in both GSC maintenance and GB differentiation, suggesting that both cells need this active partitioning process to either LLremember" or LLreset" their molecular properties.

As described in detail below, the temporal and spatial specificities of H3T3P make it a great candidate to regulate asymmetric sister chromatid segregation. First, H3T3P is only detectable from prophase to metaphase, the window of time during which the mitotic spindle actively tries to attach to chromatids through microtubule-kinetochore interactions. Second, the H3T3P signal is enriched at the peri-centromeric region, where kinetochore components robustly crosstalk with chromatin-associate factors. Third, H3T3 shows a sequential order of phosphorylation, first appearing primarily on sister chromatids enriched with pre-existing H3 and then subsequently appearing on sister chromatids enriched with newly synthesized H3 as the GSC nears metaphase. The distinct temporal patterns shown by H3T3P are unique to GSCs and would allow the mitotic machinery to differentially recognize sister chromatids bearing distinct epigenetic information; an essential step necessary for proper segregation during asymmetric GSC division. Furthermore, the tight temporal control of H3T3 phosphorylation suggests that rather than serving as an inherited epigenetic signature, H3T3P may act as transient signaling mark to allow for the proper partitioning of H3. H3T3P needs to be under tight temporal control in order to ensure proper H3 inheritance and germline activity.

As described herein, these studies have shown that H3T3P is indeed subject to stringent temporal controls during mitosis. The H3T3P mark is undetectable during G2 phase. Upon entry to mitosis, sister chromatids enriched with pre-existing H3-GFP histone begin to show H3T3 phosphorylation prior to sister chromatids enriched with newly synthesized H3-mKO. As the cell continues to progress toward metaphase, H3T3P signal begins to appear on sister chromatids enriched with newly synthesized H3-mKO. Such a tight regulation of H3T3P is compromised when levels of H3T3P are altered due to the incorporation of mutant H3T3A or H3T3D. Incorporation of the H3T3A mutant results in a significant decrease in the levels of H3T3P on sister chromatids throughout mitosis, such that neither sister becomes enriched with H3T3P as the GSC progresses toward metaphase. Conversely, incorporation of the H3T3D mutant would result in seemingly elevated levels of H3T3P early in mitosis. Although H3T3A and H3T3D act in different ways, both mutations significantly disrupt the highly regulated temporal patterns associated with H3T3 phos-phorylation, the result of which is randomized H3 inheritance patterns and germ cell defects in testes expressing either H3T3A or H3T3D.

As described in detail below, to further evaluate the extent of H3T3A and H3T3D roles in the segregation of sister chromatids enriched with different populations of H3 during mitosis (FIG. 5B, step two), all possible segregation patterns in male GSCs were modeled and these estimateswere compared to the experimental results. To simplify the calculations, two important assumptions were made: first, nucleosomal density was assumed to be even throughout the genome. This assumption allows the inference that the overall fluorescent signal contributed by each chromosome is proportional to their respective number of DNA base pairs. Second, by quantifying pre-existing H3-GFP asymmetry in anaphase and telophase GSCs, the estimate of the establishment of H3-GFP asymmetry is 4-fold biased, i.e., 80% on one set of sister chromatids and 20% on the other set of sister chromatids, based on quantification of GFP signal in anaphase (GFP GSC side/GB side=4.5) and telophase (GFP GSC side/GB side=3.8) GSCs (Tran et al., 2012). With these two simplifying assumptions, both GFP and mKO ratios were calculated among all 64 possible combinations (FIG. 27, Table 2A and Table 2B: 2 (for X-ch)×2 (for Y-ch)×4 (for 2nd ch)×4 (for 3rd ch)=64 combinations in total). If asymmetry is defined as a greater than 1.5-fold difference in fluorescence intensity, then based on a model of randomized sister chromatid segregation, a symmetric pattern should appear for 53.1% (34/64) of GSC-GB pairs whereas both conventional and inverted asymmetric patterns should occur with equal frequencies and account for 18.7% (12/64) of total GSC-GB pairs. The remaining 9.4% (6/64) of GSC-GB pairs should produce histone inheritance patterns with a 1.45- to 1.55-fold difference in signal intensity (predicted ratios in FIG. 22K).

Figure 22:
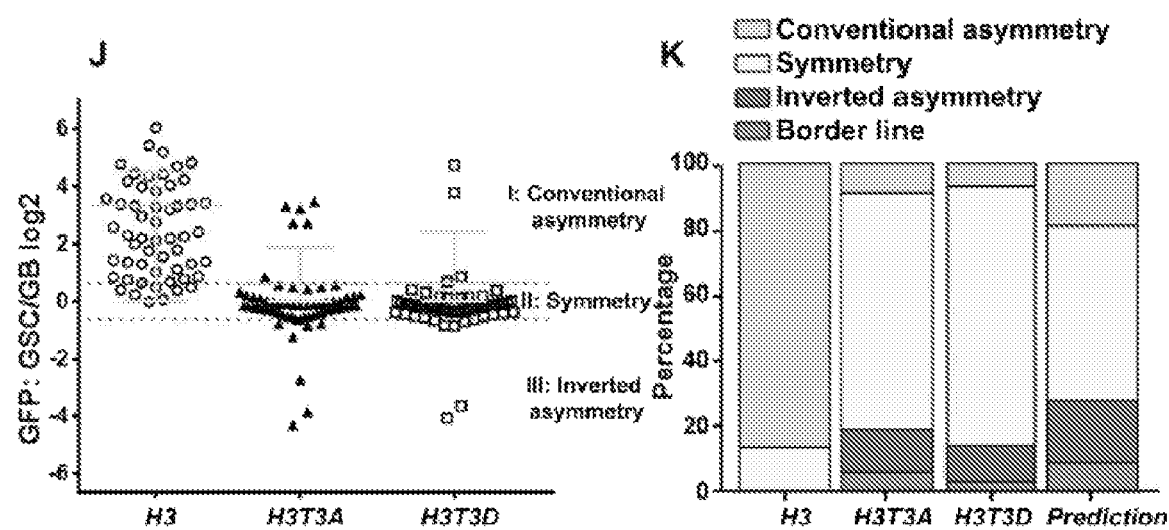
FIG. 22J-FIG. 22K is a series of graphs depicting that expression of H3T3A or H3T3D changes pre-existing and newly synthesized H3 distribution patterns in post-mitotic GSC-GB pairs.

This estimation is close to experimental data, as described herein, in both H3T3A- and H3T3D-expressing testes (FIG. 22J and FIG. 22K; Table 1). Of the 64 quantified postmitotic GSC-GB pairs in nos>H3T3A testes, 71.9% showed symmetric inheritance pattern. Conventional and inverted asymmetric patterns were detected at 9.4% and 12.5%, respectively, and 6.3% at the borderline. Similarly, of the 57 quantified post-mitotic GSC-GB pairs in nos>H3T3D testes, 79.0% showed symmetric inheritance pattern. Conventional and inverted asymmetric patterns were detected at 7.0% and 10.5%, respectively with 3.5% of pairs at the borderline. Some differences between predicted ratios and our experimental data could be due to the simplified assumptions, the limited sensitivity of our measurement, and/or some coordinated chromatid segregation modes that bias the eventual read-out (Yadlapalli and Yamashita, 2013). In summary, comparison between the modeling ratios and experimental data described herein suggest that loss of the tight control of H3T3 phosphorylation in GSCs randomizes segregation of sister chromatids enriched with different populations of H3.

If the temporal separation in the phosphorylation of H3T3 on epigenetically distinct sister chromatids facilitates their proper segregation and inheritance during asymmetric cell division, it is likely that mutations of the Haspin kinase will also affect the temporal control of H3T3 phosphorylation. In the context of H3T3A, where the levels of H3T3P are already reduced, a further decrease in H3T3P by reducing Haspin levels should limit the GSC's ability to distinguish between sister chromatids enriched with distinct H3. Indeed, haspin mutants enhance the phenotypes in nos>H3T3A testes. A different situation appears in the context of H3T3D where sister chromatids experience seemingly elevated levels of H3T3P at the start of mitosis. These elevated H3T3P levels may be exacerbated by the phosphorylation activity of the Haspin kinase. Therefore, it is conceivable that by halving the levels of the Haspin kinase, H3T3 phosphorylation should be reduced to a level more closely resembling wild-type. In this way, some of the temporal specificity that is lost in the H3T3D mutant is restored, resulting in suppression of the phenotypes observed in nos>H3T3D testes. An exciting topic for future study would be to further explore how exactly Haspin phosphorylates H3T3 in the context of chromatin and whether H3T3A and H3T3D mutations act synergistically or antagonisti¬cally in regulating asymmetric sister chromatids segregation through differential phosphorylation of a key histone residue.

Also described herein is the potential connection between asymmetric histone inheritance and another phe-nomenon reported by several investigators: selective DNA strand segregation (reviewed by Evano and Tajbakhsh, 2013; Rando, 2007; Tajbakhsh and Gonzalez, 2009). Recent development of the chromosome orientation fluorescence in situ hybridization (CO-FISH) technique (Falconer et al., 2010) allows study of selective chromatid segregation at single-chromosome resolution. Using this technique in mouse satellite cells, it has been demonstrated that all chromosomes are segregated in a biased manner, such that pre-existing template DNA strands are preferentially retained in the daughter cell that retains stem cell identity. Interestingly, this biased segregation becomes randomized in progenitor non-stem cells (Rocheteau et al., 2012). Using CO-FISH in Drosophila male GSCs, sex chromosomes have been shown to segregate in a biased manner. Remarkably, sister chromatids from homologous autosomes have been shown to co-segregate independent of any specific strand preference (Yadlapalli and Yamashita, 2013). Thus, as described herein, there is a possible epigenetic source guiding the coordinated inheritance of Drosophila homologous autosomes. In many cases of biased inheritance, researchers have speculated about the existence of a molecular signature that would allow the cell to recognize and segregate sister chromatids bearing differential epigenetic information (Klar, 1994, 2007; Lansdorp, 2007; Rando, 2007; Yen-nek and Tajbakhsh, 2013). However, prior to the invention described herein, the identity of such a signature has remained elusive. Described herein is experimental evidence demonstrating that a tightly-controlled histone modification, H3T3P, is able to distinguish sister chromatids and coordinate their segregation.

Epigenetic processes play important roles in regulating stem cell identity and activity. Failure to appropriately regulate epigenetic information may lead to abnormalities in stem cell behaviors, which underlie early progress toward diseases such as cancer and tissue degeneration. Priro to the invention described herein, due to the crucial role that such processes play in regulating cell identity and behavior, the field has long sought to understand whether and how stem cells maintain their epigenetic memory through many cell divisions. The results described herein suggest that the asymmetric segregation of pre-existing and newly synthesized H3-enriched chromosomes may function to determine distinct cell fates of GSCs versus differentiating daughter cells.

Pharmaceutical Therapeutics

The invention provides pharmaceutical compositions for use as a therapeutic. In one aspect, the composition is administered systemically, for example, formulated in a pharmaceutically-acceptable buffer such as physiological saline. Preferable routes of administration include, for example, instillation into the bladder, subcutaneous, intravenous, intraperitoneal, intramuscular, or intradermal injections that provide continuous, sustained levels of the composition in the patient. Treatment of human patients or other animals is carried out using a therapeutically effective amount of a therapeutic identified herein in a physiologically-acceptable carrier. Suitable carriers and their formulation are described, for example, in Remington's Pharmaceutical Sciences by E. W. Martin. The amount of the therapeutic agent to be administered varies depending upon the manner of administration, the age and body weight of the patient, and with the clinical symptoms of the neoplasia or infection. Generally, amounts will be in the range of those used for other agents used in the treatment of other diseases associated with neoplasia or infection, although in certain instances lower amounts will be needed because of the increased specificity of the compound. A compound is administered at a dosage that enhances an immune response of a subject, or that reduces the proliferation, survival, or invasiveness of a neoplastic cell as determined by a method known to one skilled in the art.

Formulation of Pharmaceutical Compositions

The administration of compositions for the treatment of a condition associated with endothelial dysfunction may be by any suitable means that results in a concentration of the therapeutic that, combined with other components, is effective in ameliorating, reducing, or stabilizing a condition associated with endothelial dysfunction. The composition may be contained in any appropriate amount in any suitable carrier substance, and is generally present in an amount of 1-95% by weight of the total weight of the composition. The composition may be provided in a dosage form that is suitable for parenteral (e.g., subcutaneously, intravenously, intramuscularly, intravesicularly or intraperitoneally) administration route. The pharmaceutical compositions may be formulated according to conventional pharmaceutical practice (see, e.g., Remington: The Science and Practice of Pharmacy (20th ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York).

Human dosage amounts can initially be determined by extrapolating from the amount of compound used in mice or nonhuman primates, as a skilled artisan recognizes it is routine in the art to modify the dosage for humans compared to animal models. In certain embodiments it is envisioned that the dosage may vary from between about 0.1 µg compound/kg body weight to about 5000 µg compound/kg body weight; or from about 1 µg/kg body weight to about 4000 µg/kg body weight or from about 10 µg/kg body weight to about 3000 µg/kg body weight. In other embodiments this dose may be about 0.1, 0.3, 0.5, 1, 3, 5, 10, 25, 50, 75, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1600, 1700, 1800, 1900, 2000, 2500, 3000, 3500, 4000, 4500, or 5000 µg/kg body weight. In other embodiments, it is envisaged that doses may be in the range of about 0.5 µg compound/kg body weight to about 20 µg compound/kg body weight. In other embodiments the doses may be about 0.5, 1, 3, 6, 10, or 20 mg/kg body weight. Of course, this dosage amount may be adjusted upward or downward, as is routinely done in such treatment protocols, depending on the results of the initial clinical trials and the needs of a particular patient.

Pharmaceutical compositions are formulated with appropriate excipients into a pharmaceutical composition that, upon administration, releases the therapeutic in a controlled manner. Examples include single or multiple unit tablet or capsule compositions, oil solutions, suspensions, emulsions, microcapsules, microspheres, molecular complexes, nanoparticles, patches, and liposomes.

Kits or Pharmaceutical Systems

Pharmaceutical compositions may be assembled into kits or pharmaceutical systems for use in arresting cell cycle in rapidly dividing cells, e.g., cancer cells. Kits or pharmaceutical systems according to this aspect of the invention comprise a carrier means, such as a box, carton, tube, having in close confinement therein one or more container means, such as vials, tubes, ampoules, bottles, syringes, or bags. The kits or pharmaceutical systems of the invention may also comprise associated instructions for using the kit.

As described in detail below, mitosis-specific epigenetic mark H3T3P distinguishes preexisting versus newly synthesized H3 to regulate their proper segregation during cell division. Mutating this threonine to either unphosphorylatable alanine or phosphor-mimic aspartic acid leads to missegregation of sister chromatids and dramatic germ cell defects including germline tumor and germ cell loss. The results presented herein highlight the importance of proper epigenetic inheritance in stem cells.

The data presented herein demonstrate that a mitotic-specific H3T3P mark acts as an epigenetic landmark that distinguishes sister chromatids with identical genetic code, but different epigenetic information. Initiated by this recognition, different epigenetic information is inherited differentially to the two daughter cells derived from one asymmetric cell division, which allows these two cells to take distinct fates. Loss of this epigenetic inheritance might lead to defects in both GSC maintenance and GB differentiation, suggesting that both cells need this active partitioning process to either 'remember' or 'reset' their molecular properties.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the assay, screening, and therapeutic methods of the invention, and are not intended to limit the scope of what the inventors regard as their invention.

Example 1: Materials and Methods

Fly Strains and Husbandry

Fly stocks were raised using standard Bloomington medium at 18° C., 25° C., or 29° C. as noted. The following fly stocks were used: hs-flp on the X chromosome (Bloomington Stock Center BL-26902), haspin TRiP line (Bloomington Stock 35276), Df(haspin) (Bloomington Stock 7155), haspin$^{M109386}$ (Bloomington Stock 53099), UAS-upd on the 2nd chromosome (Terry et al., 2006 Dev Biol, 294, 246), nos-Gal4 on the 2nd chromosome (Van Doren et al., 1998 Curr Biol 8, 243, bam-Gal4 on the 2nd chromosome (Eun et al., 2014 Science, 343, 1513).

Generation of Fly Strains with Different Switchable Dual-Color Transgenes

Standard procedures were used for all molecular cloning experiments. Enzymes used for plasmid construction were obtained from New England Biolabs (Beverly, Mass.). H3T3A and H3T3D point mutations were generated with quick change site-directed mutagenesis kit (Agilent Technologies 200521) according to manufacturer's instructions, based on the plasmids containing wild-type H3 sequences described in (Tran et al., 2012 Science 338, 679). Similar tagged histone proteins were used for previous studies (K. Ahmad and S. Henikoff, 2002 Mol Cell 9, 1191; K. Ahmad and S. Henikoff, 2001 J Cell Biol 153, 101). The H3T3A/D-mKO fusion sequences were recovered as an XbaI flanked fragment and were subsequently inserted into the XbaI site of the UASp plasmid to construct the UASp-H3T3A/D-mKO plasmid. The H3T3A/D-GFP fusion sequences were inserted to pBluescript-FRT-NheI-SV40 PolyA-FRT plasmid at the unique NheI site. The entire FRT-H3T3A/D-GFP-SV40 PolyA-FRT sequences were then subcloned into the UASp-H3T3A/D-mKO plasmid, as described previously (Tran et al., 2012 Science 338, 679), digested by NotI and BamHI (note: BglII and BamHI produce compatible cohesive ends). The final UASp plasmids were introduced to w$^{1118}$ flies by P-element-mediated germline transformation (Bestgene Inc.).

Heat Shock Scheme

Flies with UASp-FRT-H3-GFP-PolyA-FRT-H-mKO or their mutant transgenes (H3T3A or H3T3D, e.g., UASp-FRT-H3T3A/D-GFP-PolyA-FRT-H3T3A/D-mKO) were paired with nos-Gal4 drivers. Flies were raised at 18° C. throughout development until adulthood to avoid pre-flip (Tran et al., 2012 Science 338, 679). Before heat shock, 0-3 day old males were transferred to vials that had been air dried for 24 hours. Vials were submerged with all air area (i.e., up to the plug) underneath water in a circulating 37° C. water bath for two hours and recovered in a 29° C. incubator for indicated time before dissection and immunostaining experiments.

Temperature Shift Assay to Induce Germline Tumor in Adult Flies

Flies with UASp-FRT-H3-GFP-PolyA-FRT-H-mKO or their mutant transgenes (H3T3A or H3T3D, e.g., UASp-FRT-H3T3A/D-GFP-PolyA-FRT-H3T3A/D-mKO) paired with either nos-Gal4 or bam-Gal4 driver were raised at 18° C. throughout development until adulthood. Newly enclosed males were collected and shifted to 29° C. for indicated time before dissection and immunostaining experiments.

Immunostaining Experiments

Immunofluorescence staining was performed using standard procedures (Tran et al., 2012 Science 338, 679; Hime et al., 1996 J Cell Sci 109 (Pt 12), 2779). Primary antibodies were mouse anti-α spectrin (1:50, DSHB 3A9), mouse anti-Fas III (1:50, DSHB, 7G10), mouse anti-Armadillo (1:100; DSHB, N2 7A1 clone), rabbit anti-H3T3P (1:200, Millipore 05-746R), mouse anti-H3S10P (1:200; Millipore, #05-806), anti-CID (1:100; gift from Dr. Sylvia Erhardt, University of Heidelberg, Germany), and rabbit anti-Vasa (1:200; Santa Cruz SC-30210). Secondary antibodies were the Alexa Fluor-conjugated series (1:200; Molecular Probes). Lysotracker (Invitrogen L7528) was applied according to manufacturer recommendation. Images were taken using the Zeiss LSM 510 META or Zeiss LSM 700 Multiphoton confocal microscope with a 40× or 63× oil immersion objectives and processed using Adobe Photoshop software.

EdU Incorporation to Label GSC-GB Pair at S-Phase

EdU labeling of the GSC-GB pairs at S phase was performed using Click-iT EdU Alexa Fluor 647 Imaging Kit (Life Science C10640) according to manufacturer's instructions. Dissected testes were immediately incubated in S2 medium with 100 μM EdU for 30 minutes at room temperature. The testes were subsequently fixed and proceed to primary antibodies (anti-FasIII, anti-a spectrin and anti-Vasa) incubation. Fluorophore conjugation to EdU was performed along manufacturer's instructions and followed by secondary antibodies incubation. The addition of EdU facilitates recognition of the GSC-GB pairs undergoing active DNA synthesis from those without EdU, which might be arrested due to the heat shock treatment. The cell cycle progression is important for the incorporation and segregation of preexisting versus newly synthesized H3.

Lattice Light Sheet Microscopy

Light sheet measurements were performed using a massively parallel linear array of non-diffracting beams that coherently interfere to create a 2D optical lattice confined to a single plane (Gao et al., 2014 Nat Protoc 9, 1083; B. C. Chen et al., 2014 Science 346, 1257998). This structured was then oscillated rapidly within the plane to create time-averaged uniform excitation in a 400 nm thick section across the entire field of view. The desired coherent pattern was generated using a spatial light modulator (SXGA-3DM, Forth Dimension Displays) that was conjugate to the sample plane, and that projected a binarized version of the desired pattern to be imaged at the sample. The fluorescence generated within the specimen by the light sheet was collected by an objective (Nikon, CFI Apo LWD 25XW, 1.1 NA, 2 mm WD) and then imaged on a fast camera (ORCA-flash4.0, Hamamatsu). Four lasers of excitations wavelengths 405 nm, 488 nm, 532 nm, and 640 nm were used, and a multi-band emission filter (Semrock, FF02-435/40-25, FF03-525/50-25, FF01-562/40-25, BLP01-647R-25) rejected the excitation wavelengths. The fixed sample was mounted on 5 mm coverslip through the light sheet at 50 ms exposure per 2D image. The excitation numerical aperture of light sheet is 0.42 for outer ring and 0.325 for inner one. The image voxel is 104×104×250 nm in x, y, z respectively. Multi-color experiments were performed by switching the color stack by stack. The 3D images obtained by sweeping the light sheet plane by plane through the specimen were deconvolved using a Richardson-Lucy algorithm.

Immunoblot Experiments

Histone H3 antibody (Abcam Cat # ab1791), H4 antibody (Abcam Cat # ab10158), and GFP antibody (Abcam Cat # ab13970) were used for immunoblot analyses. 15 testes were dissected in 1×PBS and transferred to 1×RIPA to prepare for the lysate of each sample. Novex 4-20% Tris-Glycine Mini Protein Gels (Life Science EC6025BOX) were used for SDS-PAGE. Rabbit anti-histone H3 (1:1000 Abcam ab1791) and Chicken anti-GFP (1:1000, Abcam ab13970) were used as primary antibodies. Goat anti-Chicken IgG (1:1000, Abcam ab97135) and goat anti-rabbit IgG (1:1000, Santa Cruz SC-2030) were used as secondary antibodies.

Quantification of GFP and mKO Intensity

No antibody was added to enhance either GFP or mKO signal. Values of GFP and mKO intensity were calculated using Image J software. DAPI signal was used to determine the area of nucleus for measuring both GFP and mKO fluorescent signals, the raw reading was subsequently adjusted by subtracting fluorescence signals in the hub region used as background in both GSC and GB nuclei and compared between each other.

Male Fly Fertility Test

For the fertility test, newly enclosed single nos>H3T3A-GFP males were mated with three y,w virgin females and at least ten crosses were set up simultaneously. Similar crosses were also made for the nos>H3-GFP control males. All crosses were kept at 29° C. and males were transferred into new vials with three y,w virgin females every five days until they were 20-day old. The progenies of each cross was counted for three days consecutively after they enclosed. Vials which did not contain all four flies alive (one male and three females) at the end of each 5-day mating period, were excluded from the counting and the plotting.

Transcriptome Profiling (RNAseq) and Data Analyses

Sample Isolation and mRNA Library Preparation

Arcturus Picopure RNA isolation kit (Life Tecknologies, KIT0204) was utilized to prepare total RNA from dissected testis samples. Sequencing libraries were prepared by following the Illumina TruSeq RNA sample prep kit V2 (Illumina, RS-122-2001). Five H3T3A samples and two nos-Gal4; UAS-upd (nos>upd) (24, 42, 43) samples were sequenced on Illumina Mi-seq or Hi-seq 2500 sequencer. The Hi-seq 2500 runs were single-end 50 cycle sequencing, and the Mi-seq runs were pair-end 75*2 cycle sequencing. In the analysis, the pair-end reads were merged and treated as single-end. In addition, there are two transcriptome profiles from a previous published work (Gan et al., 2010 Cell Res 20, 763), one from wild-type testis tissue sample and one from bag-of-marbles (bam) mutant testis tissue sample. Thus, a total of nine samples/data were input for the transcriptome profiling analysis.

The Alignment to Fly Genome and Gene Mapping

The reads retrieved from multiple sequencing runs were examined by fastqc quality control software (bioinformatics.babraham.ac.uk/projects/fastqc/). The reads passed quality filter were mapped back to *Drosophila melanogaster* genome (dm3) (Flybase dmel_r5.43, as of January 2012, ftp.flybase.net/releases/FB2012_01/dmel_r5.43/). Bowtie aligner [version 0.12.7 (Langmead et al., 2009 Genome Biol 10, R25)] was utilized with the following configuration (-a --phred33-quals -n 2 -e 70-128 -m 1 --best -strata) which is basically allowing two mismatches and only one alignment site. Each read was then assigned into gene regions. The annotation for protein coding genes, ribosomal RNAs, tRNAs, snoRNA, snRNAss, pre_miRNAs, and other non-coding RNAs were retrieved from Flybase database (as of January 2012, ftp.flybase.net/releases/FB2012_01/dmel_r5.43/). The exons from different alternative splicing isoforms were merged to find the maximum genome coverage regions per gene. When a read is mapped to a region with more than one gene, i.e., one merged exon region overlapping with a non-coding gene, the count is split as equal possibilities into these two genes, half count for each. A matrix file with the number of reads assigned into each gene per sample was prepared for the following data analysis.

Estimation of Transcription Level and Other Analysis

The edgeR software package (Robinson et al., 2010 Bioinformatics 26, 139) in R was utilized to find the normalization factors for each sample with various sizes (by the TMM (Trimmed Mean of M value) and upper quantile normalization methods). The edgeR method models short reads into negative binomial distribution and estimates the biological replicate variance (dispersion). Tag-wise dispersion estimation was performed in "H3T3A", "nos-UPD", "barn" and "wild-type" four groupings of read count profiles. Quantity term "corrected RPKM (cRPKM)" was introduced by the formula: pseudo.alt*1e±09/(length of merged transcripts)/(common.lib.size). The common.lib.size was calculated from the calcNormFactors function of edgeR, which performs TMM and upper quantile normalization methods and set a reference library. The pseudo.alt contains read counts after normalization across the input multiple profiles. The pseudo.alt was calculated by edgeR using quantile normalization and maximum likelihood method. The pseudo.alt contains pseudo read counts after correcting the library size and composition difference.

Figure 13:
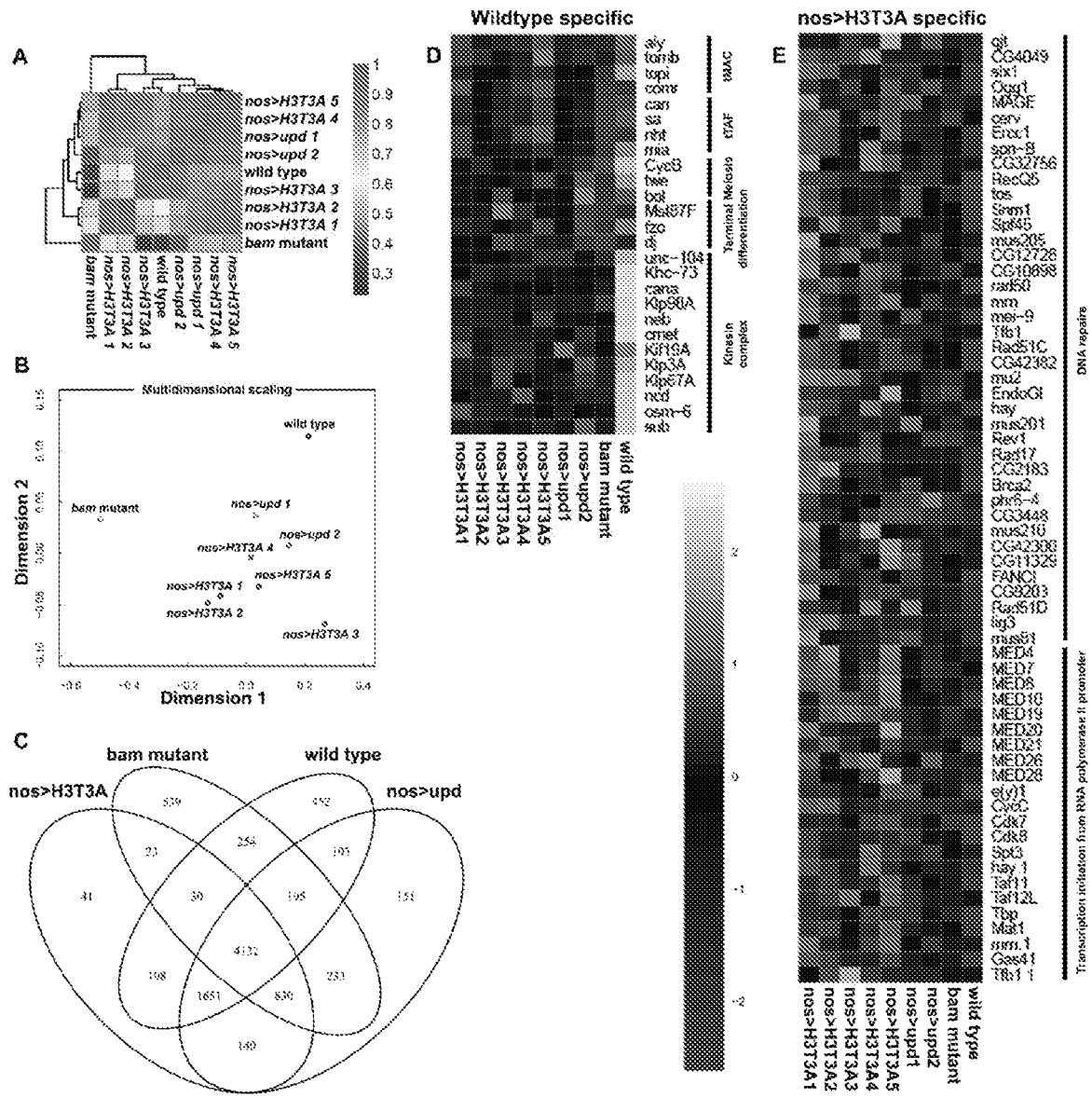
FIG. 13A-FIG. 13E is a series of matrices, a dot plot and a venn diagram.

After cRPKM calculation, gene expression levels per sample were pair-wisely compared with spearman correlation (correlation coefficient rho). A pair-wise inter-profile distance was defined as (1-rho) and set up a distance matrix. A dimension reduction method, multidimensional scaling in R (stat.ethz.ch/R-manual/R-devel/library/stats/html/cmdscale.html), was utilized to visualize the global similarity relationship among the nine samples (five nos>H3T3A samples, two nos>upd samples, one barn sample and one wild-type sample), as shown in FIG. 13A-FIG. 13B.

In order to identify aberrant gene expression in nos>H3T3A testes, similarity among all nos>H3T3A samples is observed by hierarchical clustering. Kmeans method was utilized, with $\log_2$ transformation and Z score scaling. A Venn diagram shown in FIG. 13C was drawn to illustrate the actively expressed genes in each genotype using cRPKM>=20 as a cutoff. In this scenario, the five nos>H3T3A samples were combined and the two nos>upd samples were combined. The specific cluster with high expression in wild-type testes and all nos>H3T3A samples was piped into GO enrichment analysis with Benjamini correction (q_value), as shown in FIG. 13D and FIG. 13E, respectively.

Example 2: Histone H3 Thr 3 Phosphorylation Regulates Asymmetric H3 Inheritance and Male Germline Activity in *Drosophila*

Described herein is a two-step model to explain this asymmetric H3 inheritance. First, prior to mitosis, preexisting and newly synthesized H3 are differentially distributed at the two sets of sister chromatids. Second, during mitosis, the set of sister chromatids containing preexisting H3 is segregated to GSCs, while the set of sister chromatids enriched with newly synthesized H3 is segregated to the GB that differentiates (FIG. 5B; Tran et al., 2012 Science 338, 679; Tran et al., Chromosome Res 21, 255).

Figure 1:
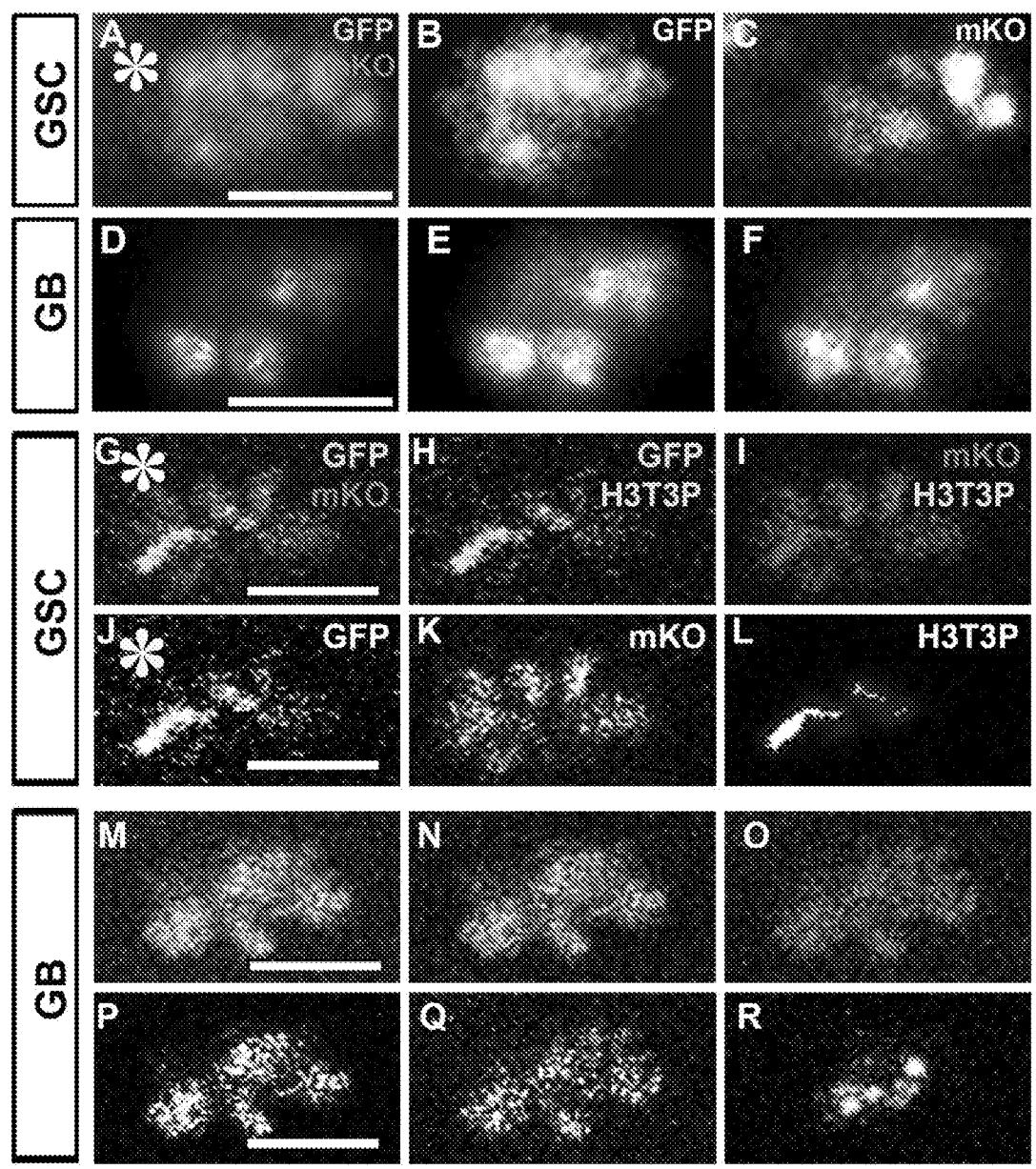
FIG. 1A-FIG. 1R is a series of photomicrographs showing that phosphorylation at threonine 3 of histone 3 (H3T3P) distinguishes preexisting H3-green fluorescent protein (GFP) (green) from newly synthesized H3-mKusabira Orange (mKO; red) in Drosophila male germline stem cells (GSCs). Also shown are a GSC (FIG. 1A-FIG. 1C) and a gonialblast (GB) (FIG. 1D-FIG. 1F) at prophase. Also shown are immunostaining H3T3P signals in a GSC (FIG. 1G-FIG. 1L) and a GB (FIG. 1M-FIG. 1R) at prometaphase. Asterisk: hub. Scale bars: 5 µm.
Figure 6:
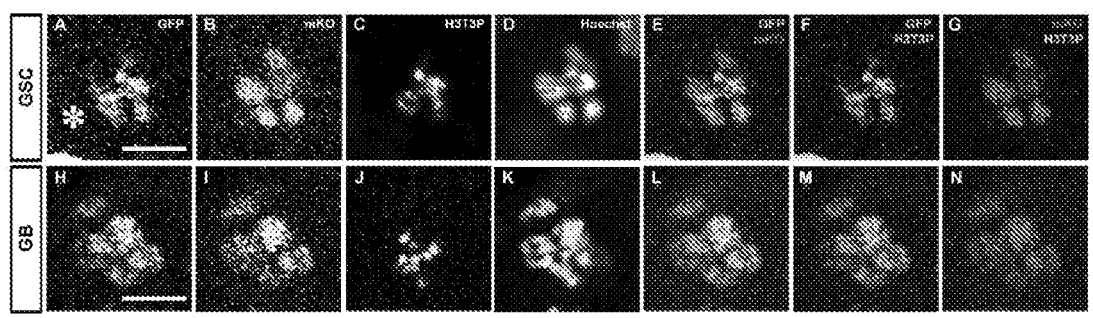
FIG. 6A-FIG. 6N is a series of photomicrographs showing that H3-GFP and H3-mKO signals are separable in prophase GSC, but not in the GB control. Shown is immunostaining using anti-H3T3P: a prophase GSC (FIG. 6A-FIG. 6G) and a prophase GB (FIG. 6H-FIG. 6N): both were undergoing mitosis 18 hours after heat shock-induced genetic switch from H3-GFP-encoding to H3-mKO-encoding sequences. Asterisk: hub. Scale bars: 5 μm.
Figure 7:
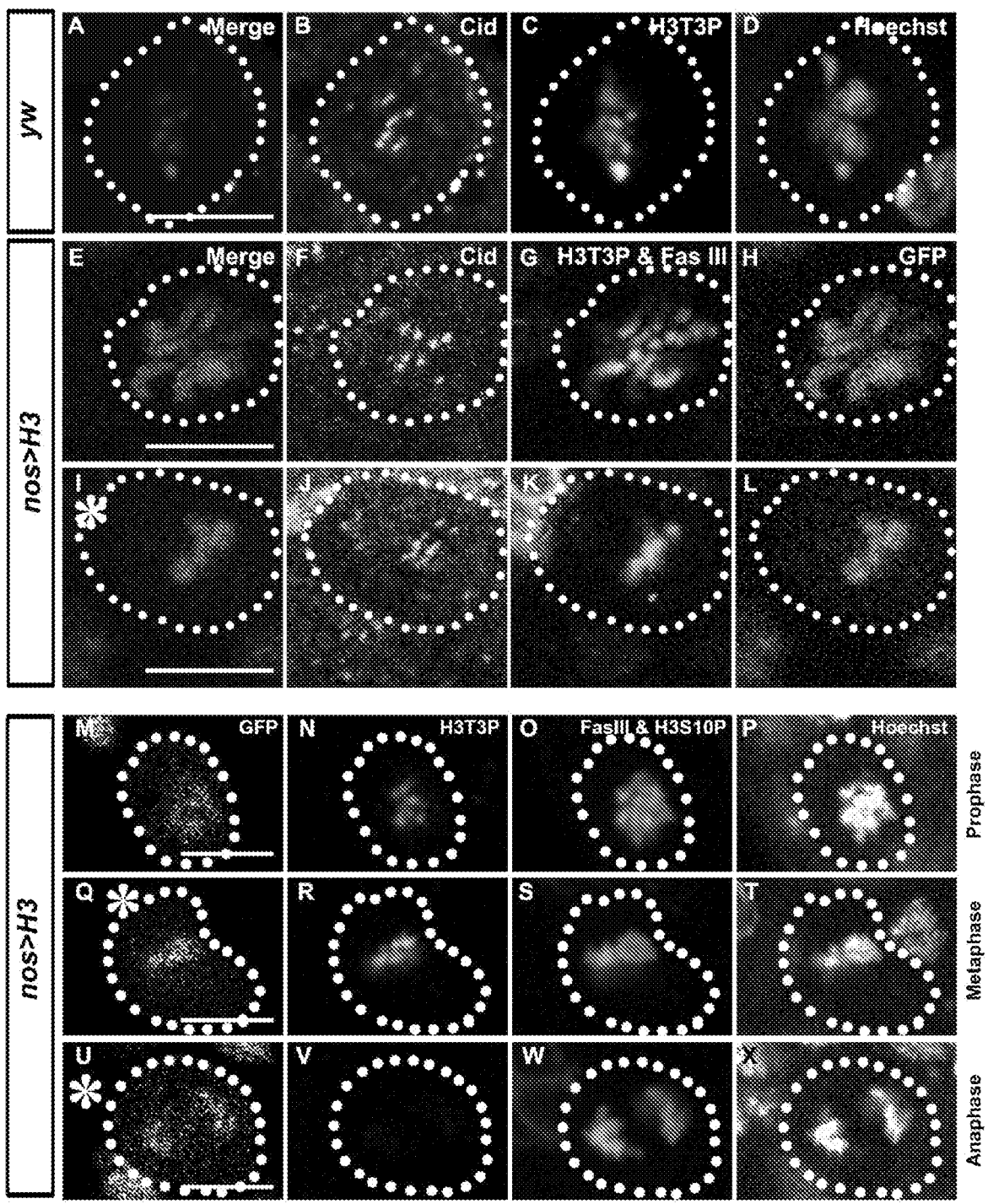
Figure 8:
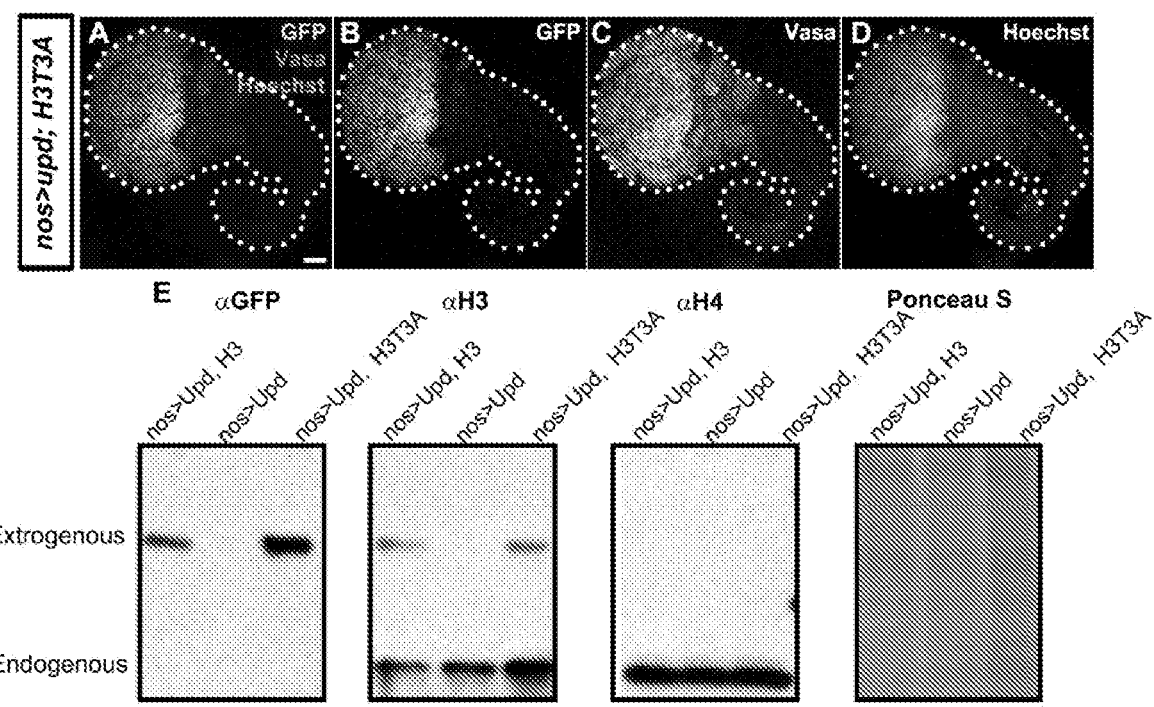
FIG. 8A-FIG. 8E is a series of photomicrographs and immunoblots showing abundant endogenous histone proteins in nos>upd; H3T3A-GFP testes.

To examine this model, a temporally controlled dual-color system was used to label preexisting H3 with GFP (green fluorescent protein) and newly synthesized H3 with mKO (monomeric Kusabira Orange) precisely (Tran et al., 2012 Science 338, 679). Asymmetric segregation of H3-GFP and H3-mKO were clearly visualized in anaphase and telophase GSCs imaged during the second mitosis following heat shock-induced H3-GFP- to H3-mKO-coding sequences switch (Tran et al., 2012 Science 338, 679). As described herein, H3-GFP and H3-mKO signals are already separable in a prophase GSC (FIG. 1A-FIG. 1C; FIG. 6A-FIG. 6B, and FIG. 6E), but not in a control GB (FIG. 1D-FIG. 1F; FIG. 6H-FIG. 6I, and FIG. 6L), which is consistent with the hypothesis that their differential distribution is established in GSCs prior to mitosis (Step one in FIG. 5B). By contrast, such a separation was not detected using a H3.3 dual-color transgene under the same heat-shock regime (FIG. 23A), consistent with H3.3 being inherited symmetrically (Tran et al., 2012).

The phosphorylation at threonine 3 of H3 (H3T3P) is enriched on mitotic chromosomes (Wang et al., 2010 Science 330, 231; Kelly et al., 2010 Science 330, 235; and Yamagishi et al., 2010 Science 330, 239) and has been proposed to function to ensure proper chromosome congression to the metaphase plate for reliable segregation of sister chromatids during anaphase (Dai et al., 2005 Genes Dev 19, 472). When immunostaining experiments were performed using an H3T3P-specific antibody, it was identified that H3-GFP (FIG. 1G an FIG. 1J), but not H3-mKO (FIG. 1G and FIG. 1K), is co-labeled by H3T3P (FIG. 1H-FIG. 1I, and FIG. 1L) in a prometaphase GSC. A similar observation was made in a prophase GSC (FIG. 6C, and FIG. 6F-FIG. 6G), suggesting that preexisting H3-GFP and newly synthesized H3-mKO are not phosphorylated simultaneously. By contrast, H3-GFP signals and H3-mKO signals are not separable and H3T3P does not distinguish them in a control GB (FIG. 1M-FIG. 1R; FIG. 6J, and FIG. 6M-FIG. 6N). Furthermore, when sister chromatids congressed to the equator in metaphase GSCs, such a distinction became un-detectable (FIGS. 20U-20Z). Therefore, H3T3P acts as an epigenetic mark to distinguish sister chromatids enriched with preexisting H3 from those enriched with newly synthesized H3. The H3T3P immunostaining signal observed is not restricted to the centromeric region (FIG. 7A-FIG. 7L), in contrast to centromere-specific H3T3P signal reported in mammalian cells (Wang et al., 2010 Science 330, 231). Moreover, H3T3P is only detectable in prophase (FIG. 7G, and FIG. 7M-FIG. 7P) to metaphase (FIG. 7Q-FIG. 7T), but not in anaphase (FIG. 7U-FIG. 7X) germ cells, consistent with previous report in other insect cells (C. Escriba and C. Goday, 2013 J Cell Sci 126, 3214).

Figure 2:
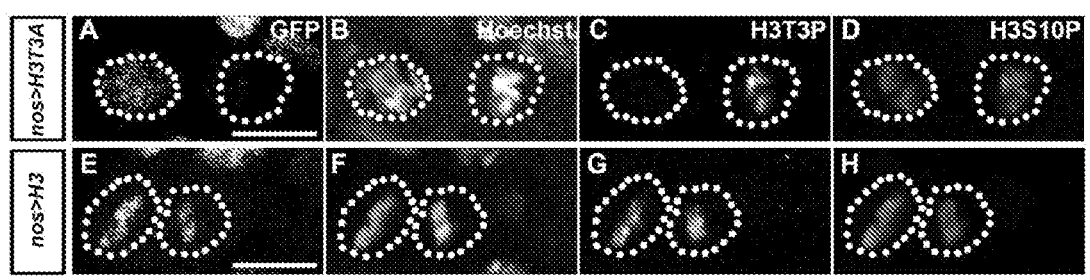
FIG. 2A-FIG. 2H is a series of photomicrographs showing that expression of an H3T3A transgene greatly reduces H3T3P in mitotic germ cells. Specifically, these panels show immunostaining using anti-H3T3P and anti-H3S10P: outlined are mitotic germ cells expressing either nos>H3T3A-GFP (FIG. 2A-FIG. 2D) or nos>H3-GFP (FIG. 2E-FIG. 2H). Scale bars: 10 µm.

To understand the function of H3T3P in germ cells, fly lines were generated with an H3-GFP transgene carrying a point mutation that converts T3 to the unphosphorylatable Alanine (Ala or A, H3T3A). Expression of the H3T3A-GFP transgene in early germ cells by the nanos-Gal4 [nos-Gal4, (Van Doren et al., 1998 Curr Biol 8, 243)] driver greatly reduced the H3T3P signal (FIG. 2A-FIG. 2C). This reduction of immunostaining signal was specific to H3T3P, as immunostaining using antibodies against mitosis-enriched H3S10P (Ser10-phosphorylation of H3) showed normal signals in H3T3A-expressing cells (FIG. 2D). Because endogenous H3 are still abundant in testes where H3T3A is expressed in almost all germ cells (FIG. 8A-FIG. 8E), the absence of H3T3P signal suggests a dominant negative effect of H3T3A. The dominant negative effect of point mutations of H3 has recently been identified for multiple residues (Lewis et al., 2013 Science 340, 857; Herz et al., 2014 Science 345, 1065). By contrast, expression of a wild-type H3 had no effect on either the H3T3P (FIG. 2E-FIG. 2G) or the H3S10P (FIG. 2H) signal, confirming that it is not a transgene-induced effect.

Figure 9:
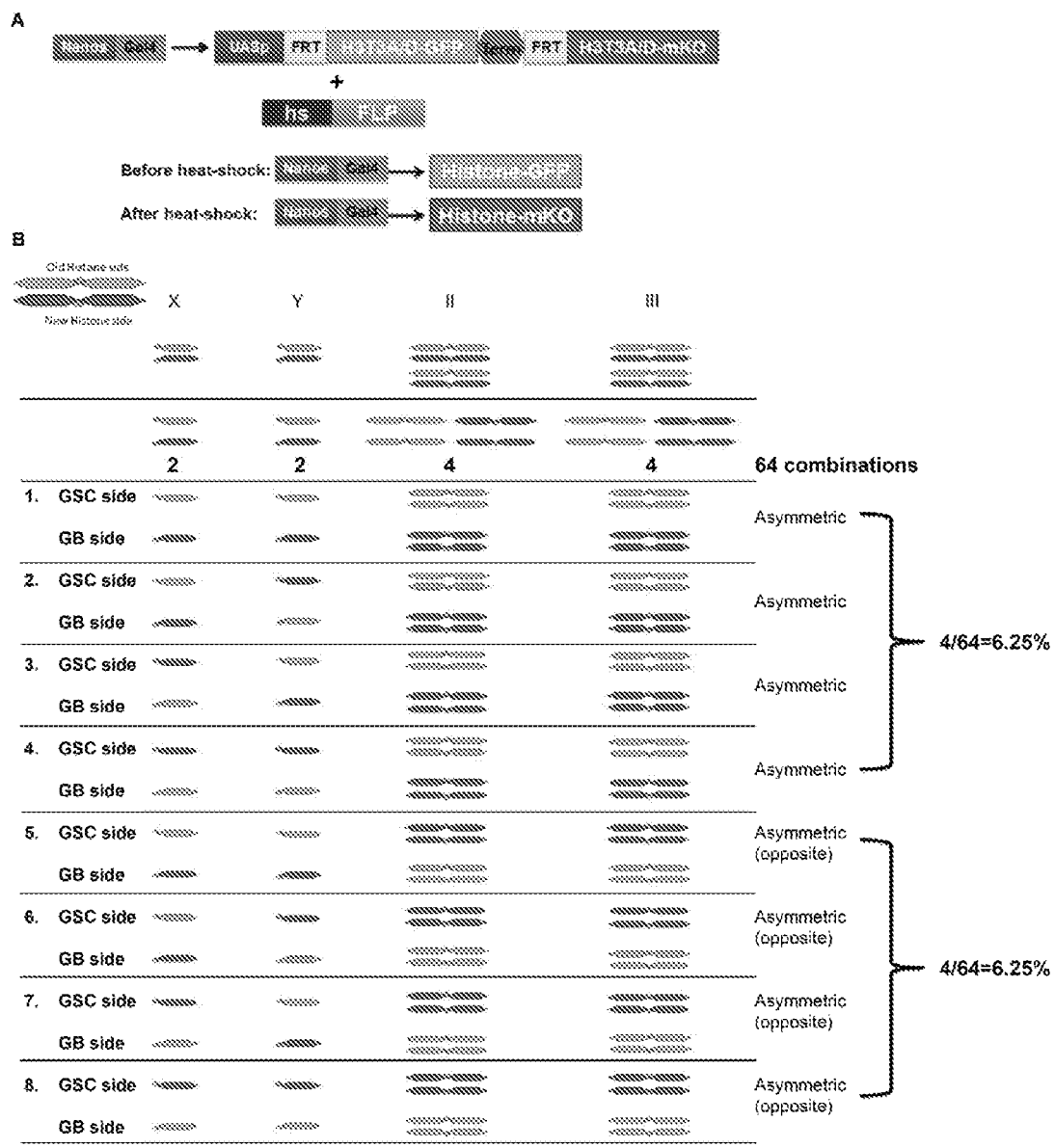
FIG. 9A-FIG. 9B is a series of schematics showing the predicted pattern when sister chromatids enriched with either preexisting H3-GFP (old, green) or H3-mKO (new, red) are segregated randomly during GSC division.

It was next identified whether H3T3A affects asymmetric H3 segregation during GSC asymmetric division using the dual-color labeling system (FIG. 9A). Because mitotic GSCs account for less than 2% of all GSCs (Tran et al., 2012 Science 338, 679; X. R. Sheng and E. Matunis, 2011 Development 138, 3367; Yadlapalli et al., 2011 J Cell Sci 124, 933; and S. Yadlapalli and Y. M. Yamashita, 2013 Nature), post-mitotic GSC-GB pairs derived from GSC asymmetric divisions were examined to assess patterns of histone inheritance (Tran et al., 2012 Science 338, 679, see also below). In contrast to the asymmetric pattern of wild-type H3 (FIG. 3A-FIG. 3C, open circles mainly in zone I and II in FIG. 3J), 86.8% (33/38) GSC-GB pairs showed symmetric distribution of H3T3A-GFP and H3T3A-mKO signals (FIG. 3D-FIG. 3F, solid triangles in zone III in FIG. 3J). Moreover, asymmetric distributions could be observed in two distinct patterns: wild-type asymmetry (left pair in FIG. 3G-FIG. 3I, solid triangles in zone I in FIG. 3J) and opposite asymmetry (right pair in FIG. 3G-FIG. 3I, solid triangles in zone IV in FIG. 3J). Since no asymmetric pattern should be observed if the incorporation of preexisting and newly synthesized H3 on sister chromatids is randomized (Step one; FIG. 5B), these data suggest that the establishment of asymmetric H3 prior to mitosis may not be affected. However, when cells enter mitosis, asymmetric H3 segregation (Step two; FIG. 5B) is mis-regulated, resulting in randomized patterns. Because male flies have two major autosomes and two sex chromosomes, all possible segregation patterns were calculated if only the second step in FIG. 5B is affected (FIG. 9B). According to this estimation, only when the two autosomes have the same segregation pattern was overall asymmetric H3 distribution (12.5%) observed; and for the rest, symmetric pattern should be observed (87.5%). This estimation is very close to the data presented herein: approximately 13.2% GSC-GB pairs showed asymmetric inheritance pattern (5/38 in zone I and IV in FIG. 3J) in nos>H3T3A testes. By contrast, 89.1% of GSC-GB pairs showed asymmetric inheritance pattern (49/55 in zone I and II in FIG. 3J) in wild-type H3-expressing testes. Noticeably, no GSC-GB pair showed the opposite asymmetric pattern (zone IV) in wild-type H3-expressing testes, but such an opposite asymmetry could be detected in H3T3A-expressing testes. Furthermore, the asymmetry for GFP is more obvious than that for mKO, most likely due to the fact that their fluorescence intensity was measured in post-mitotic GSC-GB pairs, when both cells are undergoing S phase with robust incorporation of mKO-labeled new histones. Therefore the difference of mKO signals in GSC and GB becomes less dramatic than that of GFP, consistent with what has been reported previously (Tran et al., 2012 Science 338, 679; Tran et al., 2013 Chromosome Res 21, 255).

Figure 4:
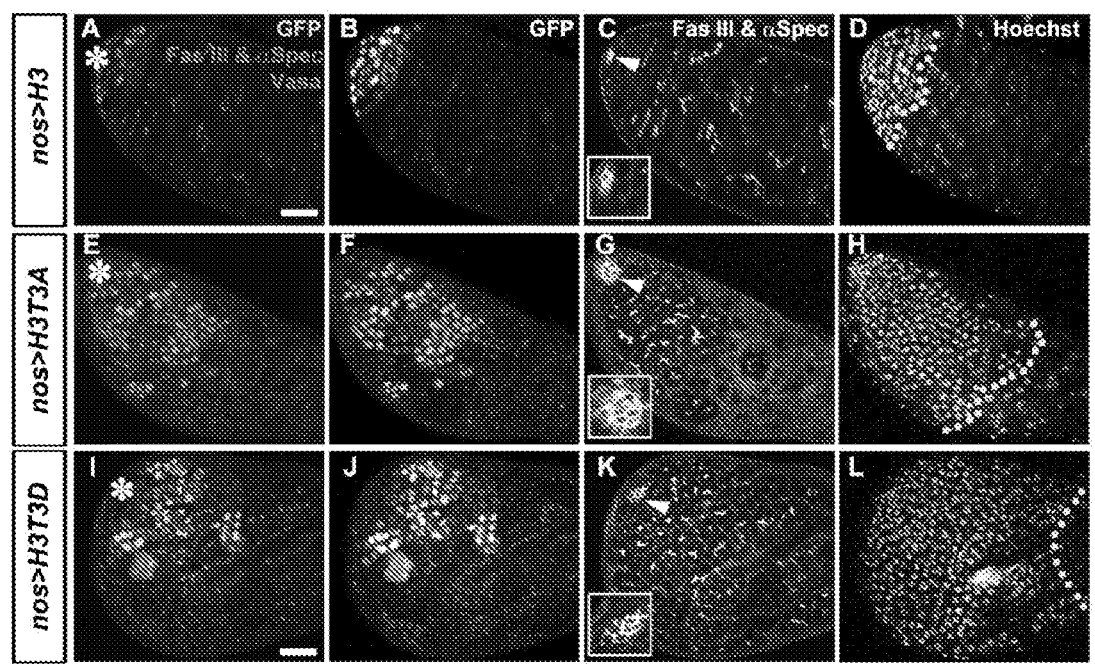
FIG. 4A-FIG. 4L is a series of photomicrographs showing expression of H3T3A and H3T3D causes similar defects. Shown are immunostaining signals using anti-FasIII and anti-α-Spectrin at the tip of nos>H3 (FIG. 4A-FIG. 4D), nos>H3T3A (FIG. 4E-FIG. 4H), or nos>H3T3D (FIG. 4I-FIG. 4L) testes. Scale bars: 20 µm.
Figure 10:
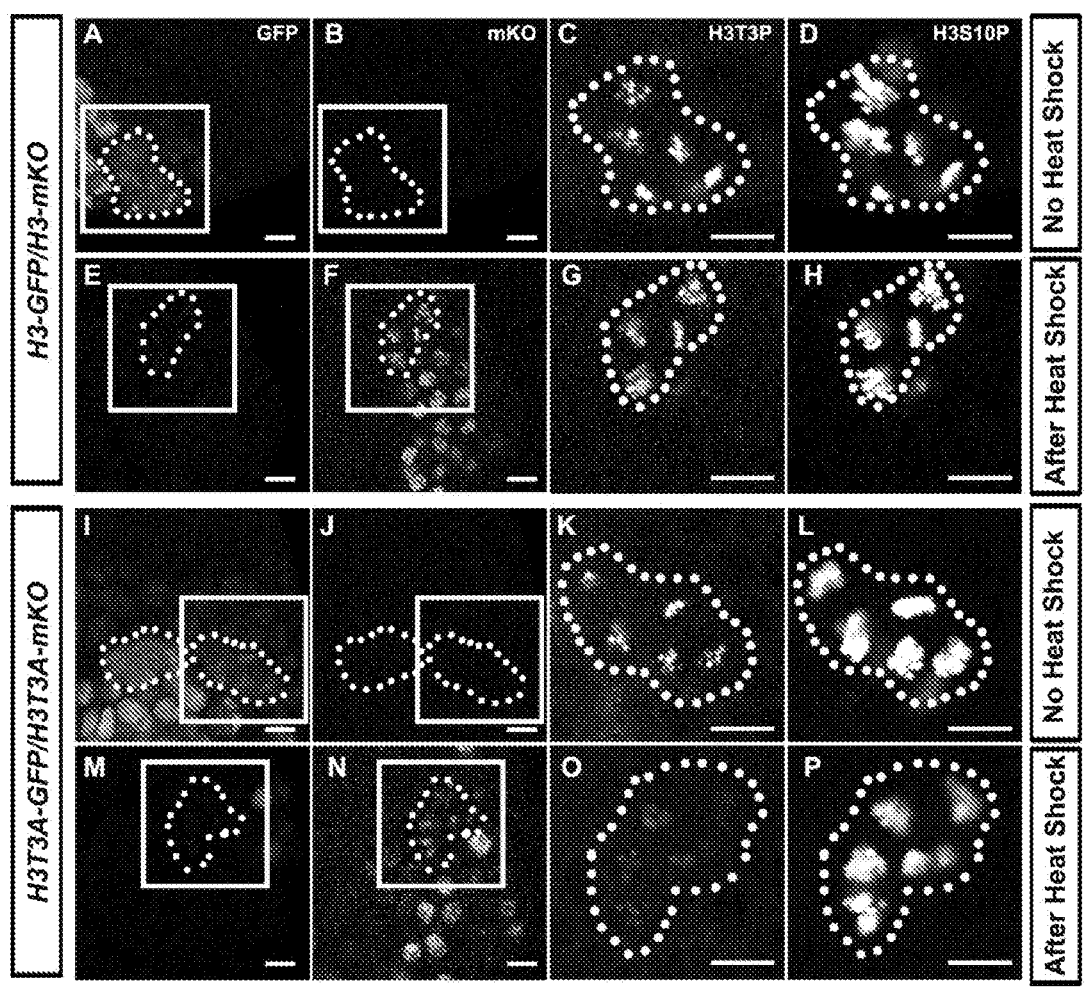
Figure 11:
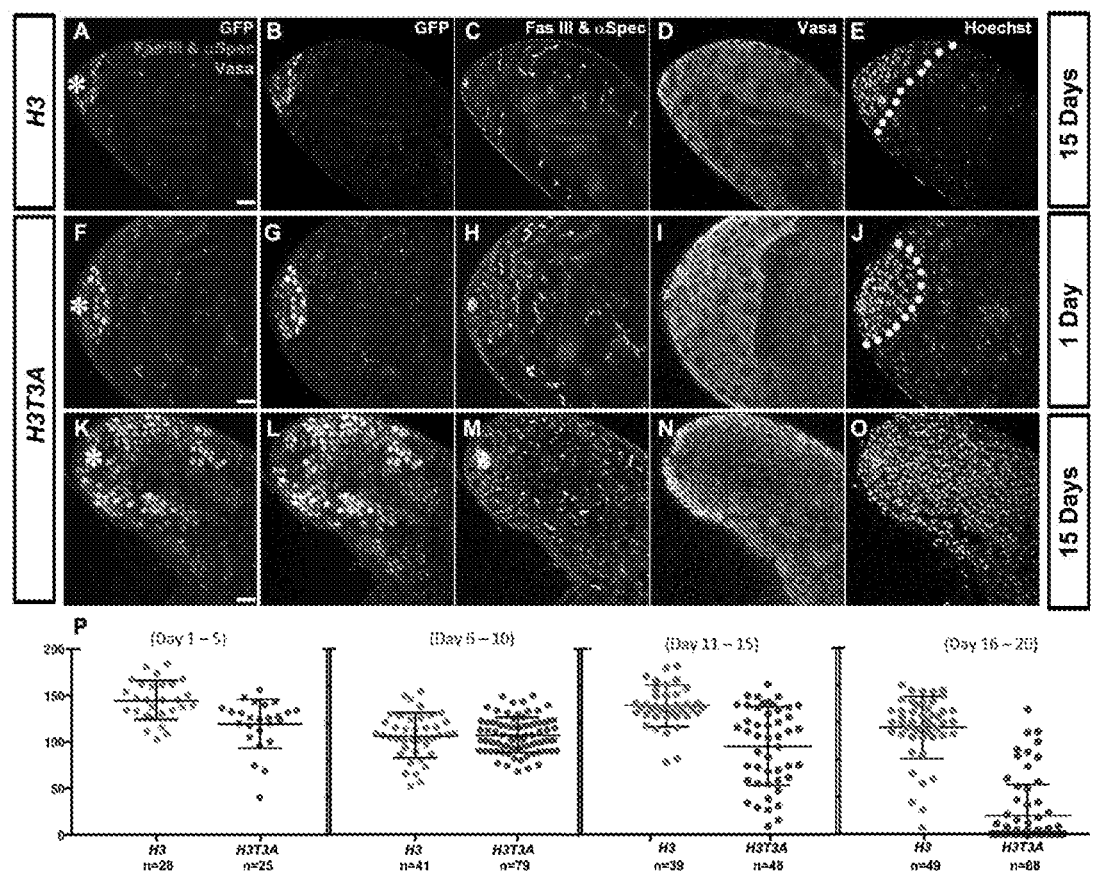
FIG. 11A-FIG. 11O is a series of photomicrographs showing that expression of the H3T3A transgene leads to gradual progression of germline tumor and decreased male fertility.
FIG. 11P shows the results of a fertility test using nos>H3-GFP (red dots) and nos>H3T3A-GFP (blue dots) males. Flies were raised at 18° C. until eclosion and crossed with y,w virgin females. All crosses were shifted to 29° C. and progenies were counted after the indicated time, for both immunostaining experiments and fertility tests. For Day 11-15 and Day 16-20 groups: $P<10^{-7}$ based on two-tailed t-test. Asterisk: hub. Scale bars: 20 μM.
Figure 12:
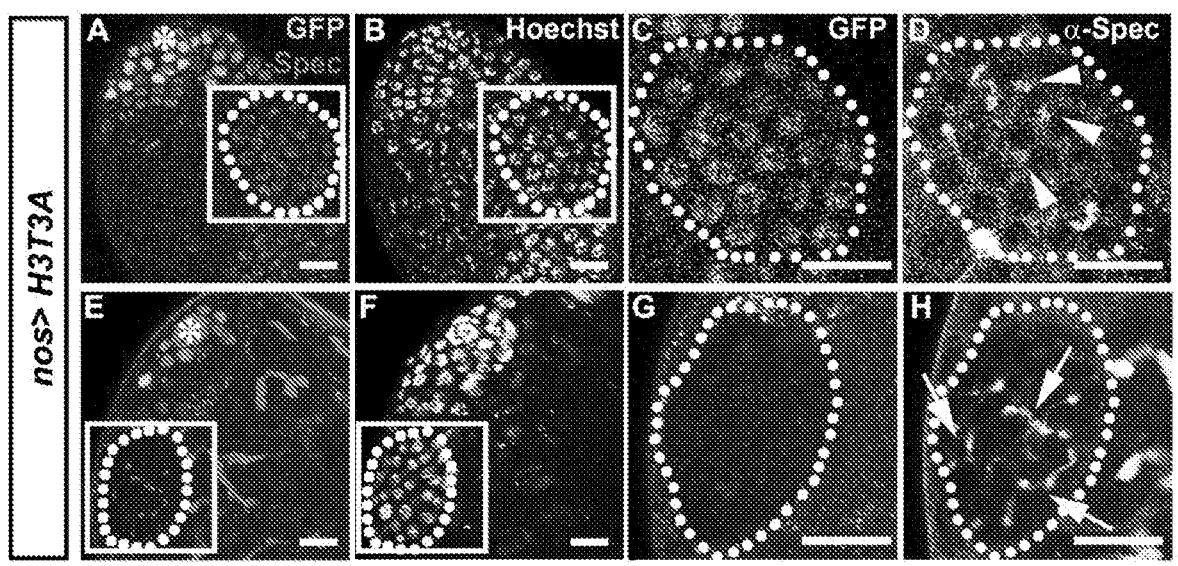
FIG. 12A-FIG. 12H is a series of photomicrographs showing the heterogeneous germline tumor in nos>H3T3A-GFP testes.
Figure 14:
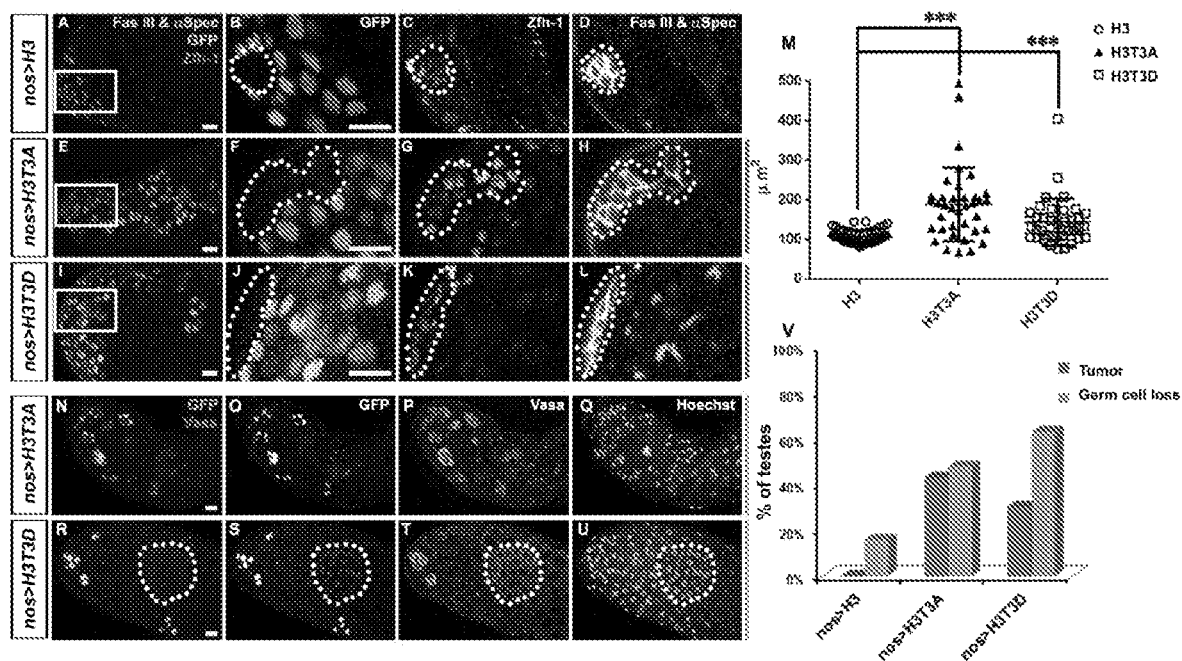
FIG. 14A-FIG. 14V is a series of photomicrographs, a dolt plot, and a bar chart showing that the expression of H3T3A or H3T3D using the nos-Gal4 driver leads to similar phenotypes in testis. Shown is immunostaining using antibodies against FasIII, α-Spectrin, Zfh-1, and Vasa in testes from nos>H3-GFP (FIG. 14A-FIG. 14D), nos>H3T3A-GFP (FIG. 14E-FIG. 14H, FIG. 14N-FIG. 14Q), and nos>H3T3D-GFP (FIG. 14I-FIG. 14L, FIG. 14R-FIG. 14U) males. Germline tumors develop (FIG. 14E, FIG. 14I, FIG. 14R-FIG. 14U), Vasa$^+$ germ cells are not maintained properly (FIG. 14N, FIG. 14P, FIG. 14R, FIG. 14T), hub size increases (FIG. 14E and FIG. 14I, insets in FIG. 14E and FIG. 14I are shown at higher magnification in FIG. 14F-FIG. 14H and FIG. 14J-FIG. 14L, respectively) and FasIII$^+$ hub cells co-express Zfh-1 (FIG. 14G, FIG. 14K) in testes from nos>H3T3A-GFP or nos>H3T3D-GFP males, but not in testes from nos>H3-GFP males. Scale bars: 20 μm.
FIG. 14M shows the quantification of hub size: 108±2.393 μm$^2$ in nos>H3-GFP (N=50) testes vs. 198.5±15.22 μm$^2$ in nos>H3T3A-GFP testes (N=37) (*P<0.0001) or 145.2±9.702 μm$^2$ in nos>H3T3D-GFP testes (N=37) (*P<0.0001). P-value calculated by unpaired t test.

Expression of H3T3A in early germ cells (nos>H3T3A) also caused a spectrum of cellular defects after H3T3P is effectively reduced (FIG. 10A-FIG. 10P). Compared to testes expressing the wild-type H3 (FIG. 4A-FIG. 4D; FIG. 11A-FIG. 11E), H3T3A-expressing testes exhibited an expansion of germ cells carrying early stage cellular markers. These markers include nanos-driven GFP expression (FIG. 4E-FIG. 4F; FIG. 11K-FIG. 11L), spectrosome structure (Lin et al., 1994 Development 120, 947; M. de Cuevas and A. C. Spradling, 1998 Development 125, 2781; Hime et al., 1996 J Cell Sci 109 (Pt 12), 2779) (FIG. 4E, FIG. 4G, FIG. 11K, and FIG. 11M) and condensed nuclei (Tran et al., 2000 Nature 407, 754; Chen et al., 2013 Cell Stem Cell 13, 73; Schulz et al., 2004 Genetics 167, 707) (FIG. 4H; FIG. 11O). Noticeably, based on these cellular markers, the germline tumors developed in nos>H3T3A testes were heterogeneous (FIG. 12A-FIG. 12H). RNA-seq was performed to characterize the molecular features of nos>H3T3A testes. Although individual nos>H3T3A testis samples had a high degree of variation in their transcriptomes (FIG. 13A-FIG. 13B), all samples share early stage germline signatures (FIG. 13C), such as lack of meiotic and terminal differentiation gene expression (FIG. 13D). Furthermore, genes in DNA repair pathway and Pol II transcriptional initiation were up-regulated in all nos>H3T3A testis samples (FIG. 13E), suggesting that they may have activated DNA repair activity and possibly aberrant transcription. These data are consistent with the germ cell loss and progenitor germline tumor phenotypes observed. Noticeably, the transcriptome signature of nos>H3T3A testes was not similar to either the GSC-like-cell-enriched nos>upd testis sample (Terry et al., 2006 Dev Biot 294, 246) or spermatogonia-enriched bam testis sample (Gan et al., 2010 Cell Res 20, 763) (FIG. 13A-FIG. 13C). This heterogeneity is likely due to the different H3 inheritance patterns by randomized segregation (FIG. 9B). However, using the entire testis with mixed cell types and stages may also contribute to this heterogeneity. The nos>H3T3A males also had progressively decreased fertility (FIG. 11P), consistent with deterioration of germline defects over time (FIG. 11F-FIG. 11J vs. FIG. 11K-FIG. 11O) and germ cell loss likely due to GSC loss (FIG. 14N, FIG. 14P, and FIG. 14V). Development of these germline defects in adult flies suggests that H3T3P is required for GSC maintenance and for proper differentiation of GB. Lastly, compared to the hub region in nos>H3 testes (inset in FIG. 4C), nos>H3T3A testes (inset in FIG. 4G) showed substantially enlarged hub area (FIG. 14H vs. FIG. 14D and FIG. 14M), most likely as a secondary defect due to GSC loss as reported previously (Tazuke et al., 2002 Development 129, 2529; Monk et al., 2010Cell Stem Cell 6, 348; P. Gonczy and S. DiNardo, 1996 Development 122, 2437; and Dinardo et al., 2011 Development 138, 1687). The expanded hub cells were not tightly associated with each other (FIG. 14H vs. FIG. 14D) and expressed an early cyst cell marker Zfh-1 (Issigonis et al., 2009 Science 326, 153; Eun et al., 2014 Science 343, 1513; and L. Leatherman and S. Dinardo, 2008 Cell Stem Cell 3, 44) (FIG. 14G), suggesting that the niche architecture and gene expression are abnormal.

These phenotypes in nos>H3T3A testes were specifically caused by expressing H3T3A in early-stage germ cells. Using a later-stage germline driver bam-Gal4 (C. Schulz et al., 2004 Genetics 167, 707; Eun et al., 2014 Science 343, 1513; and J. Cheng et al., 2008 Nature 456, 599) (FIG. 15A) to turn on the same H3T3A transgene specifically in 4-cell spermatogonia and later stage germ cells was sufficient to reduce the H3T3P in later-stage germ cells (FIG. 15B-FIG. 15I). However, bam>H3T3A did not lead to germline tumor or enlarged hub phenotypes (FIG. 15J-FIG. 15M). This stage-specificity suggests that normal H3T3P is required in very early-stage germ cells, such as GSC, GB and/or two-cell spermatogonia, to be responsible for the observed phenotypes.

Expression of another H3T3 mutant that converts T to the phosphor-mimic Aspartic acid (Asp or D) using the dual-color labeling system (FIG. 9A) also randomized inheritance pattern (FIG. 16A-FIG. 16H). Approximately 81.2% GSC-GB pairs showed symmetric inheritance pattern (26/31 in zone III in fig. S12I) and only 16.1% GSC-GB pairs showed the opposite asymmetric inheritance pattern (5/31 in zone IV in fig. S12I) in nos>H3T3D testes, consistent with the estimation of randomized patterns (FIG. 9B). The nos>H3T3D also resulted in similar germline tumor (FIG. 4I-FIG. 4L, FIG. 14I, FIG. 14R-FIG. 14U, FIG. 14V), hub enlargement (inset in FIG. 4K; FIG. 14L0 FIG. 14M), and ectopic Zfh-1 expression in hub cells (FIG. 14K), as observed in nos>H3T3A testes. Similar to the H3T3A, H3T3D-GFP driven by the bam-Gal4 driver did not lead to these phenotypes (FIG. 15N-FIG. 15Q). Since loss of H3T3P by H3T3A-expression and gain of H3T3P by H3T3D-expression in early stage germ cells resulted in similar histone inheritance and cellular defects, phosphorylation of H3T3 requires a tight temporal control.

The epigenetic 'writer' that generates the H3T3P mark has been characterized as the Haspin kinase (Dai et al., 2005

Figure 17:
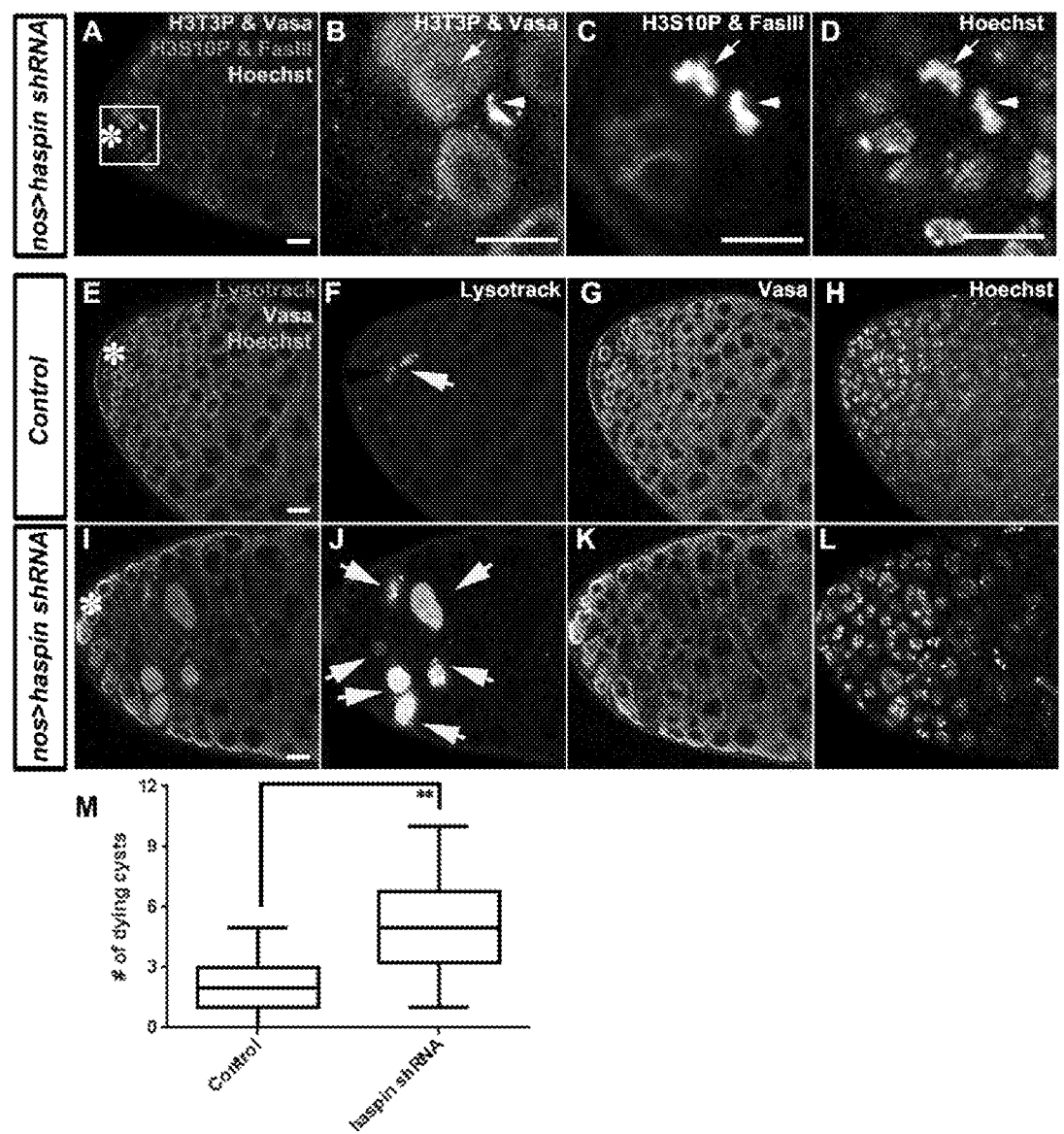
FIG. 17A-FIG. 17M is a series of photomicrographs and a bar chart showing that the knockdown of the H3T3P kinase Haspin in early stage germ cells leads to increased cell death.
Figure 18:
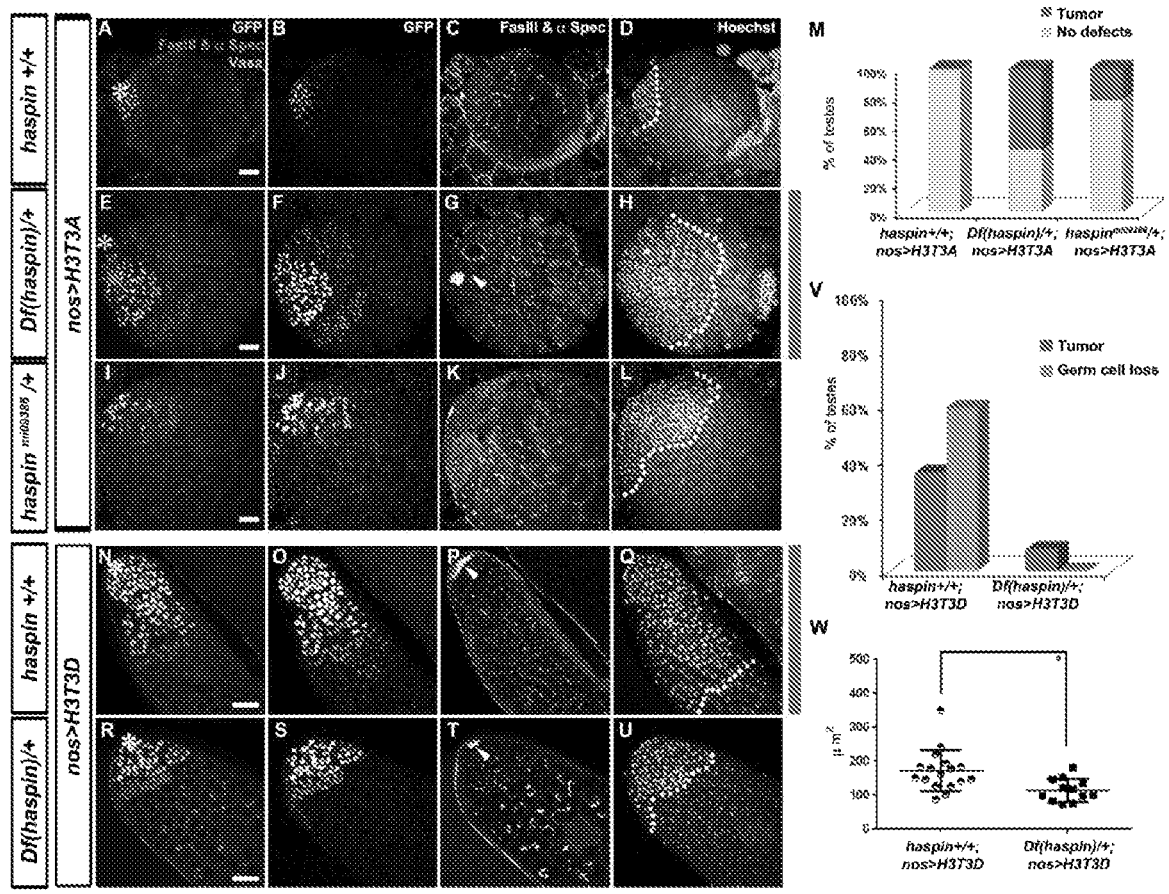
Figure 19:
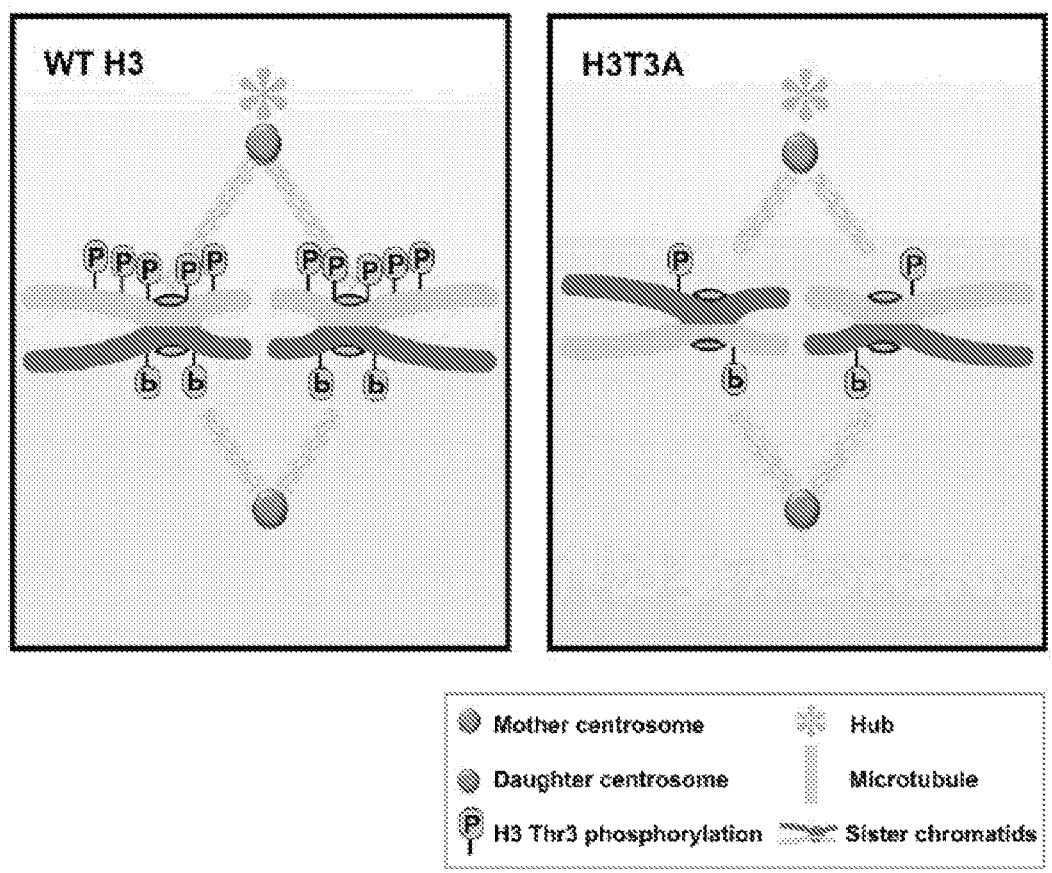
FIG. 19 is a diagram demonstrating prophase of *Drosophila* GSC. A transient mitosis-specific phosphate modification on histone H3 distinguishes pre-existing and newly synthesized histones and is required for the asymmetric segregation of sister chromatids—one enriched with new histones and the other with old histones—during stem cell division.
Figure 20:
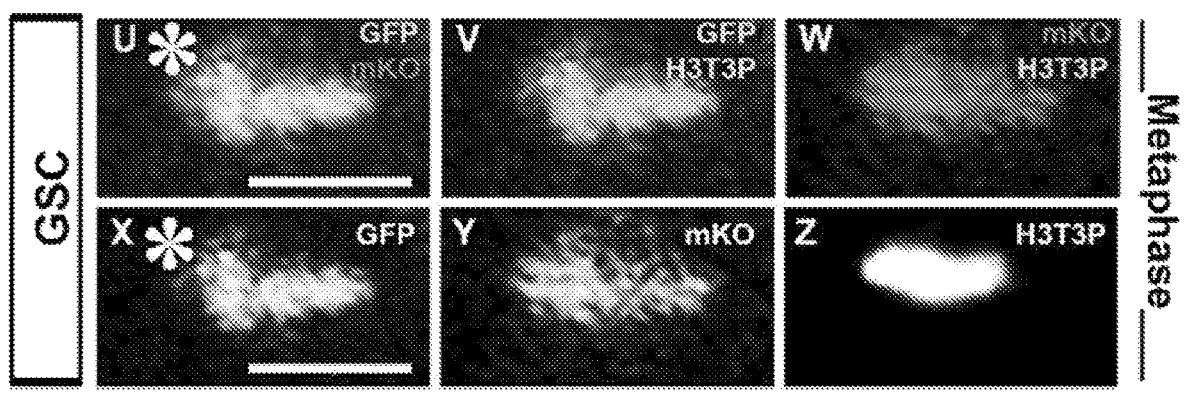
FIG. 20U-FIG. 20Z is a series of photographs demonstrating that H3T3P distinguishes pre-existing H3-GFP from newly synthesized H3-mKO in mitotic male GSCs. A metaphase GSC where GFP and mKO signals are indistinguishable (see FIG. 20U, FIG. 20X, and FIG. 20Y), H3T3P (FIG. 20Z) overlaps with both GFP (FIG. 20V and FIG. 20X) and mKO (FIG. 20W and FIG. 20Y). Asterisks in (FIG. 20U), and (FIG. 20X), hub. Scale bars, 5 μm.

Genes Dev 19, 472), loss-of-function phenotypes of the haspin gene were examined. When short hairpin RNA [shRNA, (Ni et al., 2011 Nat Methods 8, 405] was used to knock down haspin in early-stage germ cells using the nos-Gal4 driver, significant decrease of H3T3P in GSC was observed [arrow in FIG. 17B vs. a mitotic CySC (arrowhead)]. However, germ cell death in nos>haspin shRNA testes was much more substantial compared to nos>H3T3A or nos>H3T3D testes (FIG. 17I-FIG. 17J, and FIG. 17M), probably because Haspin has other substrate(s) required for cell survival. For example, the yeast Haspin homolog has potential substrates in the regulation of mitotic spindle polarity (Panigada et al., 2013 Dev Cell 26, 483), and a recent proteomic study revealed many chromatin proteins as potential substrates of Haspin in Hela cells (Panigada et al., 2013 Dev Cell 26, 483).

To explore how Haspin may function with H3T3A or H3T3D in early-stage germ cells, it was examined whether halving the level of Haspin could modify either nos>H3T3A or nos>H3T3D phenotypes. Using a deficiency chromosome that uncovers the haspin gene region, it was identified that it substantially enhanced the nos>H3T3A phenotype (compare FIG. 18E-FIG. 18H to FIG. 18A-FIG. 18D, and FIG. 18M) under a permissive condition for nos>H3T3A. Enhancement of the nos>H3T3A phenotype was also detected using a hypomorphic haspin$^{mi09386}$ allele (Venken et al., 2011 Nat Methods 8, 737), although at a lower penetrance and severity (FIG. 18I-FIG. 18M). By contrast, halving the level of Haspin suppressed the germ cell defects induced by nos>H3T3D (compare FIG. 18R-FIG. 18U to FIG. 18N-FIG. 18Q, and FIG. 18V-FIG. 18W), probably due to decreased phosphorylation on endogenous H3. These opposite genetic interactions further indicate that H3T3P needs to be tightly controlled for proper H3 inheritance and germline activity.

TABLE 1

Quantification of preexisting vs. newly synthesized H3, H3T3A and H3T3D in GSC-GB pairs for FIG. 3K and FIG. 16I.

| | H3 | | | H3T3A | | | H3T3D | |
|---|---|---|---|---|---|---|---|---|
| Pair # | GFP: GSC/GB | mKO: GB/GSC | Pair # | GFP: GSC/GB | mKO: GB/GSC | Pair # | GFP: GSC/GB | mKO: GB/GSC |
| 1 | 2.70 | 1.22 | 1 | 9.33 | 3.37 | 1 | 1.29 | 0.83 |
| 2 | 3.39 | 1.11 | 2 | 0.83 | 1.40 | 2 | 0.88 | 0.72 |
| 3 | 2.54 | 0.84 | 3 | 1.10 | 0.75 | 3 | 0.88 | 1.22 |
| 4 | 1.31 | 1.07 | 4 | 0.94 | 1.40 | 4 | 0.80 | 1.41 |
| 5 | 2.45 | 1.76 | 5 | 0.85 | 1.12 | 5 | 1.24 | 0.80 |
| 6 | 1.71 | 1.64 | 6 | 0.99 | 0.91 | 6 | 0.90 | 1.23 |
| 7 | 1.60 | 7.38 | 7 | 0.90 | 1.38 | 7 | 0.79 | 0.84 |
| 8 | 1.30 | 0.97 | 8 | 0.82 | 1.57 | 8 | 0.92 | 1.21 |
| 9 | 1.40 | 1.09 | 9 | 1.40 | 1.96 | 9 | 0.92 | 1.29 |
| 10 | 3.99 | 1.40 | 10 | 0.76 | 1.46 | 10 | 0.93 | 1.04 |
| 11 | 1.41 | 1.03 | 11 | 1.00 | 1.15 | 11 | 1.10 | 1.10 |
| 12 | 1.79 | 0.82 | 12 | 1.25 | 0.78 | 12 | 0.88 | 1.23 |
| 13 | 1.18 | 1.78 | 13 | 0.86 | 1.17 | 13 | 0.67 | 1.38 |
| 14 | 2.15 | 1.37 | 14 | 0.88 | 1.32 | 14 | 0.55 | 1.16 |
| 15 | 9.26 | 1.27 | 15 | 0.69 | 2.56 | 15 | 0.08 | 0.83 |
| 16 | 5.96 | 1.11 | 16 | 0.99 | 0.97 | 16 | 0.06 | 0.84 |
| 17 | 7.79 | 1.38 | 17 | 0.69 | 1.29 | 17 | 1.08 | 1.01 |
| 18 | 16.38 | 0.93 | 18 | 0.88 | 1.11 | 18 | 0.78 | 1.70 |
| 19 | 3.46 | 2.48 | 19 | 0.58 | 2.85 | 19 | 0.91 | 1.03 |
| 20 | 2.94 | 1.04 | 20 | 0.94 | 1.25 | 20 | 0.86 | 0.69 |
| 21 | 2.02 | 1.00 | 21 | 1.10 | 0.85 | 21 | 0.81 | 0.95 |
| 22 | 4.32 | 0.99 | 22 | 0.92 | 1.09 | 22 | 0.93 | 1.03 |
| 23 | 1.68 | 1.49 | 23 | 0.93 | 1.18 | 23 | 0.96 | 1.14 |
| 24 | 4.58 | 3.09 | 24 | 1.48 | 0.62 | 24 | 0.80 | 0.96 |
| 25 | 11.89 | 1.39 | 25 | 0.75 | 1.49 | 25 | 0.56 | 1.37 |
| 26 | 26.19 | 1.01 | 26 | 0.91 | 1.00 | 26 | 0.96 | 1.04 |
| 27 | 15.88 | 1.45 | 27 | 0.91 | 0.88 | 27 | 0.94 | 0.93 |
| 28 | 27.46 | 1.29 | 28 | 0.65 | 1.42 | 28 | 0.77 | 1.02 |
| 29 | 1.00 | 0.99 | 29 | 0.82 | 1.34 | 29 | 0.95 | 0.95 |
| 30 | 9.74 | 1.51 | 30 | 0.74 | 1.41 | 30 | 0.63 | 1.35 |
| 31 | 5.36 | 0.68 | 31 | 0.94 | 1.13 | 31 | 0.89 | 1.33 |
| 32 | 4.74 | 0.90 | 32 | 0.80 | 1.32 | | | |
| 33 | 2.46 | 9.35 | 33 | 0.58 | 1.69 | | | |
| 34 | 1.56 | 1.62 | 34 | 1.08 | 1.02 | | | |
| 35 | 21.84 | 1.41 | 35 | 0.71 | 1.48 | | | |
| 36 | 9.93 | 1.02 | 36 | 1.35 | 0.55 | | | |
| 37 | 10.00 | 1.54 | 37 | 0.56 | 1.29 | | | |
| 38 | 36.56 | 2.86 | 38 | 0.07 | 0.23 | | | |
| 39 | 43.31 | 1.71 | | | | | | |
| 40 | 4.94 | 1.21 | | | | | | |
| 41 | 4.55 | 1.17 | | | | | | |
| 42 | 20.48 | 1.02 | | | | | | |
| 43 | 18.73 | 0.69 | | | | | | |
| 44 | 66.01 | 1.02 | | | | | | |
| 45 | 21.52 | 1.84 | | | | | | |
| 46 | 18.16 | 2.44 | | | | | | |
| 47 | 28.33 | 1.37 | | | | | | |
| 48 | 6.82 | 1.39 | | | | | | |
| 49 | 10.44 | 1.39 | | | | | | |
| 50 | 10.44 | 1.39 | | | | | | |
| 51 | 1.05 | 2.10 | | | | | | |
| 52 | 2.60 | 1.34 | | | | | | |
| 53 | 1.82 | 1.01 | | | | | | |
| 54 | 14.30 | 0.92 | | | | | | |
| 55 | 10.70 | 1.30 | | | | | | |

TABLE 2A

100% Asymmetric Deposition

| | | X | Y | II | III | | >1.5 |
|---|---|---|---|---|---|---|---|
| | | | | Mbps | | | <0.66 |
| | | 22 | 40 | 44 | 52 | Sum: GFP | GFP: GSC/GB |
| 1 | GSC | 22 | 40 | 88 | 104 | 254 | NA |
| | GB | 22 | 40 | 88 | 104 | 0 | |
| 2 | GSC | 22 | 40 | 88 | 104 | 214 | 5.35 |
| | GB | 22 | 40 | 88 | 104 | 40 | |
| 3 | GSC | 22 | 40 | 88 | 104 | 232 | 10.55 |
| | GB | 22 | 40 | 88 | 104 | 22 | |
| 4 | GSC | 22 | 40 | 88 | 104 | 192 | 3.10 |
| | GB | 22 | 40 | 88 | 104 | 62 | |
| 5 | GSC | 22 | 40 | 88 | 104 | 166 | 1.89 |
| | GB | 22 | 40 | 88 | 104 | 88 | |
| 6 | GSC | 22 | 40 | 88 | 104 | 126 | 0.98 |
| | GB | 22 | 40 | 88 | 104 | 128 | |
| 7 | GSC | 22 | 40 | 88 | 104 | 144 | 1.31 |
| | GB | 22 | 40 | 88 | 104 | 110 | |
| 8 | GSC | 22 | 40 | 88 | 104 | 104 | 0.69 |
| | GB | 22 | 40 | 88 | 104 | 150 | |
| 9 | GSC | 22 | 40 | 88 | 104 | 150 | 1.44 |
| | GB | 22 | 40 | 88 | 104 | 104 | |
| 10 | GSC | 22 | 40 | 88 | 104 | 110 | 0.76 |
| | GB | 22 | 40 | 88 | 104 | 144 | |
| 11 | GSC | 22 | 40 | 88 | 104 | 128 | 1.02 |
| | GB | 22 | 40 | 88 | 104 | 126 | |
| 12 | GSC | 22 | 40 | 88 | 104 | 88 | 0.53 |
| | GB | 22 | 40 | 88 | 104 | 166 | |
| 13 | GSC | 22 | 40 | 88 | 104 | 62 | 0.32 |
| | GB | 22 | 40 | 88 | 104 | 192 | |
| 14 | GSC | 22 | 40 | 88 | 104 | 22 | 0.09 |
| | GB | 22 | 40 | 88 | 104 | 232 | |
| 15 | GSC | 22 | 40 | 88 | 104 | 40 | 0.19 |

TABLE 2A-continued

100% Asymmetric Deposition

| | | X | Y | II | III | | >1.5 |
|---|---|---|---|---|---|---|---|
| | | | | Mbps | | | <0.66 |
| | | 22 | 40 | 44 | 52 | Sum: GFP | GFP: GSC/GB |
| | GB | 22 | 40 | 88 | 104 | 214 | |
| 16 | GSC | 22 | 40 | 88 | 104 | 0 | NA |
| | GB | 22 | 40 | 88 | 104 | 254 | |
| 17 | GSC | 22 | 40 | 44/44 | 104 | 210 | 4.77 |
| | GB | 22 | 40 | 44/44 | 104 | 44 | |
| 18 | GSC | 22 | 40 | 44/44 | 104 | 170 | 2.02 |
| | GB | 22 | 40 | 44/44 | 104 | 84 | |
| 19 | GSC | 22 | 40 | 44/44 | 104 | 188 | 2.85 |
| | GB | 22 | 40 | 44/44 | 104 | 66 | |
| 20 | GSC | 22 | 40 | 44/44 | 104 | 148 | 1.40 |
| | GB | 22 | 40 | 44/44 | 104 | 106 | |
| 21 | GSC | 22 | 40 | 44/44 | 104 | 106 | 0.72 |
| | GB | 22 | 40 | 44/44 | 104 | 148 | |
| 22 | GSC | 22 | 40 | 44/44 | 104 | 66 | 0.35 |
| | GB | 22 | 40 | 44/44 | 104 | 188 | |
| 23 | GSC | 22 | 40 | 44/44 | 104 | 84 | 0.49 |
| | GB | 22 | 40 | 44/44 | 104 | 170 | |
| 24 | GSC | 22 | 40 | 44/44 | 104 | 44 | 0.21 |
| | GB | 22 | 40 | 44/44 | 104 | 210 | |
| 25 | GSC | 22 | 40 | 44/44 | 104 | 210 | 4.77 |
| | GB | 22 | 40 | 44/44 | 104 | 44 | |
| 26 | GSC | 22 | 40 | 44/44 | 104 | 170 | 2.02 |
| | GB | 22 | 40 | 44/44 | 104 | 84 | |
| 27 | GSC | 22 | 40 | 44/44 | 104 | 188 | 2.85 |
| | GB | 22 | 40 | 44/44 | 104 | 66 | |
| 28 | GSC | 22 | 40 | 44/44 | 104 | 148 | 1.40 |
| | GB | 22 | 40 | 44/44 | 104 | 106 | |
| 29 | GSC | 22 | 40 | 44/44 | 104 | 106 | 0.72 |
| | GB | 22 | 40 | 44/44 | 104 | 148 | |
| 30 | GSC | 22 | 40 | 44/44 | 104 | 66 | 0.35 |
| | GB | 22 | 40 | 44/44 | 104 | 188 | |
| 31 | GSC | 22 | 40 | 44/44 | 104 | 84 | 0.49 |
| | GB | 22 | 40 | 44/44 | 104 | 170 | |
| 32 | GSC | 22 | 40 | 44/44 | 104 | 44 | 0.21 |
| | GB | 22 | 40 | 44/44 | 104 | 210 | |
| 33 | GSC | 22 | 40 | 88 | 52/52 | 202 | 3.88 |
| | GB | 22 | 40 | 88 | 52/52 | 52 | |
| 34 | GSC | 22 | 40 | 88 | 52/52 | 162 | 1.76 |
| | GB | 22 | 40 | 88 | 52/52 | 92 | |
| 35 | GSC | 22 | 40 | 88 | 52/52 | 180 | 2.43 |
| | GB | 22 | 40 | 88 | 52/52 | 74 | |
| 36 | GSC | 22 | 40 | 88 | 52/52 | 140 | 1.23 |
| | GB | 22 | 40 | 88 | 52/52 | 114 | |
| 37 | GSC | 22 | 40 | 88 | 52/52 | 114 | 0.81 |
| | GB | 22 | 40 | 88 | 52/52 | 140 | |
| 38 | GSC | 22 | 40 | 88 | 52/52 | 74 | 0.41 |
| | GB | 22 | 40 | 88 | 52/52 | 180 | |
| 39 | GSC | 22 | 40 | 88 | 52/52 | 92 | 0.57 |
| | GB | 22 | 40 | 88 | 52/52 | 162 | |
| 40 | GSC | 22 | 40 | 88 | 52/52 | 52 | 0.26 |
| | GB | 22 | 40 | 88 | 52/52 | 202 | |
| 41 | GSC | 22 | 40 | 88 | 52/52 | 202 | 3.88 |
| | GB | 22 | 40 | 88 | 52/52 | 52 | |
| 42 | GSC | 22 | 40 | 88 | 52/52 | 162 | 1.76 |
| | GB | 22 | 40 | 88 | 52/52 | 92 | |
| 43 | GSC | 22 | 40 | 88 | 52/52 | 180 | 2.43 |
| | GB | 22 | 40 | 88 | 52/52 | 74 | |
| 44 | GSC | 22 | 40 | 88 | 52/52 | 140 | 1.23 |
| | GB | 22 | 40 | 88 | 52/52 | 114 | |
| 45 | GSC | 22 | 40 | 88 | 52/52 | 114 | 0.81 |
| | GB | 22 | 40 | 88 | 52/52 | 140 | |
| 46 | GSC | 22 | 40 | 88 | 52/52 | 74 | 0.41 |
| | GB | 22 | 40 | 88 | 52/52 | 180 | |
| 47 | GSC | 22 | 40 | 88 | 52/52 | 94 | 0.59 |
| | GB | 22 | 40 | 88 | 52/52 | 160 | |
| 48 | GSC | 22 | 40 | 88 | 52/52 | 52 | 0.26 |
| | GB | 22 | 40 | 88 | 52/52 | 202 | |
| 49 | GSC | 22 | 40 | 44/44 | 52/52 | 158 | 1.65 |
| | GB | 22 | 40 | 44/44 | 52/52 | 96 | |
| 50 | GSC | 22 | 40 | 44/44 | 52/52 | 118 | 0.87 |
| | GB | 22 | 40 | 44/44 | 52/52 | 136 | |
| 51 | GSC | 22 | 40 | 44/44 | 52/52 | 136 | 1.15 |
| | GB | 22 | 40 | 44/44 | 52/52 | 118 | |
| 52 | GSC | 22 | 40 | 44/44 | 52/52 | 96 | 0.61 |
| | GB | 22 | 40 | 44/44 | 52/52 | 158 | |
| 53 | GSC | 22 | 40 | 44/44 | 52/52 | 158 | 1.65 |
| | GB | 22 | 40 | 44/44 | 52/52 | 96 | |
| 54 | GSC | 22 | 40 | 44/44 | 52/52 | 118 | 0.87 |
| | GB | 22 | 40 | 44/44 | 52/52 | 136 | |
| 55 | GSC | 22 | 40 | 44/44 | 52/52 | 136 | 1.15 |
| | GB | 22 | 40 | 44/44 | 52/52 | 118 | |
| 56 | GSC | 22 | 40 | 44/44 | 52/52 | 96 | 0.61 |
| | GB | 22 | 40 | 44/44 | 52/52 | 158 | |
| 57 | GSC | 22 | 40 | 44/44 | 52/52 | 158 | 1.65 |
| | GB | 22 | 40 | 44/44 | 52/52 | 96 | |
| 58 | GSC | 22 | 40 | 44/44 | 52/52 | 118 | 0.87 |
| | GB | 22 | 40 | 44/44 | 52/52 | 136 | |
| 59 | GSC | 22 | 40 | 44/44 | 52/52 | 136 | 1.15 |
| | GB | 22 | 40 | 44/44 | 52/52 | 118 | |
| 60 | GSC | 22 | 40 | 44/44 | 52/52 | 96 | 0.61 |
| | GB | 22 | 40 | 44/44 | 52/52 | 158 | |
| 61 | GSC | 22 | 40 | 44/44 | 52/52 | 158 | 1.65 |
| | GB | 22 | 40 | 44/44 | 52/52 | 96 | |
| 62 | GSC | 22 | 40 | 44/44 | 52/52 | 118 | 0.87 |
| | GB | 22 | 40 | 44/44 | 52/52 | 136 | |
| 63 | GSC | 22 | 40 | 44/44 | 52/52 | 136 | 1.15 |
| | GB | 22 | 40 | 44/44 | 52/52 | 118 | |
| 64 | GSC | 22 | 40 | 44/44 | 52/52 | 96 | 0.61 |
| | GB | 22 | 40 | 44/44 | 52/52 | 158 | |

| Cut-off | Asymmetry | Symmetry | Asymmetry (opposite) |
|---|---|---|---|
| 1.5 | 21 (32.8%) | 22 (34.4%) | 21 (32.8%) |
| 2 | 14 (21.9%) | 36 (56.2%) | 14 (21.9%) |
| 2.5 | 10 (15.6%) | 44 (68.8) | 10 (15.6%) |
| 3 | 8 (12.5%) | 48 (75%) | 8 (12.5%) |

TABLE 2B

80% Asymmetric Deposition
80% asymmetric deposition

| | | | X | Y | II | III | | X | Y | II | III | | GFP: |
|---|---|---|---|---|---|---|---|---|---|---|---|---|---|
| | | | | | Mbps | | | | | Mbps | | | |
| | | | 22 | 40 | 44 | 52 | | 22 | 40 | 44 | 52 | Sum: GFP | GSC/GB |
| 1 | GSC | 80% GSC | 17.6 | 32 | 70.4 | 83.2 | 20% GSC | 4.4 | 8 | 17.6 | 20.8 | 203.2 | 4.00 |
| | GB | 80% GB | 17.6 | 32 | 70.4 | 83.2 | 20% GB | 4.4 | 8 | 17.6 | 20.8 | 50.8 | |

TABLE 2B-continued

| | | 80% Asymmetric Deposition | | | | | | | | | | |
|---|---|---|---|---|---|---|---|---|---|---|---|---|
| | | 80% asymmetric deposition | | | | | | | | | | |
| | | | X | Y | II Mbps | III | | X | Y | II Mbps | III | GFP: |
| | | | 22 | 40 | 44 | 52 | | 22 | 40 | 44 | 52 | Sum: GFP | GSC/GB |

| | | | X | Y | II | III | | X | Y | II | III | Sum: GFP | GSC/GB |
|---|---|---|---|---|---|---|---|---|---|---|---|---|---|
| 2 | GSC | 80% GSC | 17.6 | 32 | 70.4 | 83.2 | 20% GSC | 4.4 | 8 | 17.6 | 20.8 | 179.2 | 2.40 |
| | GB | 80% GB | 17.6 | 32 | 70.4 | 83.2 | 20% GB | 4.4 | 8 | 17.6 | 20.8 | 74.8 | |
| 3 | GS | 80% GSC | 17.6 | 32 | 70.4 | 83.2 | 20% GSC | 4.4 | 8 | 17.6 | 20.8 | 190 | 2.97 |
| | GB | 80% GB | 17.6 | 32 | 70.4 | 83.2 | 20% GB | 4.4 | 8 | 17.6 | 20.8 | 64 | |
| 4 | GSC | 80% GSC | 17.6 | 32 | 70.4 | 83.2 | 20% GSC | 4.4 | 8 | 17.6 | 20.8 | 166 | 1.89 |
| | GB | 80% GB | 17.6 | 32 | 70.4 | 83.2 | 20% GB | 4.4 | 8 | 17.6 | 20.8 | 88 | |
| 5 | GSC | 80% GSC | 17.6 | 32 | 70.4 | 83.2 | 20% GSC | 4.4 | 8 | 17.6 | 20.8 | 150.4 | 1.45 |
| | GB | 80% GB | 17.6 | 32 | 70.4 | 83.2 | 20% GB | 4.4 | 8 | 17.6 | 20.8 | 103.6 | |
| 6 | GSC | 80% GSC | 17.6 | 32 | 70.4 | 83.2 | 20% GSC | 4.4 | 8 | 17.6 | 20.8 | 126.4 | 0.99 |
| | GB | 80% GB | 17.6 | 32 | 70.4 | 83.2 | 20% GB | 4.4 | 8 | 17.6 | 20.8 | 127.6 | |
| 7 | GSC | 80% GSC | 17.6 | 32 | 70.4 | 83.2 | 20% GSC | 4.4 | 8 | 17.6 | 20.8 | 137.2 | 1.17 |
| | GB | 80% GB | 17.6 | 32 | 70.4 | 83.2 | 20% GB | 4.4 | 8 | 17.6 | 20.8 | 116.8 | |
| 8 | GSC | 80% GSC | 17.6 | 32 | 70.4 | 83.2 | 20% GSC | 4.4 | 8 | 17.6 | 20.8 | 113.2 | 0.80 |
| | GB | 80% GB | 17.6 | 32 | 70.4 | 83.2 | 20% GB | 4.4 | 8 | 17.6 | 20.8 | 140.8 | |
| 9 | GSC | 80% GSC | 17.6 | 32 | 70.4 | 83.2 | 20% GSC | 4.4 | 8 | 17.6 | 20.8 | 140.8 | 1.24 |
| | GB | 80% GB | 17.6 | 32 | 70.4 | 83.2 | 20% GB | 4.4 | 8 | 17.6 | 20.8 | 113.2 | |
| 10 | GSC | 80% GSC | 17.6 | 32 | 70.4 | 83.2 | 20% GSC | 4.4 | 8 | 17.6 | 20.8 | 116.8 | 0.85 |
| | GB | 80% GB | 17.6 | 32 | 70.4 | 83.2 | 20% GB | 4.4 | 8 | 17.6 | 20.8 | 137.2 | |
| 11 | GSC | 80% GSC | 17.6 | 32 | 70.4 | 83.2 | 20% GSC | 4.4 | 8 | 17.6 | 20.8 | 127.6 | 1.01 |
| | GB | 80% GB | 17.6 | 32 | 70.4 | 83.2 | 20% GB | 4.4 | 8 | 17.6 | 20.8 | 126.4 | |
| 12 | GSC | 80% GSC | 17.6 | 32 | 70.4 | 83.2 | 20% GSC | 4.4 | 8 | 17.6 | 20.8 | 103.6 | 0.69 |
| | GB | 80% GB | 17.6 | 32 | 70.4 | 83.2 | 20% GB | 4.4 | 8 | 17.6 | 20.8 | 150.4 | |
| 13 | GSC | 80% GSC | 17.6 | 32 | 70.4 | 83.2 | 20% GSC | 4.4 | 8 | 17.6 | 20.8 | 88 | 0.53 |
| | GB | 80% GB | 17.6 | 32 | 70.4 | 83.2 | 20% GB | 4.4 | 8 | 17.6 | 20.8 | 166 | |
| 14 | GSC | 80% GSC | 17.6 | 32 | 70.4 | 83.2 | 20% GSC | 4.4 | 8 | 17.6 | 20.8 | 64 | 0.34 |
| | GB | 80% GB | 17.6 | 32 | 70.4 | 83.2 | 20% GB | 4.4 | 8 | 17.6 | 20.8 | 190 | |
| 15 | GSC | 80% GSC | 17.6 | 32 | 70.4 | 83.2 | 20% GSC | 4.4 | 8 | 17.6 | 20.8 | 74.8 | 0.42 |
| | GB | 80% GB | 17.6 | 32 | 70.4 | 83.2 | 20% GB | 4.4 | 8 | 17.6 | 20.8 | 179.2 | |
| 16 | GSC | 80% GSC | 17.6 | 32 | 70.4 | 83.2 | 20% GSC | 4.4 | 8 | 17.6 | 20.8 | 50.8 | 0.25 |
| | GB | 80% GB | 17.6 | 32 | 70.4 | 83.2 | 20% GB | 4.4 | 8 | 17.6 | 20.8 | 203.2 | |
| 17 | GSC | 80% GSC | 17.6 | 32 | 35.2/35.2 | 83.2 | 20% GSC | 4.4 | 8 | 8.8/8.8 | 20.8 | 176.8 | 2.29 |
| | GB | 80% GB | 17.6 | 32 | 35.2/35.2 | 83.2 | 20% GB | 4.4 | 8 | 8.8/8.8 | 20.8 | 77.2 | |
| 18 | GSC | 80% GSC | 17.6 | 32 | 35.2/35.2 | 83.2 | 20% GSC | 4.4 | 8 | 8.8/8.8 | 20.8 | 152.8 | 1.51 |
| | GB | 80% GB | 17.6 | 32 | 35.2/35.2 | 83.2 | 20% GB | 4.4 | 8 | 8.8/8.8 | 20.8 | 101.2 | |
| 19 | GSC | 80% GSC | 17.6 | 32 | 35.2/35.2 | 83.2 | 20% GSC | 4.4 | 8 | 8.8/8.8 | 20.8 | 163.6 | 1.81 |
| | GB | 80% GB | 17.6 | 32 | 35.2/35.2 | 83.2 | 20% GB | 4.4 | 8 | 8.8/8.8 | 20.8 | 90.4 | |

TABLE 2B-continued

| | | | \multicolumn{4}{c|}{80% Asymmetric Deposition} | \multicolumn{4}{c|}{80% asymmetric deposition} | | |
|---|---|---|---|---|---|---|---|---|---|---|---|---|
| | | | X | Y | II Mbps | III | X | Y | II Mbps | III | | GFP: |
| | | | 22 | 40 | 44 | 52 | 22 | 40 | 44 | 52 | Sum: GFP | GSC/GB |
| 20 | GSC | 80% GSC | 17.6 | 32 | 35.2/35.2 | 83.2 | 20% GSC | 4.4 | 8 | 8.8/8.8 | 20.8 | 139.6 | 1.22 |
| | GB | 80% GB | 17.6 | 32 | 35.2/35.2 | 83.2 | 20% GB | 4.4 | 8 | 8.8/8.8 | 20.8 | 114.4 | |
| 21 | GSC | 80% GSC | 17.6 | 32 | 35.2/35.2 | 83.2 | 20% GSC | 4.4 | 8 | 8.8/8.8 | 20.8 | 114.4 | 0.82 |
| | GB | 80% GB | 17.6 | 32 | 35.2/35.2 | 83.2 | 20% GB | 4.4 | 8 | 8.8/8.8 | 20.8 | 139.6 | |
| 22 | GSC | 80% GSC | 17.6 | 32 | 35.2/35.2 | 83.2 | 20% GSC | 4.4 | 8 | 8.8/8.8 | 20.8 | 90.4 | 0.55 |
| | GB | 80% GB | 17.6 | 32 | 35.2/35.2 | 83.2 | 20% GB | 4.4 | 8 | 8.8/8.8 | 20.8 | 163.6 | |
| 23 | GSC | 80% GSC | 17.6 | 32 | 35.2/35.2 | 83.2 | 20% GSC | 4.4 | 8 | 8.8/8.8 | 20.8 | 101.2 | 0.66 |
| | GB | 80% GB | 17.6 | 32 | 35.2/35.2 | 83.2 | 20% GB | 4.4 | 8 | 8.8/8.8 | 20.8 | 152.8 | |
| 24 | GSC | 80% GSC | 17.6 | 32 | 35.2/35.2 | 83.2 | 20% GSC | 4.4 | 8 | 8.8/8.8 | 20.8 | 77.2 | 0.44 |
| | GB | 80% GB | 17.6 | 32 | 35.2/35.2 | 83.2 | 20% GB | 4.4 | 8 | 8.8/8.8 | 20.8 | 176.8 | |
| 25 | GSC | 80% GSC | 17.6 | 32 | 35.2/35.2 | 83.2 | 20% GSC | 4.4 | 8 | 8.8/8.8 | 20.8 | 176.8 | 2.29 |
| | GB | 80% GB | 17.6 | 32 | 35.2/35.2 | 83.2 | 20% GB | 4.4 | 8 | 8.8/8.8 | 20.8 | 77.2 | |
| 26 | GSC | 80% GSC | 17.6 | 32 | 35.2/35.2 | 83.2 | 20% GSC | 4.4 | 8 | 8.8/8.8 | 20.8 | 152.8 | 1.51 |
| | GB | 80% GB | 17.6 | 32 | 35.2/35.2 | 83.2 | 20% GB | 4.4 | 8 | 8.8/8.8 | 20.8 | 101.2 | |
| 27 | GSC | 80% GSC | 17.6 | 32 | 35.2/35.2 | 83.2 | 20% GSC | 4.4 | 8 | 8.8/8.8 | 20.8 | 163.6 | 1.81 |
| | GB | 80% GB | 17.6 | 32 | 35.2/35.2 | 83.2 | 20% GB | 4.4 | 8 | 8.8/8.8 | 20.8 | 90.4 | |
| 28 | GSC | 80% GSC | 17.6 | 32 | 35.2/35.2 | 83.2 | 20% GSC | 4.4 | 8 | 8.8/8.8 | 20.8 | 139.6 | 1.22 |
| | GB | 80% GB | 17.6 | 32 | 35.2/35.2 | 83.2 | 20% GB | 4.4 | 8 | 8.8/8.8 | 20.8 | 114.4 | |
| 29 | GSC | 80% GSC | 17.6 | 32 | 35.2/35.2 | 83.2 | 20% GSC | 4.4 | 8 | 8.8/8.8 | 20.8 | 114.4 | 0.82 |
| | GB | 80% GB | 17.6 | 32 | 35.2/35.2 | 83.2 | 20% GB | 4.4 | 8 | 8.8/8.8 | 20.8 | 139.6 | |
| 30 | GSC | 80% GSC | 17.6 | 32 | 35.2/35.2 | 83.2 | 20% GSC | 4.4 | 8 | 8.8/8.8 | 20.8 | 90.4 | 0.55 |
| | GB | 80% GB | 17.6 | 32 | 35.2/35.2 | 83.2 | 20% GB | 4.4 | 8 | 8.8/8.8 | 20.8 | 163.6 | |
| 31 | GSC | 80% GSC | 17.6 | 32 | 35.2/35.2 | 83.2 | 20% GSC | 4.4 | 8 | 8.8/8.8 | 20.8 | 101.2 | 0.66 |
| | GB | 80% GB | 17.6 | 32 | 35.2/35.2 | 83.2 | 20% GB | 4.4 | 8 | 8.8/8.8 | 20.8 | 152.8 | |
| 32 | GSC | 80% GSC | 17.6 | 32 | 35.2/35.2 | 83.2 | 20% GSC | 4.4 | 8 | 8.8/8.8 | 20.8 | 77.2 | 0.44 |
| | GB | 80% GB | 17.6 | 32 | 35.2/35.2 | 83.2 | 20% GB | 4.4 | 8 | 8.8/8.8 | 20.8 | 176.8 | |
| 33 | GSC | 80% GSC | 17.6 | 32 | 70.4 | 41.6/41.6 | 20% GSC | 4.4 | 8 | 17.6 | 10.4/10.4 | 172 | 2.10 |
| | GB | 80% GB | 17.6 | 32 | 70.4 | 41.6/41.6 | 20% GB | 4.4 | 8 | 17.6 | 10.4/10.4 | 82 | |
| 34 | GSC | 80% GSC | 17.6 | 32 | 70.4 | 41.6/41.6 | 20% GSC | 4.4 | 8 | 17.6 | 10.4/10.4 | 148 | 1.40 |
| | GB | 80% GB | 17.6 | 32 | 70.4 | 41.6/41.6 | 20% GB | 4.4 | 8 | 17.6 | 10.4/10.4 | 106 | |
| 35 | GSC | 80% GSC | 17.6 | 32 | 70.4 | 41.6/41.6 | 20% GSC | 4.4 | 8 | 17.6 | 10.4/10.4 | 158.8 | 1.67 |
| | GB | 80% GB | 17.6 | 32 | 70.4 | 41.6/41.6 | 20% GB | 4.4 | 8 | 17.6 | 10.4/10.4 | 95.2 | |
| 36 | GSC | 80% GSC | 17.6 | 32 | 70.4 | 41.6/41.6 | 20% GSC | 4.4 | 8 | 17.6 | 10.4/10.4 | 134.8 | 1.13 |
| | GB | 80% GB | 17.6 | 32 | 70.4 | 41.6/41.6 | 20% GB | 4.4 | 8 | 17.6 | 10.4/10.4 | 119.2 | |
| 37 | GSC | 80% GSC | 17.6 | 32 | 70.4 | 41.6/41.6 | 20% GSC | 4.4 | 8 | 17.6 | 10.4/10.4 | 119.2 | 0.88 |
| | GB | 80% GB | 17.6 | 32 | 70.4 | 41.6/41.6 | 20% GB | 4.4 | 8 | 17.6 | 10.4/10.4 | 134.8 | |

TABLE 2B-continued

| | | | | | II Mbps | III | | | | II Mbps | III | | GFP: |
| | | | X | Y | | | | X | Y | | | | |
| | | | 22 | 40 | 44 | 52 | | 22 | 40 | 44 | 52 | Sum: GFP | GSC/GB |
|---|---|---|---|---|---|---|---|---|---|---|---|---|---|
| 38 | GSC | 80% GSC | 17.6 | 32 | 70.4 | 41.6/41.6 | 20% GSC | 4.4 | 8 | 17.6 | 10.4/10.4 | 95.2 | 0.60 |
| | GB | 80% GB | 17.6 | 32 | 70.4 | 41.6/41.6 | 20% GB | 4.4 | 8 | 17.6 | 10.4/10.4 | 158.8 | |
| 39 | GSC | 80% GSC | 17.6 | 32 | 70.4 | 41.6/41.6 | 20% GSC | 4.4 | 8 | 17.6 | 10.4/10.4 | 106 | 0.72 |
| | GB | 80% GB | 17.6 | 32 | 70.4 | 41.6/41.6 | 20% GB | 4.4 | 8 | 17.6 | 10.4/10.4 | 148 | |
| 40 | GSC | 80% GSC | 17.6 | 32 | 70.4 | 41.6/41.6 | 20% GSC | 4.4 | 8 | 17.6 | 10.4/10.4 | 82 | 0.48 |
| | GB | 80% GB | 17.6 | 32 | 70.4 | 41.6/41.6 | 20% GB | 4.4 | 8 | 17.6 | 10.4/10.4 | 172 | |
| 41 | GSC | 80% GSC | 17.6 | 32 | 70.4 | 41.6/41.6 | 20% GSC | 4.4 | 8 | 17.6 | 10.4/10.4 | 172 | 2.10 |
| | GB | 80% GB | 17.6 | 32 | 70.4 | 41.6/41.6 | 20% GB | 4.4 | 8 | 17.6 | 10.4/10.4 | 82 | |
| 42 | GSC | 80% GSC | 17.6 | 32 | 70.4 | 41.6/41.6 | 20% GSC | 4.4 | 8 | 17.6 | 10.4/10.4 | 148 | 1.40 |
| | GB | 80% GB | 17.6 | 32 | 70.4 | 41.6/41.6 | 20% GB | 4.4 | 8 | 17.6 | 10.4/10.4 | 106 | |
| 43 | GSC | 80% GSC | 17.6 | 32 | 70.4 | 41.6/41.6 | 20% GSC | 4.4 | 8 | 17.6 | 10.4/10.4 | 158.8 | 1.67 |
| | GB | 80% GB | 17.6 | 32 | 70.4 | 41.6/41.6 | 20% GB | 4.4 | 8 | 17.6 | 10.4/10.4 | 95.2 | |
| 44 | GSC | 80% GSC | 17.6 | 32 | 70.4 | 41.6/41.6 | 20% GSC | 4.4 | 8 | 17.6 | 10.4/10.4 | 134.8 | 1.13 |
| | GB | 80% GB | 17.6 | 32 | 70.4 | 41.6/41.6 | 20% GB | 4.4 | 8 | 17.6 | 10.4/10.4 | 119.2 | |
| 45 | GSC | 80% GSC | 17.6 | 32 | 70.4 | 41.6/41.6 | 20% GSC | 4.4 | 8 | 17.6 | 10.4/10.4 | 119.2 | 0.88 |
| | GB | 80% GB | 17.6 | 32 | 70.4 | 41.6/41.6 | 20% GB | 4.4 | 8 | 17.6 | 10.4/10.4 | 134.8 | |
| 46 | GSC | 80% GSC | 17.6 | 32 | 70.4 | 41.6/41.6 | 20% GSC | 4.4 | 8 | 17.6 | 10.4/10.4 | 95.2 | 0.60 |
| | GB | 80% GB | 17.6 | 32 | 70.4 | 41.6/41.6 | 20% GB | 4.4 | 8 | 17.6 | 10.4/10.4 | 158.8 | |
| 47 | GSC | 80% GSC | 17.6 | 32 | 70.4 | 41.6/41.6 | 20% GSC | 4.4 | 8 | 17.6 | 10.4/10.4 | 106 | 0.72 |
| | GB | 80% GB | 17.6 | 32 | 70.4 | 41.6/41.6 | 20% GB | 4.4 | 8 | 17.6 | 10.4/10.4 | 148 | |
| 48 | GSC | 80% GSC | 17.6 | 32 | 70.4 | 41.6/41.6 | 20% GSC | 4.4 | 8 | 17.6 | 10.4/10.4 | 82 | 0.48 |
| | GB | 80% GB | 17.6 | 32 | 70.4 | 41.6/41.6 | 20% GB | 4.4 | 8 | 17.6 | 10.4/10.4 | 172 | |
| 49 | GSC | 80% GSC | 17.6 | 32 | 35.2/35.2 | 41.6/41.6 | 20% GSC | 4.4 | 8 | 8.8/8.8 | 10.4/10.4 | 145.6 | 1.34 |
| | GB | 80% GB | 17.6 | 32 | 35.2/35.2 | 41.6/41.6 | 20% GB | 4.4 | 8 | 8.8/8.8 | 10.4/10.4 | 108.8 | |
| 50 | GSC | 80% GSC | 17.6 | 32 | 35.2/35.2 | 41.6/41.6 | 20% GSC | 4.4 | 8 | 8.8/8.8 | 10.4/10.4 | 121.6 | 0.92 |
| | GB | 80% GB | 17.6 | 32 | 35.2/35.2 | 41.6/41.6 | 20% GB | 4.4 | 8 | 8.8/8.8 | 10.4/10.4 | 132.4 | |
| 51 | GSC | 80% GSC | 17.6 | 32 | 35.2/35.2 | 41.6/41.6 | 20% GSC | 4.4 | 8 | 8.8/8.8 | 10.4/10.4 | 132.4 | 1.09 |
| | GB | 80% GB | 17.6 | 32 | 35.2/35.2 | 41.6/41.6 | 20% GB | 4.4 | 8 | 8.8/8.8 | 10.4/10.4 | 121.6 | |
| 52 | GSC | 80% GSC | 17.6 | 32 | 35.2/35.2 | 41.6/41.6 | 20% GSC | 4.4 | 8 | 8.8/8.8 | 10.4/10.4 | 108.4 | 0.74 |
| | GB | 80% GB | 17.6 | 32 | 35.2/35.2 | 41.6/41.6 | 20% GB | 4.4 | 8 | 8.8/8.8 | 10.4/10.4 | 145.6 | |
| 53 | GSC | 80% GSC | 17.6 | 32 | 35.2/35.2 | 41.6/41.6 | 20% GSC | 4.4 | 8 | 8.8/8.8 | 10.4/10.4 | 145.6 | 1.34 |
| | GB | 80% GB | 17.6 | 32 | 35.2/35.2 | 41.6/41.6 | 20% GB | 4.4 | 8 | 8.8/8.8 | 10.4/10.4 | 108.4 | |
| 54 | GSC | 80% GSC | 17.6 | 32 | 35.2/35.2 | 41.6/41.6 | 20% GSC | 4.4 | 8 | 8.8/8.8 | 10.4/10.4 | 121.6 | 0.92 |
| | GB | 80% GB | 17.6 | 32 | 35.2/35.2 | 41.6/41.6 | 20% GB | 4.4 | 8 | 8.8/8.8 | 10.4/10.4 | 132.4 | |
| 55 | GSC | 80% GSC | 17.6 | 32 | 35.2/35.2 | 41.6/41.6 | 20% GSC | 4.4 | 8 | 8.8/8.8 | 10.4/10.4 | 132.4 | 1.09 |
| | GB | 80% GB | 17.6 | 32 | 35.2/35.2 | 41.6/41.6 | 20% GB | 4.4 | 8 | 8.8/8.8 | 10.4/10.4 | 121.6 | |

TABLE 2B-continued

| | | | 80% Asymmetric Deposition | | | | | | | | | | |
| | | | 80% asymmetric deposition | | | | | | | | | | |
| | | | X | Y | II Mbps | III | X | Y | II Mbps | III | | GFP: |
| | | | 22 | 40 | 44 | 52 | 22 | 40 | 44 | 52 | Sum: GFP | GSC/GB |
|---|---|---|---|---|---|---|---|---|---|---|---|---|
| 56 | GSC | 80% GSC | 17.6 | 32 | 35.2/35.2 | 41.6/41.6 | 20% GSC | 4.4 | 8 | 8.8/8.8 | 10.4/10.4 | 108.4 | 0.74 |
| | GB | 80% GB | 17.6 | 32 | 35.2/35.2 | 41.6/41.6 | 20% GB | 4.4 | 8 | 8.8/8.8 | 10.4/10.4 | 145.6 | |
| 57 | GSC | 80% GSC | 17.6 | 32 | 35.2/35.2 | 41.6/41.6 | 20% GSC | 4.4 | 8 | 8.8/8.8 | 10.4/10.4 | 145.6 | 1.34 |
| | GB | 80% GB | 17.6 | 32 | 35.2/35.2 | 41.6/41.6 | 20% GB | 4.4 | 8 | 8.8/8.8 | 10.4/10.4 | 108.4 | |
| 58 | GSC | 80% GSC | 17.6 | 32 | 35.2/35.2 | 41.6/41.6 | 20% GSC | 4.4 | 8 | 8.8/8.8 | 10.4/10.4 | 121.6 | 0.92 |
| | GB | 80% GB | 17.6 | 32 | 35.2/35.2 | 41.6/41.6 | 20% GB | 4.4 | 8 | 8.8/8.8 | 10.4/10.4 | 132.4 | |
| 59 | GSC | 80% GSC | 17.6 | 32 | 35.2/35.2 | 41.6/41.6 | 20% GSC | 4.4 | 8 | 8.8/8.8 | 10.4/10.4 | 132.4 | 1.09 |
| | GB | 80% GB | 17.6 | 32 | 35.2/35.2 | 41.6/41.6 | 20% GB | 4.4 | 8 | 8.8/8.8 | 10.4/10.4 | 121.6 | |
| 60 | GSC | 80% GSC | 17.6 | 32 | 35.2/35.2 | 41.6/41.6 | 20% GSC | 4.4 | 8 | 8.8/8.8 | 10.4/10.4 | 108.4 | 0.74 |
| | GB | 80% GB | 17.6 | 32 | 35.2/35.2 | 41.6/41.6 | 20% GB | 4.4 | 8 | 8.8/8.8 | 10.4/10.4 | 145.6 | |
| 61 | GSC | 80% GSC | 17.6 | 32 | 35.2/35.2 | 41.6/41.6 | 20% GSC | 4.4 | 8 | 8.8/8.8 | 10.4/10.4 | 145.6 | 1.34 |
| | GB | 80% GB | 17.6 | 32 | 35.2/35.2 | 41.6/41.6 | 20% GB | 4.4 | 8 | 8.8/8.8 | 10.4/10.4 | 108.4 | |
| 62 | GSC | 80% GSC | 17.6 | 32 | 35.2/35.2 | 41.6/41.6 | 20% GSC | 4.4 | 8 | 8.8/8.8 | 10.4/10.4 | 121.6 | 0.92 |
| | GB | 80% GB | 17.6 | 32 | 35.2/35.2 | 41.6/41.6 | 20% GB | 4.4 | 8 | 8.8/8.8 | 10.4/10.4 | 132.4 | |
| 63 | GSC | 80% GSC | 17.6 | 32 | 35.2/35.2 | 41.6/41.6 | 20% GSC | 4.4 | 8 | 8.8/8.8 | 10.4/10.4 | 132.4 | 1.09 |
| | GB | 80% GB | 17.6 | 32 | 35.2/35.2 | 41.6/41.6 | 20% GB | 4.4 | 8 | 8.8/8.8 | 10.4/10.4 | 121.6 | |
| 64 | GSC | 80% GSC | 17.6 | 32 | 35.2/35.2 | 41.6/41.6 | 20% GSC | 4.4 | 8 | 8.8/8.8 | 10.4/10.4 | 108.4 | 0.74 |
| | GB | 80% GB | 17.6 | 32 | 35.2/35.2 | 41.6/41.6 | 20% GB | 4.4 | 8 | 8.8/8.8 | 10.4/10.4 | 145.6 | |

| Cut-off | Asymmetry | Symmetry | Asymmetry (Inverted) | Boder Line |
|---|---|---|---|---|
| 1.5 | 12 (18.75%) | 34 (53.13%) | 12 (18.75%) | 6 (9.38%) |

Figure 21:
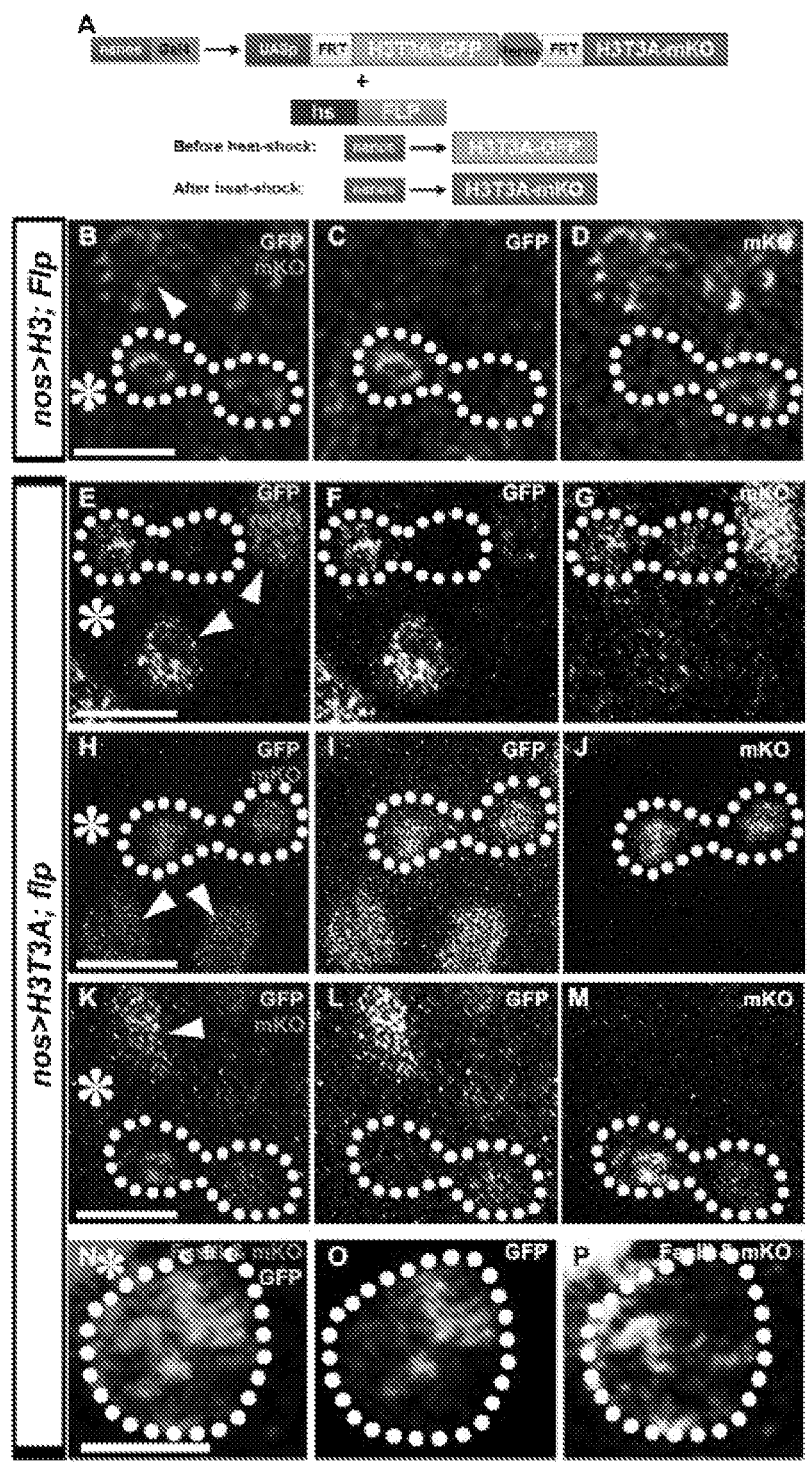
FIG. 21A-FIG. 21P is a series of diagrams and photographs demonstrating that expression of H3T3A changes the asymmetric H3 segregation pattern in mitotic GSCs.
FIG. 21B-FIG. 21D shows a telophase GSC expressing nos>FRT-H3-GFP-PolyA-FRT-H3-mKO-PolyA (nos>H3) during the second mitosis after heat-shock-induced genetic switch show conventional asymmetric segregation pattern.
FIG. 21E-FIG. 21M shows telophase GSCs expressing nos>FRT-H3T3A-GFP-PolyA-FRT-H3T3A-mKO-PolyA (nos>H3T3A) during the second mitosis after heat-shock-induced genetic switch show convention asymmetric pattern (FIG. 21E-FIG. 21G), symmetric pattern (FIG. 21H-FIG. 21J), or inverted asymmetric pattern (see FIG. 21K-FIG. 21M). For FIG. 21N-FIG. 21P, a prophase GSC expressing nos>FRT-H3T3A-GFP-PolyA-FRT-H3T3A-mKO-PolyA (nos>H3T3A) during the second mitosis after heat-shock-induced genetic switch show separable GFP and mKO signals. Asterisk, hub; white dotted outline, mitotic GSCs at telophase (FIG. 21B-FIG. 21M) or prophase (FIG. 21N-FIG. 21P); arrowheads, interphase GSCs or GBs that show much less condensed nuclei. Scale bars, 5 μm.
Figure 23:
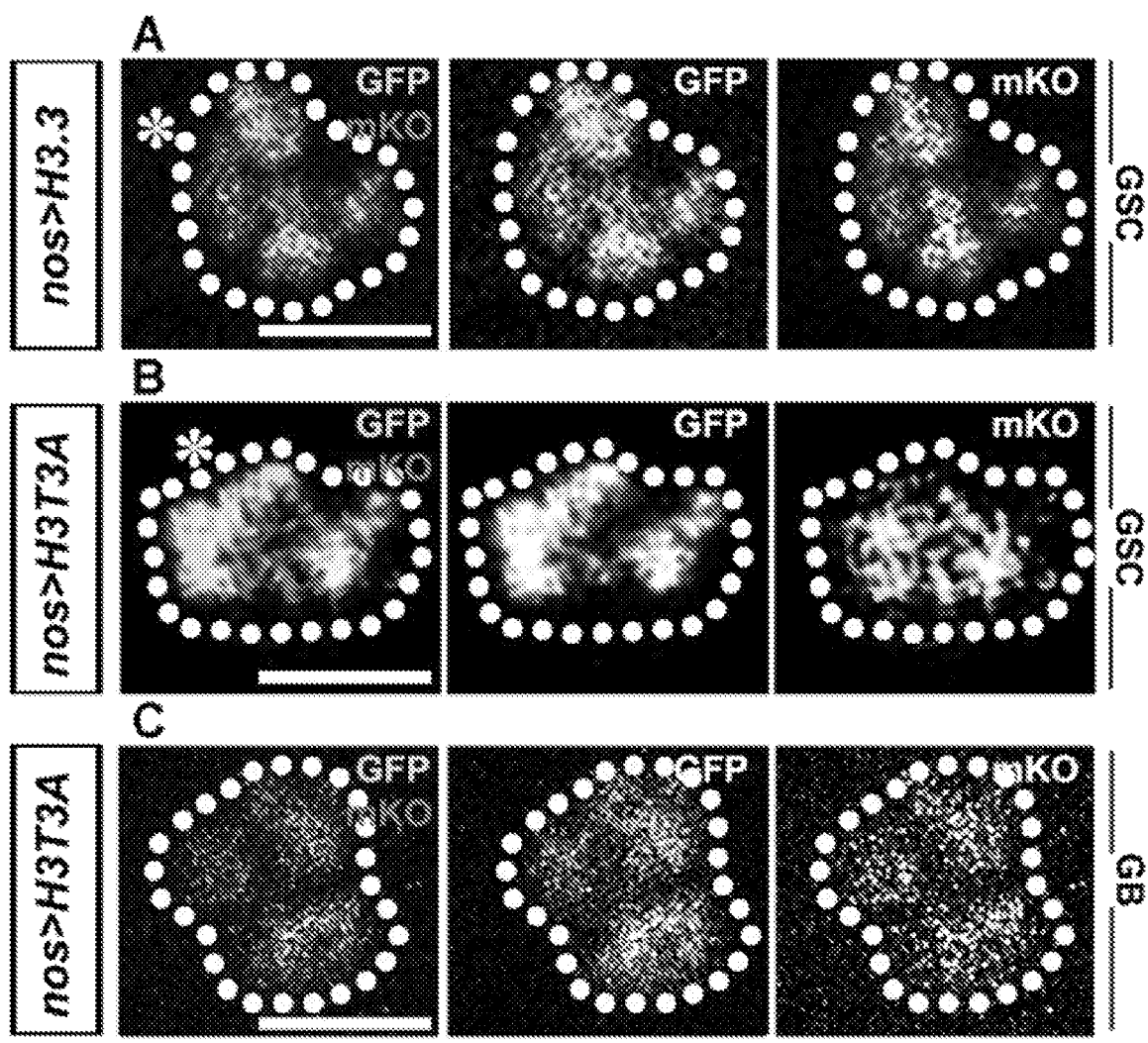
FIG. 23A-FIG. 23C is a series of photographs demonstrating that molecular and cellular specificity of histone separation patterns in prophase germ cells, and spatial and temporal specificity of the H3T3P signal.

Example 3: Expression of H3T3A Changes the Assymetric H3 Segregation Pattern in Mitotic GSCs Because expression of the H3T3A provides a loss-of-function condition for H3T3P, as described herein, it was examined whether asymmetric histone segregation is affected in H3T3A-expressing GSCs using the dual-color labeling strategy (FIG. 21A). As a control, a similar system was used with wild-type H3 and it was found that pre-existing H3-GFP and newly synthesized H3-mKO are asymmetrically segregated in telophase GSCs during the second mitosis after heat-shock-induced genetic switch (FIG. 21B-FIG. 21D), consistent with previous reports (Tran et al., 2012). By contrast, a dramatic shift in histone inheritance patterns from predominantly asymmetric to predominantly symmetric pattern (FIG. 21H-FIG. 21J) was found, using the dual-color trans-gene with H3T3A (FIG. 21A). Although the majority of GSCs expressing H3T3A exhibited a symmetric pattern of histone inheritance (FIG. 21H-FIG. 21J), the conventional asymmetric pattern resembling that of wild-type H3 in telophase GSCs (FIG. 21E-FIG. 21G) was still detected. Surprisingly, the inverted asymmetric pattern (FIGS. 3K-3M) was also observed. If pre-existing and newly synthesized histones are randomly incorporated during the first step (FIG. 5B), no separation between GFP and mKO signals should be detectable during GSC asymmetric division. The fact that conventional and inverted asymmetric segregation patterns in telophase GSCs (FIG. 21E-FIG. 21G and FIG. 21K-FIG. 21M) were identified suggests that the establishment of histone asymmetry prior to mitosis may not be affected. The observed defects in proper asymmetric segregation therefore arise upon mitotic entry when sister chromatids containing different populations of H3 need to be recognized and segregated to the appropriate daughter cell (FIG. 5B, step two). Consistent with this hypothesis, separable H3T3A-GFP and H3T3A-mKO could still be detected in prophase GSCs (FIG. 21N-FIG. 2W and FIG. 23B), but not in a control prophase GB (FIG. 23C).

Because expression of H3T3A changes H3 distribution patterns in post mitotic GSC-GB pairs (see FIG. 3A-FIG. 3I), the percentage of each of these distribution pattern was quantified. GFP signal was mainly used to account for different patterns, for example, in FIG. 22J: the conventional asymmetric patterns are in zone I, with GFP ratio in GSC/GB>1.55; the symmetric patterns are in zone II, with GFP ratio in GSC/GB<1.45 but>0.69 (i.e., GB/GSC<1.45); and the inverted asymmetric patterns are in zone III, with GFP ratio in GB/GSC>1.55. The 1.5-fold cutoff is based on the quantification range of symmetric H3 distribution in spermatogonial cells and symmetric H3.3 distribution in GSC-GB pairs (Tran et al., 2012, 2013). The GFP ratio reflects the establishment of asymmetric histone distribution on sister chromatids more reliably than mKO ratio for two reasons. First, when mKO fluorescence intensity is measured in post-mitotic GSC-GB pairs, both cells are actively undergoing S phase for the next mitosis and exhibit robust incorporation of mKO-labeled newly synthesized histones (FIG. 3C). Second, any histone turn-over that incorporates newly synthesized mKO-labeled histones (Deal et al., 2010; Dion et al., 2007) during processes such as transcription may not be sister chromatid-specific.

The GFP distribution patterns were quantified in post-mitotic GSC-GB pairs in H3T3A-expressing testes (FIG. 22J and FIG. 3J), 71.9% (46/64) of pairs showed a symmetric pattern of inheritance (FIG. 22K; Table 1). By contrast, in wild-type H3-expressing testes, 87.3% (48/55) of pairs showed an asymmetric pattern of inheritance (FIG. 22K; Table 1). Moreover, in H3T3A-expressing testes, asymmetric patterns could be observed in two distinct modes at lower frequencies: 9.4% (6/64) conventional asymmetry, 12.5% (8/64) inverted asymmetry, and 6.3% (4/64) at the borderline (1.45- to 1.55-fold) between asymmetry and symmetry (FIG. 22K; Table 1). Noticeably, no GSC-GB pair showed the inverted asymmetric pattern (zone III in FIG. 22J) in wild-type H3-expressing testes (FIG. 22J and FIG. 22K), suggesting that such a pattern is specifically induced by H3T3A-expression.

Example 4: Expression of H3T3A Causes Several Germline Defects

Figure 25:
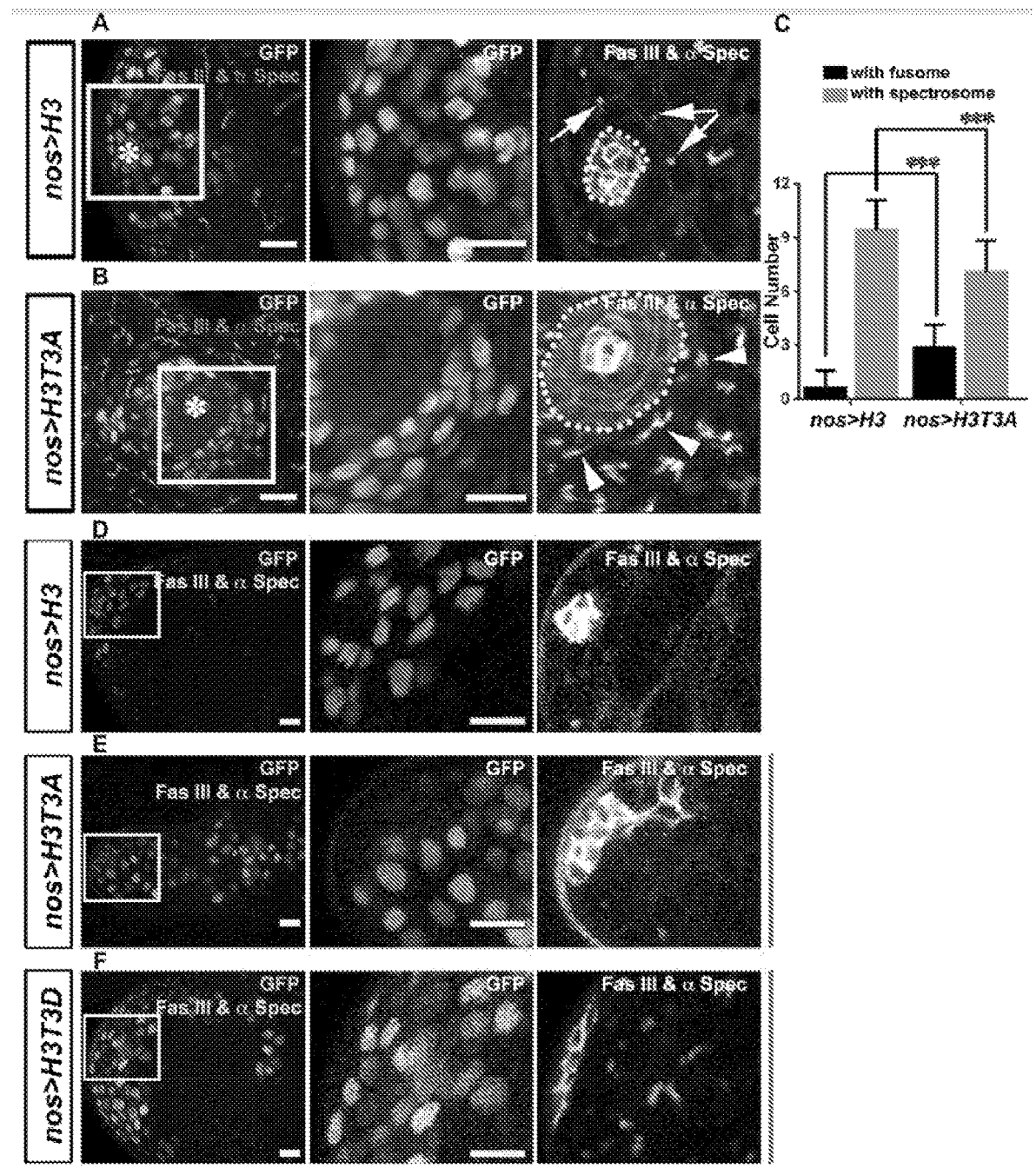
FIG. 25A-FIG. 25F is a series of photographs and graphs demonstratimg that Expression of H3T3A or H3T3D Using the nos-Gal4 Driver Leads to Similar Phenotypes.

A spectrum of cellular defects could be detected in nos>H3T3A testes after the level of H3T3P is effectively reduced (FIG. 10A-FIG. 10P). Compared to testes expressing the wild-type H3 (FIG. 4A-FIG. 4D, FIG. 25A, FIG. 25D, and FIG. 11A-FIG. 11E), H3T3A-expressing testes exhibited phenotypes with both germline and somatic defects (FIG. 4E-FIG. 4H, FIG. 14N-FIG. 14Q, FIG. 25B, FIG. 25E, and FIG. 11F-FIG. 11J). First, GSCs expressing the H3T3A transgene were not maintained properly. In testes without transgene or expressing H3-GFP, only germ cells with dotted spectrosome structure (de Cuevas and Spradling, 1998; Hime et al., 1996; Lin et al., 1994) were detectable next to the hub cells (FIG. 25A, arrows). However, in nos>H3T3A testes, germ cells with branched fusome structure were detected adjacent to the hub region (arrowheads in FIG. 25B), suggesting that GSCs either undergo precocious differentiation or cell death, thereby allowing more differentiated spermatogonial cysts to take their place. Quantification of these two distinct cellular structures (spectrosome versus fusome) showed a significant loss of GSCs in H3T3A-expressing testes (FIG. 25C). Second, a significant expansion of germline tumors carrying early-stage cellular markers, including nos-driven GFP expression (FIG. 4E, FIG. 4F, FIG. 25E, and FIG. 11F-FIG. 11O), spectrosome structure (FIG. 4E, FIG. 4G, FIG. 25E, FIG. 11F-FIG. 11O, and FIG. 12A-FIG. 12H), and condensed nuclei (Chen et al., 2013; Schulz et al., 2004; Tran et al., 2000) (FIG. 4H and FIG. 11F-FIG. 11O) were observed. Based on these cellular markers, the tumors of progenitor germ cells developed in nos>H3T3A testes were noticeably heterogeneous (FIG. 12A-FIG. 12H). For example, some tumor cells maintained strong GFP expression (FIG. 12A-FIG. 12H), a mark indicative of active nos-Gal4 activity, and exhibited spectrosome structure (FIG. 12A-FIG. 12H), suggesting that they are an early-stage GSC and/or GB cell tumor. Conversely, other tumor cells exhibited loss of GFP expression and a fusome structure (FIG. 12A-FIG. 12H), suggesting that they are a later-stage spermatogonial tumor. This heterogeneity in tumor types is likely due to the heterogeneity observed in histone inheritance patterns (FIG. 21A-FIG. 21P, FIG. 3A-FIG. 3I, and FIG. 22J and FIG. 22K). Third, the nos>H3T3A males had gradually decreased fertility (FIG. 11P), consistent with the progression of germline defects (FIG. 11F-FIG. 11O) and eventual germ cell loss (FIG. 14N-FIG. 14Q and FIG. 14V). While the progenitor germ cell tumor phenotype was not detected in nos>H3 (n=19) control testes, it was observed in 42.9% of nos>H3T3A testes (n=42) (FIG. 14V). The germ cell loss phenotype was detected in 15.8% of nos>H3 (n=19) control testes but in 47.6% of nos>H3T3A testes (n=42) (FIG. 14V). The loss of germ cells in 15.8% of control testes is likely due to age-related effect (Boyle et al., 2007; Cheng et al., 2008; Toledano et al., 2012; Wallenfang et al., 2006). Last, nos>H3T3A testes (FIG. 4G, inset, and FIG. 25B, yellow outline) showed a substantial hub enlargement (FIG. 14M) compared to nos>H3 testes (FIG. 4C, inset, and FIG. 25A, yellow outline), most likely as a secondary defect due to GSC loss as reported previously (Dinardo et al., 2011; Gotnczy and DiNardo, 1996; Monk et al., 2010; Tazuke et al., 2002). In summary, development of these germline defects in adult flies suggests that H3T3P is likely required for both GSC maintenance and proper differentiation of GB.

Figure 15:
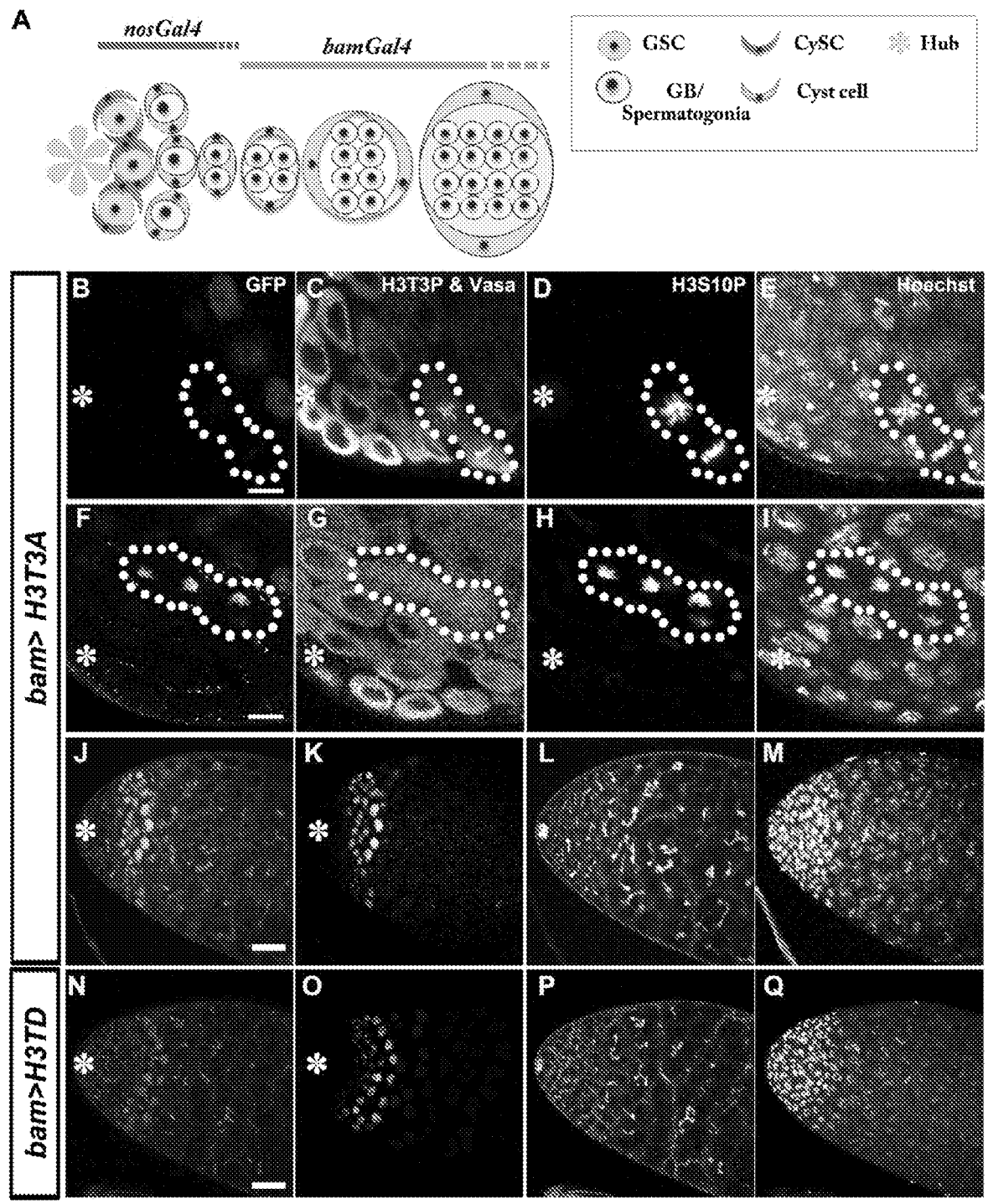

Example 5: Expression of H3T3A in Late-Stage Germ Cells or Somatic Cells does not Cause Germline Tumors The GSC loss, germline tumor and hub enlargement phenotypes in nos>H3T3A testes were specifically caused by expressing H3T3A in early-stage germ cells. A later-stage germline driver, bam-Gal4 (Cheng et al., 2008; Eun et al., 2014; Schulz et al., 2004) (FIG. 15A), was used to turn on the same H3T3A transgene in four-cell and later stage germ cells. In doing so, H3T3P was effectively reduced in the more differentiated germ cells (FIG. 15G). However, in this population of symmetrically dividing cells, the phenotypes (FIG. 15J-FIG. 15M) observed in nos>H3T3A testes (FIG. 4A-FIG. 4L, FIG. 14N-FIG. 14V, FIG. 25A-FIG. 25F, FIG. 11A-FIG. 11P, and FIG. 12A-FIG. 12H) were not detected.

In addition to GSCs, another type of adult stem cell residing in the Drosophila testis niche is the cyst stem cell (CySC), which, under normal conditions, is the only mitotically active somatic gonadal cell type (Dinardo et al., 2011). When a somatic cell-specific Tj-Gal4 driver (Tanentzapf et al., 2007) was used to express H3T3A, it is sufficient to reduce H3T3P signal specifically in CySCs (FIG. 26A). However, no dramatic cellular defects were detected when comparing Tj>H3T3A (FIG. 26C) with Tj>H3 testes (FIG. 26B). In summary, these stage-specific and cell type-specific effects caused by H3T3A expression suggest that the phenotype observed in nos>H3T3A testes is unlikely the result of a global perturbation of general cellular machineries.

Figure 24:
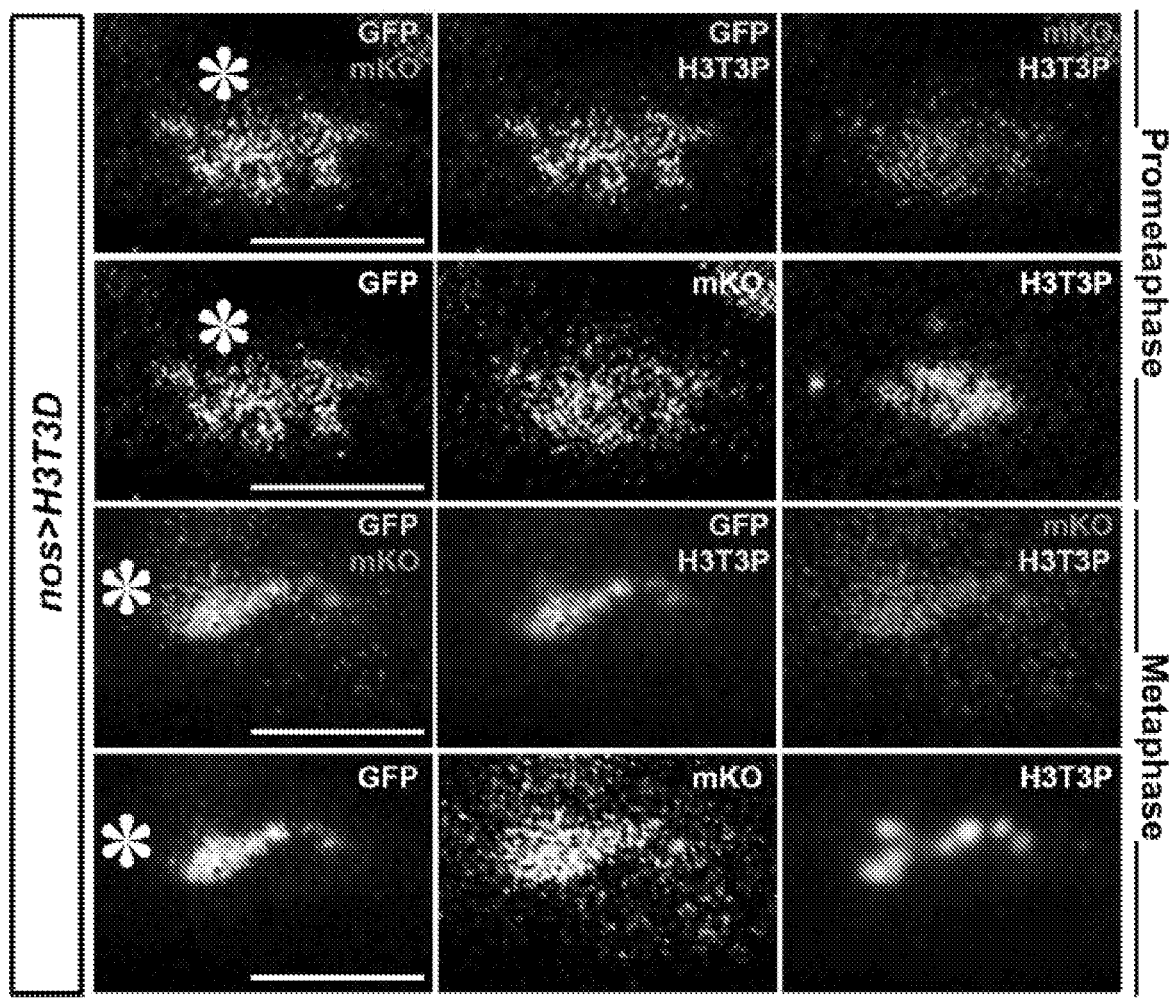
FIG. 24 is a series of photographs demonstrating that H3T3P signal in H3T3D-expressing cells and the effects of H3T3A or H3T3D on histone inheritance patterns. Immunostaining using antibody against H3T3P in a prophase GSC and a metaphase GSC expressing the dual-color H3T3D: pre-existing H3T3D-GFP and newly synthesized H3T3D-mKO signals largely overlap and H3T3P is detectable. Asterisks: hub. Scale bars: 5 μm.

Example 6: Expression of H3T3D in Early-, but Not Late-Stage, Germ Cells Leads to Randomized H3 Inheritance and Cellular Defects To further understand how H3T3P functions in GSCs, a different H3T3 mutant was expressed for which the T3 residue was converted to the phosphomimetic aspartic acid (D), under the hypothesis that such a mutation may disrupt the temporal order of H3T3 phosphorylation (FIG. 1G-FIG. 1L and FIG. 7M-FIG. 7X). Indeed, expression of H3T3D in early germ cells using a similar dual-color labeling strategy (as described for H3T3A in FIG. 21A) also randomizes pre-existing H3T3D and newly synthesized H3T3D inheritance patterns (FIG. 22J, FIG. 22K, and FIG. 16I; Table 1): approximately 79.0% (45/57) of GSC-GB pairs showed symmetric inheritance patterns, 7.0% (4/57) showed conventional asymmetry, and 10.5% (6/57) showed inverted asymmetry, with the remaining 3.5% (2/57) of pairs at the borderline between asymmetry and symmetry (1.45- to 1.55-fold). The randomized H3T3D inheritance patterns cannot be attributed to loss of H3T3P, as H3T3P is still detectable in H3T3D-expressing GSCs (FIG. 24). These data suggest that it is likely the timing of the H3T3 phosphorylation that is important for normal GSC activity.

In addition, both progenitor germline tumor (FIG. 4I-FIG. 4L and FIG. 25F) and germ cell loss (FIG. 14R-FIG. 14U) phenotypes could be detected in nos-H3T3D testes (FIG. 14V). Quantification showed significant decrease of GSCs in nos>H3T3D testes (6.84±0.41, n=37) compared to that of the control nos>H3 testes (8.68±0.31, n=19; p<0.001). Moreover, similar to the nos>H3T3A testes, the hub region in nos>H3T3D testes was also enlarged compared to the control nos>H3 testes (FIG. 14M and FIG. 25F), most likely as a secondary effect due to the loss of GSCs. By contrast, no germline tumor phenotype was found when the same transgene H3T3D-GFP was driven by the bam-Gal4 driver (FIG. 15N-FIG. 15Q).

Since both reduction of H3T3P by expression of H3T3A and the mimicking of H3T3P by expression of H3T3D result in similar histone inheritance and germline defects, phosphorylation of H3T3 might require a tight temporal control during GSC mitosis. Therefore, expressing either the H3T3A or the H3T3D may lead to loss of this control and similar defects in histone inheritance patterns as well as abnormal germline activity.

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. Genbank and NCBI submissions indicated by accession number cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of inducing cell death in a rapidly dividing cell comprising:
   contacting a rapidly dividing cell with an agent that reduces phosphorylation at threonine 3 of histone 3 (H3T3P), thereby inducing cell cycle arrest followed by cell death,
   wherein the agent that reduces phosphorylation of H3T3P comprises an H3T3A mutant protein or an H3T3D mutant protein.

2. The method of claim 1, wherein said rapidly dividing cell is a tumor cell.

3. The method of claim 1, wherein the agent comprises a H3T3A mutant protein.

4. The method of claim 1, wherein the agent comprises a H3T3D mutant protein.

5. The method of claim 1 further comprising administering a chemotherapeutic agent distinct from the agent that reduces phosphorylation.

6. The method of claim 5, wherein said chemotherapeutic agent comprises radiotherapy or a cell death-inducing agent.

7. A method of inhibiting tumor growth comprising:
   contacting a tumor cell with an agent that reduces phosphorylation at threonine 3 of histone 3 (H3T3P), thereby inhibiting tumor growth
   wherein the agent that reduces phosphorylation of H3T3P comprises an H3T3A mutant protein or an H3T3D mutant protein.

8. The method of claim 1 wherein the rapidly dividing cell is a hematological malignancy.

9. The method of claim 7, wherein the agent comprises a H3T3A mutant protein.

10. The method of claim 7, wherein the agent comprises a H3T3D mutant protein.

11. The method of claim 7 wherein the agent is administered to a subject.

12. The method of claim 10 wherein the subject is a human.

\* \* \* \* \*

SEQUENCE LISTING

```
<160> NUMBER OF SEQ ID NOS: 18

<210> SEQ ID NO 1
<211> LENGTH: 411
<212> TYPE: DNA
<213> ORGANISM: Drosophila melanogaster

<400> SEQUENCE: 1
atggctcgta ccaagcaaac tgctcgcaaa tcgactggtg gaaaggcgcc acgcaaacaa      60
ctggctacta aggccgctcg caagagtgct ccagccaccg gaggtgtgaa gaagccccac     120
cgctatcgcc ctggaaccgt ggccttgcgt gaaattcgtc gctaccaaaa gagcaccgag     180
cttctaatcc gcaagctgcc tttccagcgt ctggtgcgtg aaatcgctca ggactttaag     240
acggacttgc gattccagag ctcggcggtt atggctctgc aggaagctag cgaagcctac     300
ctggttggtc tcttcgaaga taccaacttg tgtgccattc atgccaagcg tatcaccata     360
atgcccaaag acatccagtt agcgcgacgc attcgcggcg agcgtgctta a              411

<210> SEQ ID NO 2
<211> LENGTH: 411
<212> TYPE: DNA
<213> ORGANISM: Drosophila melanogaster

<400> SEQUENCE: 2
atggctcgtg ccaagcaaac tgctcgcaaa tcgactggtg gaaaggcgcc acgcaaacaa      60
ctggctacta aggccgctcg caagagtgct ccagccaccg gaggtgtgaa gaagccccac     120
cgctatcgcc ctggaaccgt ggccttgcgt gaaattcgtc gctaccaaaa gagcaccgag     180
```

```
cttctaatcc gcaagctgcc tttccagcgt ctggtgcgtg aaatcgctca ggactttaag    240
acggacttgc gattccagag ctcggcggtt atggctctgc aggaagctag cgaagcctac    300
ctggttggtc tcttcgaaga taccaacttg tgtgccattc atgccaagcg tatcaccata    360
atgcccaaag acatccagtt agcgcgacgc attcgcggcg agcgtgctta a             411

<210> SEQ ID NO 3
<211> LENGTH: 411
<212> TYPE: DNA
<213> ORGANISM: Homo sapiens

<400> SEQUENCE: 3
atggcccgaa ccaagcagac tgcgcgcaag tcaacgggtg gcaaggcgcc gcgcaagcag     60
ctggccacca aggtggctcg caagagcgca cctgccactg gcggcgtgaa gaagccgcac    120
cgctaccggc ccggcacggt ggcgcttcgc gagatccgcc gctaccagaa gtccactgag    180
ctgctaatcc gcaagttgcc cttccagcgg ctgatgcgcg agatcgctca ggactttaag    240
accgacctgc gcttccagag ctcggccgtg atggcgctgc aggaggcgtg cgagtcttac    300
ctggtggggc tgtttgagga caccaacctg tgtgtcatcc atgccaaacg ggtcaccatc    360
atgcctaagg acatccagct ggcacgccgt atccgcgggg agcgggccta g             411

<210> SEQ ID NO 4
<211> LENGTH: 411
<212> TYPE: DNA
<213> ORGANISM: Homo sapiens

<400> SEQUENCE: 4
atggcccgag ccaagcagac tgcgcgcaag tcaacgggtg gcaaggcgcc gcgcaagcag     60
ctggccacca aggtggctcg caagagcgca cctgccactg gcggcgtgaa gaagccgcac    120
cgctaccggc ccggcacggt ggcgcttcgc gagatccgcc gctaccagaa gtccactgag    180
ctgctaatcc gcaagttgcc cttccagcgg ctgatgcgcg agatcgctca ggactttaag    240
accgacctgc gcttccagag ctcggccgtg atggcgctgc aggaggcgtg cgagtcttac    300
ctggtggggc tgtttgagga caccaacctg tgtgtcatcc atgccaaacg ggtcaccatc    360
atgcctaagg acatccagct ggcacgccgt atccgcgggg agcgggccta g             411

<210> SEQ ID NO 5
<211> LENGTH: 411
<212> TYPE: DNA
<213> ORGANISM: Mus Musculus

<400> SEQUENCE: 5
atggctcgta ctaagcagac cgctcgcaag tctaccggcg gcaaggcccc gcgcaagcag     60
ctggccacca aggccgcccg caagagcgcc ccggccaccg gcggcgtgaa gaagcctcac    120
cgctaccgtc ccggcactgt ggcactgcgc gagatccggc gctaccagaa gtcgaccgag    180
ctgctgatcc gcaagctgcc gttccagcgc ctggtgcgcg agatcgcgca ggacttcaag    240
accgacctgc gcttccagag ctcggccgtc atggctctgc aggaggcctg tgaggcctac    300
ctcgtgggtc tgtttgagga caccaacctg tgcgccatcc acgccaagcg tgtcaccatc    360
atgcccaagg acatccagct ggcccgtcgc atccgcgggg agagggctta a             411

<210> SEQ ID NO 6
<211> LENGTH: 411
<212> TYPE: DNA
```

<213> ORGANISM: Mus Musculus

<400> SEQUENCE: 6

```
atggctcgtg ctaagcagac cgctcgcaag tctaccggcg gcaaggcccc gcgcaagcag    60
ctggccacca aggccgcccg caagagcgcc ccggccaccg gcggcgtgaa gaagcctcac   120
cgctaccgtc ccggcactgt ggcactgcgc gagatccggc gctaccagaa gtcgaccgag   180
ctgctgatcc gcaagctgcc gttccagcgc ctggtgcgcg agatcgcgca ggacttcaag   240
accgacctgc gcttccagag ctcggccgtc atggctctgc aggaggcctg tgaggcctac   300
ctcgtgggtc tgtttgagga caccaacctg tgcgccatcc acgccaagcg tgtcaccatc   360
atgcccaagg acatccagct ggcccgtcgc atccgcgggg agagggctta a            411
```

<210> SEQ ID NO 7
<211> LENGTH: 136
<212> TYPE: PRT
<213> ORGANISM: Drosophila melanogaster

<400> SEQUENCE: 7

```
Met Ala Arg Thr Lys Gln Thr Ala Arg Lys Ser Thr Gly Gly Lys Ala
1               5                   10                  15

Pro Arg Lys Gln Leu Ala Thr Lys Ala Ala Arg Lys Ser Ala Pro Ala
            20                  25                  30

Thr Gly Gly Val Lys Lys Pro His Arg Tyr Arg Pro Gly Thr Val Ala
        35                  40                  45

Leu Arg Glu Ile Arg Arg Tyr Gln Lys Ser Thr Glu Leu Leu Ile Arg
    50                  55                  60

Lys Leu Pro Phe Gln Arg Leu Val Arg Glu Ile Ala Gln Asp Phe Lys
65                  70                  75                  80

Thr Asp Leu Arg Phe Gln Ser Ser Ala Val Met Ala Leu Gln Glu Ala
                85                  90                  95

Ser Glu Ala Tyr Leu Val Gly Leu Phe Glu Asp Thr Asn Leu Cys Ala
            100                 105                 110

Ile His Ala Lys Arg Val Thr Ile Met Pro Lys Asp Ile Gln Leu Ala
        115                 120                 125

Arg Arg Ile Arg Gly Glu Arg Ala
    130                 135
```

<210> SEQ ID NO 8
<211> LENGTH: 136
<212> TYPE: PRT
<213> ORGANISM: Drosophila melanogaster

<400> SEQUENCE: 8

```
Met Ala Arg Ala Lys Gln Thr Ala Arg Lys Ser Thr Gly Gly Lys Ala
1               5                   10                  15

Pro Arg Lys Gln Leu Ala Thr Lys Ala Ala Arg Lys Ser Ala Pro Ala
            20                  25                  30

Thr Gly Gly Val Lys Lys Pro His Arg Tyr Arg Pro Gly Thr Val Ala
        35                  40                  45

Leu Arg Glu Ile Arg Arg Tyr Gln Lys Ser Thr Glu Leu Leu Ile Arg
    50                  55                  60

Lys Leu Pro Phe Gln Arg Leu Val Arg Glu Ile Ala Gln Asp Phe Lys
65                  70                  75                  80

Thr Asp Leu Arg Phe Gln Ser Ser Ala Val Met Ala Leu Gln Glu Ala
                85                  90                  95
```

Ser Glu Ala Tyr Leu Val Gly Leu Phe Glu Asp Thr Asn Leu Cys Ala
            100                 105                 110

Ile His Ala Lys Arg Val Thr Ile Met Pro Lys Asp Ile Gln Leu Ala
        115                 120                 125

Arg Arg Ile Arg Gly Glu Arg Ala
    130                 135

<210> SEQ ID NO 9
<211> LENGTH: 136
<212> TYPE: PRT
<213> ORGANISM: Homo sapiens

<400> SEQUENCE: 9

Met Ala Arg Thr Lys Gln Thr Ala Arg Lys Ser Thr Gly Gly Lys Ala
1               5                   10                  15

Pro Arg Lys Gln Leu Ala Thr Lys Ala Ala Arg Lys Ser Ala Pro Ala
            20                  25                  30

Thr Gly Gly Val Lys Lys Pro His Arg Tyr Arg Pro Gly Thr Val Ala
        35                  40                  45

Leu Arg Glu Ile Arg Arg Tyr Gln Lys Ser Thr Glu Leu Leu Ile Arg
    50                  55                  60

Lys Leu Pro Phe Gln Arg Leu Val Arg Glu Ile Ala Gln Asp Phe Lys
65                  70                  75                  80

Thr Asp Leu Arg Phe Gln Ser Ser Ala Val Met Ala Leu Gln Glu Ala
                85                  90                  95

Cys Glu Ala Tyr Leu Val Gly Leu Phe Glu Asp Thr Asn Leu Cys Ala
            100                 105                 110

Ile His Ala Lys Arg Val Thr Ile Met Pro Lys Asp Ile Gln Leu Ala
        115                 120                 125

Arg Arg Ile Arg Gly Glu Arg Ala
    130                 135

<210> SEQ ID NO 10
<211> LENGTH: 136
<212> TYPE: PRT
<213> ORGANISM: Homo sapiens

<400> SEQUENCE: 10

Met Ala Arg Ala Lys Gln Thr Ala Arg Lys Ser Thr Gly Gly Lys Ala
1               5                   10                  15

Pro Arg Lys Gln Leu Ala Thr Lys Ala Ala Arg Lys Ser Ala Pro Ala
            20                  25                  30

Thr Gly Gly Val Lys Lys Pro His Arg Tyr Arg Pro Gly Thr Val Ala
        35                  40                  45

Leu Arg Glu Ile Arg Arg Tyr Gln Lys Ser Thr Glu Leu Leu Ile Arg
    50                  55                  60

Lys Leu Pro Phe Gln Arg Leu Val Arg Glu Ile Ala Gln Asp Phe Lys
65                  70                  75                  80

Thr Asp Leu Arg Phe Gln Ser Ser Ala Val Met Ala Leu Gln Glu Ala
                85                  90                  95

Cys Glu Ala Tyr Leu Val Gly Leu Phe Glu Asp Thr Asn Leu Cys Ala
            100                 105                 110

Ile His Ala Lys Arg Val Thr Ile Met Pro Lys Asp Ile Gln Leu Ala
        115                 120                 125

Arg Arg Ile Arg Gly Glu Arg Ala
    130                 135

<210> SEQ ID NO 11
<211> LENGTH: 136
<212> TYPE: PRT
<213> ORGANISM: Mus Musculus

<400> SEQUENCE: 11

Met Ala Arg Thr Lys Gln Thr Ala Arg Lys Ser Thr Gly Gly Lys Ala
1               5                   10                  15

Pro Arg Lys Gln Leu Ala Thr Lys Ala Ala Arg Lys Ser Ala Pro Ala
            20                  25                  30

Thr Gly Gly Val Lys Lys Pro His Arg Tyr Arg Pro Gly Thr Val Ala
        35                  40                  45

Leu Arg Glu Ile Arg Arg Tyr Gln Lys Ser Thr Glu Leu Leu Ile Arg
    50                  55                  60

Lys Leu Pro Phe Gln Arg Leu Val Arg Glu Ile Ala Gln Asp Phe Lys
65                  70                  75                  80

Thr Asp Leu Arg Phe Gln Ser Ser Ala Val Met Ala Leu Gln Glu Ala
                85                  90                  95

Cys Glu Ala Tyr Leu Val Gly Leu Phe Glu Asp Thr Asn Leu Cys Ala
            100                 105                 110

Ile His Ala Lys Arg Val Thr Ile Met Pro Lys Asp Ile Gln Leu Ala
        115                 120                 125

Arg Arg Ile Arg Gly Glu Arg Ala
    130                 135

<210> SEQ ID NO 12
<211> LENGTH: 136
<212> TYPE: PRT
<213> ORGANISM: Mus Musculus

<400> SEQUENCE: 12

Met Ala Arg Ala Lys Gln Thr Ala Arg Lys Ser Thr Gly Gly Lys Ala
1               5                   10                  15

Pro Arg Lys Gln Leu Ala Thr Lys Ala Ala Arg Lys Ser Ala Pro Ala
            20                  25                  30

Thr Gly Gly Val Lys Lys Pro His Arg Tyr Arg Pro Gly Thr Val Ala
        35                  40                  45

Leu Arg Glu Ile Arg Arg Tyr Gln Lys Ser Thr Glu Leu Leu Ile Arg
    50                  55                  60

Lys Leu Pro Phe Gln Arg Leu Val Arg Glu Ile Ala Gln Asp Phe Lys
65                  70                  75                  80

Thr Asp Leu Arg Phe Gln Ser Ser Ala Val Met Ala Leu Gln Glu Ala
                85                  90                  95

Cys Glu Ala Tyr Leu Val Gly Leu Phe Glu Asp Thr Asn Leu Cys Ala
            100                 105                 110

Ile His Ala Lys Arg Val Thr Ile Met Pro Lys Asp Ile Gln Leu Ala
        115                 120                 125

Arg Arg Ile Arg Gly Glu Arg Ala
    130                 135

<210> SEQ ID NO 13
<211> LENGTH: 411
<212> TYPE: DNA
<213> ORGANISM: Drosophila melanogaster

<400> SEQUENCE: 13
atggctcgtg acaagcaaac tgctcgcaaa tcgactggtg aaaggcgcc acgcaaacaa         60

```
ctggctacta aggccgctcg caagagtgct ccagccaccg gaggtgtgaa gaagccccac    120
cgctatcgcc ctggaaccgt ggccttgcgt gaaattcgtc gctaccaaaa gagcaccgag    180
cttctaatcc gcaagctgcc tttccagcgt ctggtgcgtg aaatcgctca ggactttaag    240
acggacttgc gattccagag ctcggcggtt atggctctgc aggaagctag cgaagcctac    300
ctggttggtc tcttcgaaga taccaacttg tgtgccattc atgccaagcg tatcaccata    360
atgcccaaag acatccagtt agcgcgacgc attcgcggcg agcgtgctta a             411

<210> SEQ ID NO 14
<211> LENGTH: 411
<212> TYPE: DNA
<213> ORGANISM: Homo sapiens

<400> SEQUENCE: 14
atggcccgag acaagcagac tgcgcgcaag tcaacggtg gcaaggcgcc gcgcaagcag     60
ctggccacca aggtggctcg caagagcgca cctgccactg gcggcgtgaa gaagccgcac    120
cgctaccggc ccggcacggt ggcgcttcgc gagatccgcc gctaccagaa gtccactgag    180
ctgctaatcc gcaagttgcc cttccagcgg ctgatgcgcg agatcgctca ggactttaag    240
accgacctgc gcttccagag ctcggccgtg atggcgctgc aggaggcgtg cgagtcttac    300
ctggtggggc tgtttgagga caccaacctg tgtgtcatcc atgccaaacg ggtcaccatc    360
atgcctaagg acatccagct ggcacgccgt atccgcgggg agcgggccta g             411

<210> SEQ ID NO 15
<211> LENGTH: 411
<212> TYPE: DNA
<213> ORGANISM: Mus Musculus

<400> SEQUENCE: 15
atggctcgtg acaagcagac cgctcgcaag tctaccggcg gcaaggcccc gcgcaagcag     60
ctggccacca aggccgcccg caagagcgcc ccggccaccg gcggcgtgaa gaagcctcac    120
cgctaccgtc ccggcactgt ggcactgcgc gagatccggc gctaccagaa gtcgaccgag    180
ctgctgatcc gcaagctgcc gttccagcgc ctggtgcgcg agatcgcgca ggacttcaag    240
accgacctgc gcttccagag ctcggccgtc atggctctgc aggaggcctg tgaggcctac    300
ctcgtgggtc tgtttgagga caccaacctg tgcgccatcc acgccaagcg tgtcaccatc    360
atgcccaagg acatccagct ggcccgtcgc atccgcgggg agagggctta a             411

<210> SEQ ID NO 16
<211> LENGTH: 136
<212> TYPE: PRT
<213> ORGANISM: Drosophila melanogaster

<400> SEQUENCE: 16
```

Met Ala Arg Asp Lys Gln Thr Ala Arg Lys Ser Thr Gly Gly Lys Ala
1               5                   10                  15

Pro Arg Lys Gln Leu Ala Thr Lys Ala Ala Arg Lys Ser Ala Pro Ala
            20                  25                  30

Thr Gly Gly Val Lys Lys Pro His Arg Tyr Arg Pro Gly Thr Val Ala
        35                  40                  45

Leu Arg Glu Ile Arg Arg Tyr Gln Lys Ser Thr Glu Leu Leu Ile Arg
    50                  55                  60

Lys Leu Pro Phe Gln Arg Leu Val Arg Glu Ile Ala Gln Asp Phe Lys
65                  70                  75                  80

```
Thr Asp Leu Arg Phe Gln Ser Ser Ala Val Met Ala Leu Gln Glu Ala
                85                  90                  95

Ser Glu Ala Tyr Leu Val Gly Leu Phe Glu Asp Thr Asn Leu Cys Ala
            100                 105                 110

Ile His Ala Lys Arg Val Thr Ile Met Pro Lys Asp Ile Gln Leu Ala
            115                 120                 125

Arg Arg Ile Arg Gly Glu Arg Ala
        130                 135

<210> SEQ ID NO 17
<211> LENGTH: 136
<212> TYPE: PRT
<213> ORGANISM: Homo sapiens

<400> SEQUENCE: 17

Met Ala Arg Asp Lys Gln Thr Ala Arg Lys Ser Thr Gly Gly Lys Ala
1               5                   10                  15

Pro Arg Lys Gln Leu Ala Thr Lys Ala Ala Arg Lys Ser Ala Pro Ala
            20                  25                  30

Thr Gly Gly Val Lys Lys Pro His Arg Tyr Arg Pro Gly Thr Val Ala
        35                  40                  45

Leu Arg Glu Ile Arg Arg Tyr Gln Lys Ser Thr Glu Leu Leu Ile Arg
    50                  55                  60

Lys Leu Pro Phe Gln Arg Leu Val Arg Glu Ile Ala Gln Asp Phe Lys
65                  70                  75                  80

Thr Asp Leu Arg Phe Gln Ser Ser Ala Val Met Ala Leu Gln Glu Ala
                85                  90                  95

Cys Glu Ala Tyr Leu Val Gly Leu Phe Glu Asp Thr Asn Leu Cys Ala
            100                 105                 110

Ile His Ala Lys Arg Val Thr Ile Met Pro Lys Asp Ile Gln Leu Ala
            115                 120                 125

Arg Arg Ile Arg Gly Glu Arg Ala
        130                 135

<210> SEQ ID NO 18
<211> LENGTH: 136
<212> TYPE: PRT
<213> ORGANISM: Mus Musculus

<400> SEQUENCE: 18

Met Ala Arg Asp Lys Gln Thr Ala Arg Lys Ser Thr Gly Gly Lys Ala
1               5                   10                  15

Pro Arg Lys Gln Leu Ala Thr Lys Ala Ala Arg Lys Ser Ala Pro Ala
            20                  25                  30

Thr Gly Gly Val Lys Lys Pro His Arg Tyr Arg Pro Gly Thr Val Ala
        35                  40                  45

Leu Arg Glu Ile Arg Arg Tyr Gln Lys Ser Thr Glu Leu Leu Ile Arg
    50                  55                  60

Lys Leu Pro Phe Gln Arg Leu Val Arg Glu Ile Ala Gln Asp Phe Lys
65                  70                  75                  80

Thr Asp Leu Arg Phe Gln Ser Ser Ala Val Met Ala Leu Gln Glu Ala
                85                  90                  95

Cys Glu Ala Tyr Leu Val Gly Leu Phe Glu Asp Thr Asn Leu Cys Ala
            100                 105                 110

Ile His Ala Lys Arg Val Thr Ile Met Pro Lys Asp Ile Gln Leu Ala
            115                 120                 125
```

```
Arg Arg Ile Arg Gly Glu Arg Ala
130                 135
```